US009651554B2

(12) United States Patent
Wong et al.

(10) Patent No.: US 9,651,554 B2
(45) Date of Patent: May 16, 2017

(54) MOLECULAR DIAGNOSTIC METHODS FOR PREDICTING BRAIN METASTASIS OF BREAST CANCER

(75) Inventors: Stephen T. C. Wong, Missouri City, TX (US); Hong Zhao, Houston, TX (US)

(73) Assignee: The Methodist Hospital Research Institute, Houston, TX (US)

(*) Notice: Subject to any disclaimer, the term of this patent is extended or adjusted under 35 U.S.C. 154(b) by 1150 days.

(21) Appl. No.: 13/245,706

(22) Filed: Sep. 26, 2011

(65) Prior Publication Data
US 2012/0184560 A1 Jul. 19, 2012

Related U.S. Application Data

(60) Provisional application No. 61/386,186, filed on Sep. 24, 2010.

(51) Int. Cl.
| *C12Q 1/68* | (2006.01) |
| *C07H 21/04* | (2006.01) |
| *G01N 33/574* | (2006.01) |
| *A61K 31/404* | (2006.01) |
| *A61K 31/496* | (2006.01) |
| *A61N 5/10* | (2006.01) |
| *G06F 19/12* | (2011.01) |
| *G06F 19/00* | (2011.01) |

(52) U.S. Cl.
CPC ..... *G01N 33/57415* (2013.01); *A61K 31/404* (2013.01); *A61K 31/496* (2013.01); *G01N 33/57407* (2013.01); *A61N 5/103* (2013.01); *G01N 2500/00* (2013.01); *G01N 2800/56* (2013.01); *G01N 2800/60* (2013.01); *G06F 19/12* (2013.01); *G06F 19/704* (2013.01)

(58) Field of Classification Search
None
See application file for complete search history.

(56) References Cited

PUBLICATIONS

Bos (Nature vol. 459 Jun. 18, 2009 pp. 1005-1009).*
Whitehead (Genome Biology 2005 vol. 6 Issue 2 Article R13).*
Hoshikawa et al (Physical Genomics 2003 vol. 12 pp. 209-219).*
Cheung (Nature Genetics 2003 vol. 33 pp. 422-425).*
Chan (G&P magazine 2006 vol. 6 No. 3 pp. 20-26).*
Lin (Journal of Clinical Oncology vol. 26 No. 12 Apr. 20, 2008).*
Chen (Molecular & Cellular Proteomics 1:304-313, 2002).*
Lichtinghagen (European Urology 42 (2002) pp. 398-406).*
Alix-Panabieres, Catherine et al., "Full-Length Cytokeratin-19 is Released by Human Tumor Cells: a Potential Role in Metastatic Progression of Breast Cancer," *Breast Cancer Res.*, 11(3):R39 (Jun. 23, 2009), 10 pages.
Andrews, DW et al., "Whole Brain Radiation Therapy With or Without Stereotactic Radiosurgery Boost for Patients with One to Three Brain Metastases: Phase III Results of the RTOG 9508 Randomised Trial," *Lancet*, 363(9422):1665-1672 (May 22, 2004).
Aoyama, Hidefumi et al., "Stereotactic Radiosurgery plus Whole-Brain Radiation Therapy vs. Stereotactic Radiosurgery Alone for Treatment of Brain Metastases: a Randomized Controlled Trial," *J. Am. Med. Assoc.*, 295(21):2483-2491 (Jun. 7, 2006).
Arighi, Elena et al., "RET Tyrosine Kinase Signaling in Development and Cancer," *Cytokine Growth Factor Rev.*, 16(2005):441-467 (Jun. 27, 2005).
Ashburn, Ted T. and Thor, Karl B., "Drug Repositioning: Identifying and Developing New Uses for Existing Drugs," *Nature Rev.*, 3:673-683 (Aug. 2004).
Atkins, Michael et al., "Sunitinib Maleate," *Nature Rev.*, 5:279-280 (Apr. 2006).
Bai, Wenjia, et al., "Tracking of Migrating Glioma Cells in Feature Space," In: Biomedical Imaging: From Nano to Macro, ISBI 4th IEEE Inte. Symp., pp. 272-275 (2007).
Ban, Kechen et al., "BCR-ABL1 Mediates Up-Regulation of Fyn in Chronic Myelogenous Leukemia," *Blood*, 111(5):2904-2908 (Jan. 7, 2008).
Batada, Nizar N. et al., "Stratus Not Altocumulus: a New View of the Yeast Protein Interaction Network," *PLoS Biol.*, 4(10):e317, pp. 1720-1731 (Oct. 2006).
Bhujwalla, Zaver M. et al., "Vascular Differences Detected by MRI for Metastatic Versus Nonmetastatic Breast and Prostate Cancer Xenografts," *Neoplasia*, 3(2):143-153 (Mar.-Apr. 2001).
Bild, Andrea H. et al., "Oncogenic Pathway Signatures in Human Cancers as a Guide to Targeted Therapies," *Nature*, 439(19):353-357 (Jan. 19, 2006).
Bos, Paula D. et al., "Genes That Mediate Breast Cancer Metastasis to the Brain," *Nature*, 459(7249):1005-1009 (Jun. 18, 2009).
"Brain Metasis," *Curr. Probl. Surg*, Aug. 2004, pp. 665-741.
Burstein, H. J. et al., "Isolated Central Nervous System Metastases in Patients with HER2-Overexpressing Advanced Breast Cancer Treated with First-Line Trastuzumab-Based Therapy," *Ann. Oncol.*, 16(11):1772-1777 (Sep. 8, 2005).
Campillos, Monica et al., "Drug Target Identification Using Side-Effect Similarity," Science, 321(5886):263-266 (Jul. 11, 2008).
Carmeliet, Peter and Jain, Rakesh K., "Principles and Mechanisms of Vessel Normalization for Cancer and Other Angiogenic Diseases," *Nature Rev.*, 10(6):417-427 (Jun. 2011).
Chang, Eric L., and Lo, Simon, "Diagnosis and Management of Central Nervous System Metastases from Breast Cancer," *Oncologist*, 8(5):398-410 (Oct. 2003).
Chang, Jenny C., et al., "Gene Expression Profiling for the Prediction of Therapeutic Response to Docetaxel in Patients with Breast Cancer," *J. Surg. Res.*, 362(9381):362-369 (Aug. 2, 2003).
Chang, Sharon B., et al., "Rapamycin Inhibits Proliferation of Estrogen-Receptor-Positive Breast Cancer Cells," *J. Surg. Res.*, 138(1):37-44 (Mar. 2007).
Cheng, Xiaoyun and Hung, Mien-Chie, "Breast Cancer Brain Metastases," *Cancer Metastasis Rev.*, 26(3):635-643 (Dec. 2007).
Chiang, Anne C. and Massagué, Joan, "Molecular Basis of Metastasis," *N. Engl. J. Med*, 359(26): 2814-2823 (Dec. 25, 2008).
Dalerba, Piero et al., "Cancer Stem Cells: Models and Concepts," *Annu. Rev. Med.*, 58:267-284 (Feb. 2007).

(Continued)

Primary Examiner — Amanda Haney
(74) Attorney, Agent, or Firm — Cesari and McKenna LLP

(57) ABSTRACT

Disclosed are molecular diagnostic compositions and methods for predicting brain metastasis of breast cancer, as well as methods for drug repositioning to identify existing and new therapeutics for use in developing individualized, patient-specific treatment regimens for improving diagnoses and patient outcomes in individuals at risk for brain metastasis of breast cancer.

5 Claims, 26 Drawing Sheets

(56) References Cited

PUBLICATIONS

Deangelis, Lisa M. et al., "Radiation-Induced Dementia in Patients Cured of Brain Metastases," *Neurology*, 39(6):789-796 (Jun. 1989).

Dekker, Lodewijk, "Novel Approaches to Drug Discover in Signal Transduction," *Biotechnol. J.*, 3(4): 428-429 (Apr. 2008).

Dewan, M. Z. et al., "Stromel Cell-Derived Factor-1 and CXCR4 Receptor Interaction in Tumor Growth and Metastasis of Breast Cancer," *Biomed. Pharmacother.*, 60(6):273-276 (Jul. 2006).

Duchnowska, Renata, and Szczylik, Cezary, "Central Nervous System Metastases in Breast Cancer Patients Administered Trastuzumab," *Cancer Treat. Rev.*, 31(4):312-318 (Jun. 2005).

Esseghir, Selma et al., "A Role for Glial Cell-Derived Neurotrophic Factor-Induced Expression by Inflammatory Cytokines and RET/GFR Alpha 1 Receptor Up-Regulation in Breast Cancer," *Cancer Res.*, 67(24):11732-11741 (Dec. 15, 2007).

Evans, AJ et al., "Brain Metastases from Breast Cancer: Identification of a High-Risk Group," *Clin. Oncol. (R. Coll. Radiol.)*, 16(5):345-349 (Aug. 2004).

Finn, Richard S. et al., "Dasatinib, an Orally Active Small Molecule Inhibitor of Both the Src and Abl Kinases, Selectively Inhibits Growth of Basal-Type/"Triple-Negative" Breast Cancer Cell Lines Growing In Vitro," *Breast Cancer Res. Treat.*, 105(3):319-326 (Nov. 2007).

Forsti, Asta et al., "Polymorphisms in the KDR and POSTN Genes: Association with Breast Cancer Susceptibility and Prognosis," *Breast Cancer Res. Treat.*, 101(1):83-93 (Jan. 2007).

Fulford, Laura G. et al., "Basal-Like Grade III Invasive Ductal Carcinoma of the Breast: Patterns of Metastasis and Long-Term Survival," *Breast Cancer Res.*, 9(1):R4, 11 pages (Jan. 11, 2007).

Gabos, Zsolt et al., "Prognostic Significance of Human Epidermal Growth Factor Receptor Positivity for the Development of Brain Metastasis after Newly Diagnosed Breast Cancer," *J. Clin. Oncol.*, 24(36):5658-5663 (Dec. 20, 2006).

Gaedcke, Jochem et al., "Predominance of the Basal Type and HER-2/Neu Type in Brain Metastasis from Breast Cancer," *Mod. Pathol.*, 20(8):864-870 (Aug. 2007).

Gordon, M. S. et al., "Activity of Cabozantinib (XL184) in Soft Tissue and Bone: Results of a Phase II Randomized Discontinuation Trial (RDT) in Patients (pts) with Advanced Solid Tumors," *J. Clin. Oncol.*, 29:3010 (2011).

Gore, Martin E. et al., "Safety and Efficacy of Sunitinib for Metastatic Renal-Cell Carcinoma: an Expanded-Access Trial," *Lancet Oncol.*, 10(8):757-763 (Aug. 2009).

Gril, Brunilde et al., "Pazopanib Reveals a Role for Tumor Cell B-Raf in the Prevention of HER2+ Breast Cancer Brain Metastasis," *Clin. Cancer Res.*, 17(1):142-153 (Jan. 1, 2011).

Grimshaw, Matthew J. et al., "Mammosphere Culture of Metastatic Breast Cancer Cells Enriches for Tumorigenic Breast Cancer Cells," *Breast Cancer Res.*, 10(3):R52, 10 pages (Jun. 9, 2008).

Groves, Morris D. et al., "Biomarkers of Disease: Cerebrospinal Fluid Vascular Endothelial Growth Factor (VEGF) and Stromal Cell Derived Factor (SDF)-1 Levels in Patients with Neoplastic Meningitis (NM) Due to Breast Cancer, Lung Cancer and Melanoma," *J. Neurooncol.*, 94(2):229-234 (Sep. 2009).

Hamosh, Ada et al., "Online Mendelian Inheritance in Man (OMIM), a knowledgebase of human genes and genetic disorders," *Nucl. Acids Res.*, 33:D514-D517 (Jan. 1, 2005).

Han, Jing-Dong et al., "Evidence for Dynamically Organized Modularity in the Yeast Protein-Protein Interaction Network," *Nature*, 430:88-93 (Jul. 1, 2004).

Hatake, Kiyohiko et al., "Next Generation Molecular Targeted Agents for Breast Cancer: Focus on EGFR and VEGFR Pathways," *Breast Cancer*, 14(2):132-149 (Apr. 2007).

Haubeiss, Silke et al., "Dasatinib Reverses Cancer-Associated Fibroblasts (CAFS) from Primary Lung Carcinomas to a Phenotype Comparable to that of Normal Fibroblasts," *Molec. Cancer*, 9:168, pp. 1-8 (Jun. 27, 2010).

Helgason, Helgi H. et al., "Brain Metastases in Patients with Renal Cell Cancer Receiving New Targeted Treatment," *J. Clin. Oncol.*, 26(1):152-4 (2008).

Hendrickson, Frank R. et al., "The Influence of Surgery and Radiation Therapy on Patients with Brain Metastases," *Int. J. Radiat. Oncol. Biol. Phys.*, 9(5):623-627 (May 1983).

Herrlinger, U. et al., "Vascular Endothelial Growth Factor (VEGF) in Leptomeningeal Metastasis: Diagnostic and Prognostic Value," *Br. J. Cancer*, 91(2):219-224 (Jul. 2004).

Hicks, David G. et al., "Breast Cancers with Brain Metastases are More Likely to be Estrogen Receptor Negative, Express the Basal Cytokeratin CK5/6, and Overexpress HER2 or EGFR," *Am. J. Surg. Pathol.*, 30(9):1097-1104 (Sep. 2006).

Hwu, WJ et al., "Phase II Study of Temozolomide Plus Thalidomide for the Treatment of Metastatic Melanoma," *J. Clin. Oncol.*, 21(17):3351-3356 (Sep. 1, 2003).

Hwu, Wen-Jen et al., "Temozolomide Plus Thalidomide in Patients with Brain Metastases from Melanoma: a Phase II study," Cancer, 103(12):2590-2597 (Jun. 15, 2005).

Iorio, Francesco et al., "Discovery of Drug Mode of Action and Drug Repositioning from Transcriptional Responses," *Proc. Natl. Acad. Sci. USA*, 107(33):14621-14626 (Aug. 17, 2010).

Ishizawar, Rumey, and Parsons, Sarah J., "c-Src and Cooperating Partners in Human Cancer," *Cancer Cell*, 6(3):209-214 (Sep. 2004).

Kan, Zhengyan et al., "Diverse Somatic Mutation Patterns and Pathway Alterations in Human Cancers," *Nature*, 466(7308):869-873 (Aug. 2010).

Kang, Hua et al., "The Elevated Level of CXCR4 is Correlated with Nodal Metastasis of Human Breast Cancer," Breast (Edinburgh, Scotland), 14(5):360-367 (Oct. 2005).

Kang, Yibin et al., "A Multigenic Program Mediating Breast Cancer Metastasis to Bone," *Cancer Cell*, 3(6):537-549 (Jun. 2003).

Kaplan, Rosandra N. et al., "VEGFR1-Positive Haematopoietic Bone Marrow Progenitors Initiate the Pre-Metastatic Niche," *Nature*, 438(7069):820-827 (Dec. 8, 2005).

Keiser, Michael J. et al., "Predicting New Molecular Targets for Known Drugs," *Nature*, 462(7270):175-181 (Nov. 12, 2009).

Kennecke, Hagen et al., "Metastatic Behavior of Breast Cancer Subtypes," *J. Clin. Oncol.*, 28(20):3271-3277 (Jul. 10, 2010).

Kim, Lee Su et al., "Vascular Endothelial Growth Factor Expression Promotes the Growth of Breast Cancer Brain Metastases in Nude Mice," *Clin. Exp. Metastasis*, 21(2):107-118 (2004).

Klein, Andreas et al., "Identification of Brain- and Bone-Specific Breast Cancer Metastasis Genes," *Cancer Lett.*, 276(2):212-220 (Apr. 18, 2009).

Klos, Kevin J. and O'Neill, Brian Patrick, "Brain Metastases," *Neurologist*, 10(1):31-46 (Jan. 2004).

Kondziolka, Douglas et al., "Stereotactic Radiosurgery Plus Whole Brain Radiotherapy Versus Radiotherapy Alone for Patients with Multiple Brain Metastases," *Int. J. Radiat. Oncol. Biol. Phys.*, 45(2):427-434 (Sep. 1, 1999).

Koutras, Angelos K. et al., "Brain Metastasis in Renal Cell Cancer Responding to Sunitinib," *Anticancer Res.*, 27(6C):4255-4257 (2007).

Kurebayashi, Junichi et al., "Preferential Antitumor Effect of the Src Inhibitor Dasatinib Associated with a Decreased Proportion of Aldehyde Dehydrogenase 1-Positive Cells in Breast Cancer Cells of the Basal B Subtype," *BMC Cancer*, 10:568 pp. 2407-2410 (Oct. 20, 2010).

Lamb, Justin et al., "The Connectivity Map: Using Gene-Expression Signatures to Connect Small Molecules, Genes, and Disease," *Science*, 313(5795):1929-1935 (Sep. 29, 2006).

Lapidot, T., and Kollet, O., "The Essential Roles of the Chemokine SDF-1 and its Receptor CXCR4 in Human Stem Cell Homing and Repopulation of Transplanted Immune-Deficient NOD/SCID and NOD/SCID/B2m(Null) Mice," *Leukemia*, 16(10):1992-2003 (Oct. 2002).

Lassman, Andrew B., and Deangelis, Lisa M., "Brain Metastases," *Neurol. Clin.*, 21(1):1-23, (Feb. 2003).

Lee, Tae-Hee et al., "Vascular Endothelial Growth Factor Modulates the Transendothelial Migration of MDA-MB-231 Breast Cancer Cells Through Regulation of Brain Microvascular Endothelial Cell Permeability," *J. Biol. Chem.*, 278(7):5277-5284 (Feb. 14, 2003).

Li, Liheng, and Neaves, William B., "Normal Stem Cells and Cancer Stem Cells: the Niche Matters," *Cancer Res.*, 66(9):4553-4557 (May 1, 2006).

(56) References Cited

OTHER PUBLICATIONS

Lin, Nancy U. et al., "CNS Metastases in Breast Cancer," *J. Clin. Oncol.*, 22(17):3608-3617 (Sep. 1, 2004).
Lin, Nancy U. et al., "CNS Metastases in Breast Cancer: Old Challenge, New Frontiers," *Clin. Cancer Res.*, 19(23):6404-6418 (Dec. 1, 2013).
Lin, Nancy U. et al., "Sites of distant recurrence and clinical outcomes in patients with metastatic triple-negative breast cancer: high incidence of central nervous system metastases," *Cancer*, 113(10):2638-2645 (Nov. 15, 2008).
Linderholm, Barbro et al., "Correlation of vascular endothelial growth factor content with recurrences, survival, and first relapse site in primary node-positive breast carcinoma after adjuvant treatment," *J. Clin. Oncol.*, 18(7):1423-31 (Apr. 2000).
Marotta, Lauren L. and Polyak, Kornelia, "Cancer stem cells: a model in the making," *Curr. Opin. Genet. Develop.*, 19(1):44-50 (Feb. 2009).
Martin, Berta et al., "Biological pathways contributing to organ-specific phenotype of brain Metastatic Cells," *J. Proteome Res.*, 7(3):908-920 (Mar. 2008).
Masood, Rizwan et al., "Vascular endothelial growth factor (VEGF) is an autocrine growth factor for VEGF receptor-positive human tumors," *Blood*, 98(6):1904-1913 (Sep. 15, 2001).
Medioni, J. et al., "Complete cerebral response with sunitinib for metastatic renal cell carcinoma," *Ann. Oncol.*, 18(7):1282-1283 (Jul. 2007).
Miller, K. D. et al., "Occult central nervous system involvement in patients with metastatic breast cancer: prevalence, predictive factors and impact on overall survival," *Ann. Oncol.*, 14(7):1072-1077 (2003).
Miller, Mitchell A., "Chemical Database Techniques in Drug Discovery," *Nat. Rev. Drug Discov.*, 1(3):220-227 (Mar. 2002).
Milo, R. et al., "Network Motifs: Simple Building Blocks of Complex Networks," *Science*, 298(5594):824-827 (Oct. 25, 2002).
Minn, Andy J. et al., "Distinct organ-specific metastatic potential of individual breast cancer cells and primary tumors," *J. Clin. Invest.* 115(1):44-55 (Jan. 3, 2005).
Minn, Andy J et al., "Genes that Mediate Breast Cancer Metastasis to Lung," *Nature*, 436(7050):518-524 (Jul. 28, 2005).
Mintz, Arlan H. et al., "A Randomized Trial to Assess the Efficacy of Surgery in Addition to Radiotherapy in Patients with a Single Cerebral Metastasis," *Cancer*, 78(7):1470-1476 (Oct. 1, 1996).
Monsky, Wayne L. et al., "Role of Host Microenvironment in Angiogenesis and Microvascular Functions in Human Breast Cancer Xenografts: Mammary Fat Pad Versus Cranial Tumors," *Clin. Cancer Res.*, 8(4):1008-1013 (Apr. 2002).
Morandi, Andrea et al., "RET in Breast Cancer: Functional and Therapeutic Implications," Trends Molec. Med., 17(3):149-157 (Mar. 2011).
Motzer, Robert J. et al., "Activity of SU11248, a Multitargeted Inhibitor of Vascular Endothelial Growth Factor Receptor and Platelet-Derived Growth Factor Receptor, in Patients with Metastatic Renal Cell Carcinoma," *J. Clin. Oncol.*, 24(1):16-24 (Jan. 1, 2006).
Motzer, Robert J. et al., "Sunitinib in Patients with Metastatic Renal Cell Carcinoma," *J. Am. Med. Assoc.*, 295(21):2516-2524 (Jun. 7, 2005).
Murray, Lesley J. et al., "SU11248 Inhibits Tumor Growth and CSF-1R-Dependent Osteolysis in an Experimental Breast Cancer Bone Metastasis Model," *Clin. Exper. Metastasis*, 20(8):757-766 (Dec. 2003).
Narita, Yoshitaka and Shibui, Soichiro, "Strategy of Surgery and Radiation Therapy for Brain Metastases," *Int. J. Clin. Oncol.*, 14(4):275-280 (Aug. 2009).
Neman, Josh et al., "Classification of Genomic Changes in Breast Cancer Brain Metastasis," *Neurosurgery*, 67(2):N18-N19 (Aug. 2010).
Noordijk, Evert M. et al., "The Choice of Treatment of Single Brain Metastasis Should be Based on Extracranial Tumor Activity and Age," *Int. J. Radiat. Oncol. Biol. Phys.*, 29(4):711-717 (Jul. 1994).

Ono, Makiko et al., "Brain Metastases in Patients who Receive Trastuzumab-Containing Chemotherapy for HER2-Overexpressing Metastatic Breast Cancer," *Int. J. Clin. Oncol.*, 14(1):48-52 (Feb. 2009).
Pajouhesh, Hassan, and Lenz, George R., "Medicinal Chemical Properties of Successful Central Nervous System Drugs," *NeuroRx*, 2(4):541-553 (Oct. 2005).
Palmieri, Diane et al., "Her-2 Overexpression Increases the Metastatic Outgrowth of Breast Cancer Cells in the Brain," Cancer Res., 67(9):4190-4198 (May 1, 2007).
Palmieri, Diane et al., "Brain Metastases of Breast Cancer," *Breast Dis.*, 26:139-147 (2006, 2007).
Palmieri, Diane et al., "Vorinostat Inhibits Brain Metastatic Colonization in a Model of Triple-Negative Breast Cancer and Induces DNA Double-Strand Breaks," *Clin. Cancer Res.*, 15(19):6148-6157 (Oct. 1, 2009).
Pestalozzi, BC et al., "Identifying Breast Cancer Patients at Risk for Central Nervous System (CNS) Metastases in Trials of the International Breast Cancer Study Group (IBCSG)," *Ann. Oncol.*, 17(6):935-944 (Apr. 7, 2006).
Plaza-Menacho, I. et al., "Targeting the Receptor Tyrosine Kinase RET Sensitizes Breast Cancer Cells to Tamoxifen Treatment and Reveals a Role for RET in Endocrine Resistance," *Oncogene*, 29(33):4648-4657 (Aug. 19, 2010).
Porkka, Kimmo et al., "Dasatinib Crosses the Blood-Brain Barrier and is an Efficient Therapy for Central Nervous System Philadelphia Chromosome-Positive Leukemia," *Blood*, 112(4):1005-1012 (Aug. 15, 2008).
Portella, Giuseppe et al., "Development of Mammary and Cutaneous Gland Tumors in Transgenic Mice Carrying the RET/PTC1 Oncogene," *Oncogene*, 13(9):2021-2026 (Nov. 7, 1996).
Ramaswamy, Sridhar et al., "A Molecular Signature of Metastasis in Primary Solid Tumors," *Nature Genet.*, 33(1):49-54 (Jan. 2003).
Rodriguez, A. A. et al., "DNA Repair Signature is Associated with Anthracycline Response in Triple-Negative Breast Cancer Patients," *Breast Cancer Res. Treat.*, 123(1):189-196 (Aug. 2010).
Rosner, Dutzu et al., "Chemotherapy Induces Regression of Brain Metastases in Breast Carcinoma," *Cancer*, 58(4):832-839 (Aug. 15, 1986).
Ryberg, Marianne et al., "Predictors of Central Nervous System Metastasis in Patients with Metastatic Breast Cancer. a Competing Risk Analysis of 579 Patients Treated with Epirubicin-Based Chemotherapy," *Breast Cancer Res. Treat.*, 91(3):217-225 (Jun. 2005).
Ryden, Lisa et al., "Tumor Specific VEGF-A and VEGFR2/KDR Protein are Co-Expressed in Breast Cancer," *Breast Cancer Res. Treat.*, 82(3) :147-154 (Dec. 2003).
Saito, Yoshihito D. et al., "Fyn: a Novel Molecular Target in Cancer," *Cancer*, 116(7):1629-1637 (Apr. 1, 2010).
Schaefer, Carl F. et al., "PID: the Pathway Interaction Database," *Nucl. Acids Res.*, 37:D674-D679 (Jan. 2009).
Shaffrey, Mark E. et al., "Brain Metastases," *Curr. Probl. Surg.*, 41(8):665-741 (Aug. 2004).
Shapira, Ma'anit et al., "The mTOR Inhibitor Rapamycin Down-Regulates the Expression of the Ubiquitin Ligase Subunit Skp2 in Breast Cancer Cells," *Breast Cancer Res.*, 8(4):R46, 9 pages (Jul. 19, 2006).
Shats, Igor et al., "Using a Stem Cell-Based Signature to Guide Therapeutic Selection in Cancer," *Cancer Res.*, 71(5):1772-1780 (Mar. 1, 2011).
Slimane, K et al., "Risk Factors for Brain Relapse in Patients with Metastatic Breast Cancer," *Ann. Oncol.*, 15(11):1640-1644 (Nov. 2004).
Smid, Marcel et al., "Subtypes of Breast Cancer Show Preferential Site of Relapse," *Cancer Res.*, 68(9):3108-3114 (May 2008).
Sneed, Penny K. et al., "A Multi-Institutional Review of Radiosurgery Alone Vs. Radiosurgery with Whole Brain Radiotherapy as the Initial Management of Brain Metastases," *Int. J. Radiat. Oncol. Biol. Phys.*, 53(3):519-526 (Jul. 1, 2002).
Souglakos, John et al., "Central Nervous System Relapse in Patients with Breast Cancer is Associated with Advanced Stages, with the Presence of Circulating Occult Tumor Cells and with the HER2/Neu Status," *Breast Cancer Res.*, 8(4):R36 (Jul. 17, 2006).

(56) References Cited

OTHER PUBLICATIONS

Tham, Yee-Lu et al., "Primary Breast Cancer Phenotypes Associated with Propensity for Central Nervous System Metastases," *Cancer*, 107(4):696-704 (Aug. 15, 2006).

Unger, Kristian et al., "Novel Gene Rearrangements in Transformed Breast Cells Identified by High-Resolution Breakpoint Analysis of Chromosomal Aberrations," *Endocrine-Related Cancer*, 17(1):87-98 (Jan. 29, 2010).

Vandesompele, Jo et al., "Accurate Normalization of Real-Time Quantitative RT-PCR Data by Geometric Averaging of Multiple Internal Control Genes," *Genome Biol.*, 3(7):RESEARCH0034, 12 pages (Jun. 18, 2002).

Wadasadawala, Tabassum et al., "Brain Metastases from Breast Cancer: Management Approach," *J. Cancer Res. Ther.*, 3(3):157-165 (Jul.-Sep. 2007).

Walbert, Tobias, and Gilbert, Mark R., "The Role of Chemotherapy in the Treatment of Patients with Brain Metastases from Solid Tumors," *Int. J. Clin. Oncol.* (Japan Soc. Clin. Oncol.), 14(4):299-306 (Aug. 25, 2009).

Wang, Yixin et al., "Gene-Expression Profiles to Predict Distant Metastasis of Lymph-Node-Negative Primary Breast Cancer," *Lancet*, 365(9460):671-679 (Feb. 19, 2005).

Weigelt, Britta et al., "Gene Expression Profiles of Primary Breast Tumors Maintained in Distant Metastases," *Proc. Natl. Acad.*, 100(26):15901-15905 (Dec. 23, 2003).

Weil, Robert J. et al., "Breast Cancer Metastasis to the Central Nervous System," *Am. J. Pathol.*, 167(4):913-920, (Oct. 2005).

Yadav, Vipin and Denning, Mitchell F., "Fyn is Induced by Ras/PI3K/Akt Signaling and is Required for Enhanced Invasion/Migration," *Molec. Carcinogenesis*, 50(5):346-352 (May 2011).

Yildirim, Muhammed A. et al., "Drug-Target Network," *Nat. Biotechnol.*, 25(10):1119-1126 (Oct. 2007).

Yoneda, Toshiyuki et al., "A Bone-Seeking Clone Exhibits Different Biological Properties from the MDA-MB-231 Parental Human Breast Cancer Cells and a Brain-Seeking Clone In Vivo and In Vitro," *J. Bone Miner. Res.*, 16(8):1486-1495 (Aug. 2001).

Yoshiji, Hitoshi et al., "Expression of Vascular Endothelial Growth Factor, Its Receptor, and Other Angiogenic Factors in Human Breast Cancer," *Cancer Res.*, 56:2013-2016 (May 1, 1996).

Zhao, Hong et al., "The Effect of mTOR Inhibition Alone or Combined with MEK Inhibitors on Brain Metastasis: an In Vivo Analysis in Triple-Negative Breast Cancer Models," Breast Cancer Res. Treat., 131(2):425-436 (Jan. 2012).

Zuercher, W.J. et al., "Current Review of Small Molecule Ret Kinase Inhibitors," *Mini Rev. Med. Chem.*, 10(2):138-146 (Feb. 2010).

\* cited by examiner

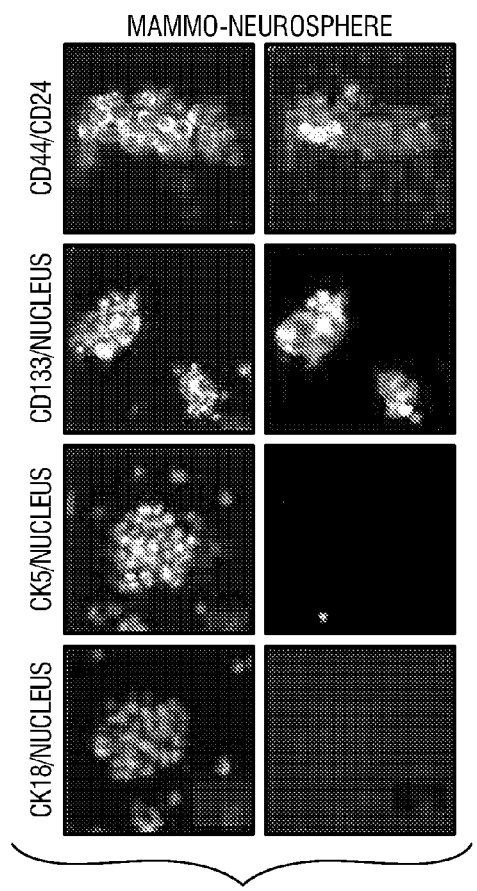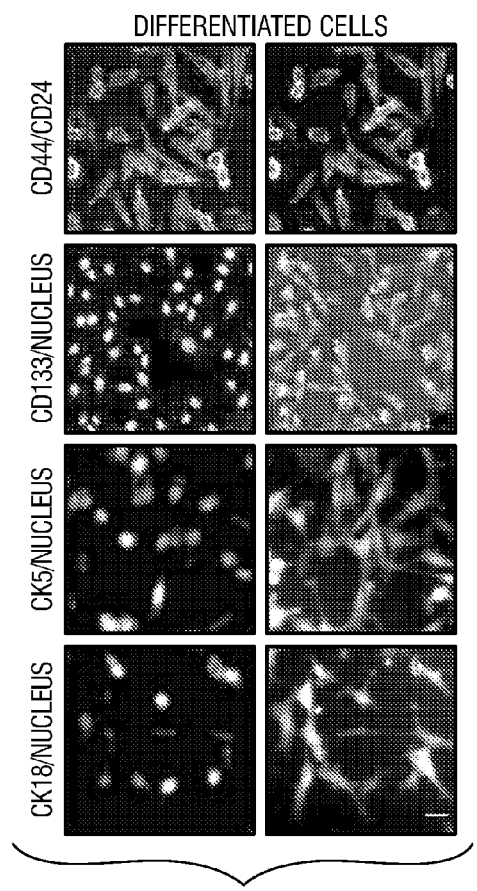
FIG. 5B-1    FIG. 5B-2

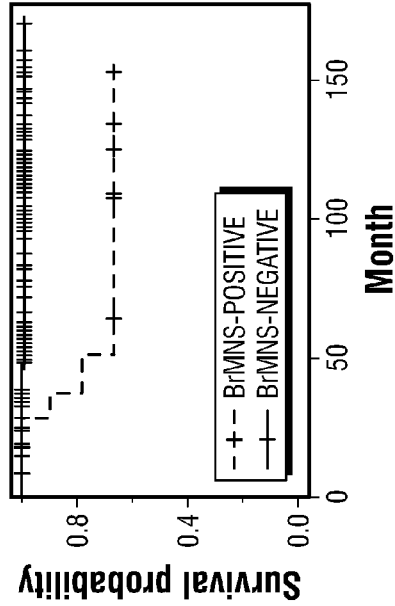
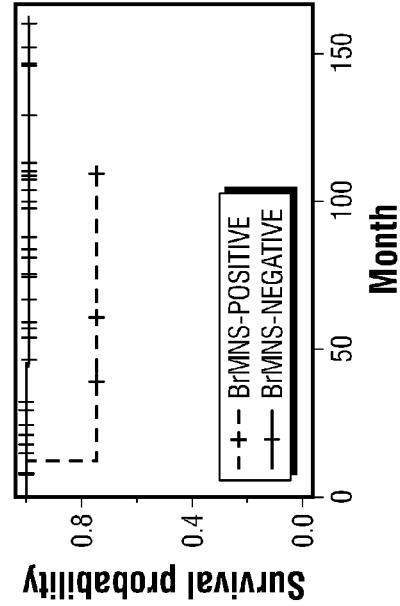
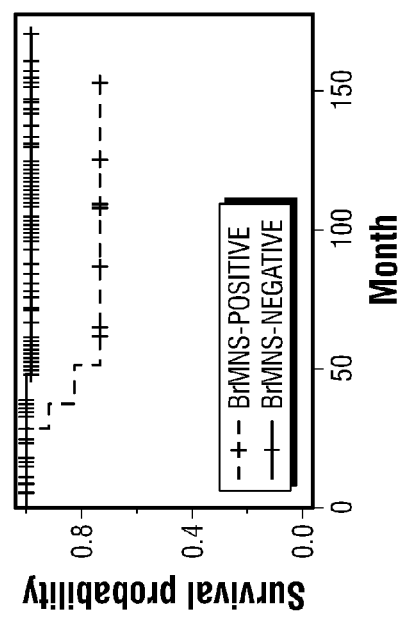
FIG. 6A-1
FIG. 6A-2
FIG. 6A-3
FIG. 6A-4

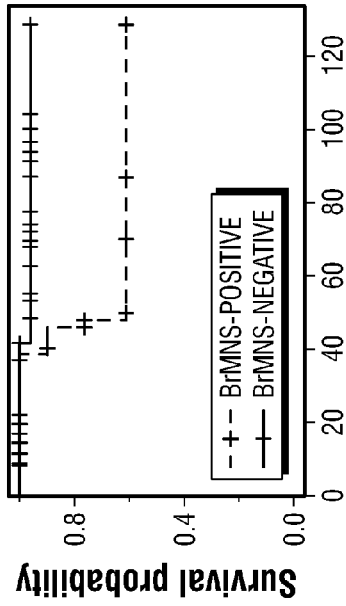
FIG. 6B-1
MSK82
| MARKERS | BrMNS- | BrMNS+ | P-VALUE (FISHER EXACT TEST) |
|---|---|---|---|
| ER- | 13 | 23 | |
| ER+ | 4 | 42 | 0.0049 |
| PR- | 12 | 34 | |
| PR+ | 5 | 31 | 0.06 |
| HER2- | 13 | 51 | |
| HER2+ | 4 | 14 | 1 |
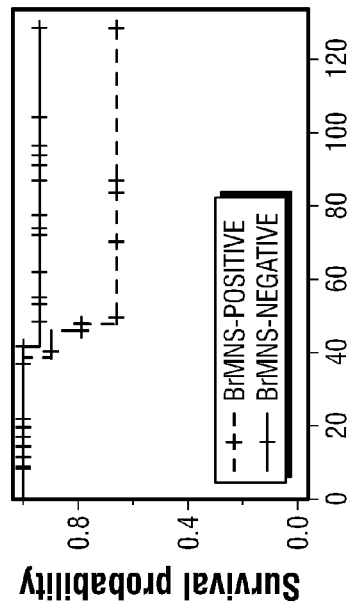
FIG. 6B-2
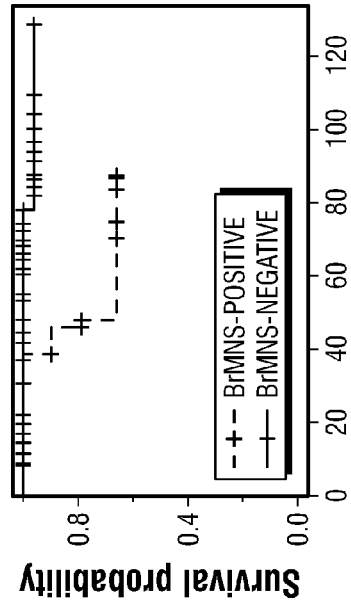
FIG. 6B-3
FIG. 6B-4

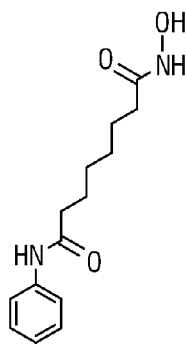

SAHA
MW: 264.3
Predicted LogP: 1.88
Hydrogen bond donors: 3
Hydrogen bond receptor: 5
# of rotatable bonds: 8

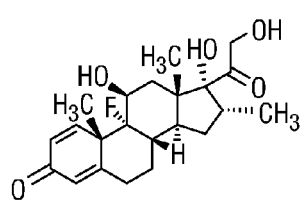

Dexamethasone
MW: 392
Experimental LogP/Hydrophobicity: 1.1
Predicted LogP: 1.93
Hydrogen bond donors: 3
Hydrogen bond receptor: 5
# of rotatable bonds: 2

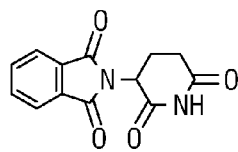

Thalidomide
MW: 258
Experimental LogP/Hydrophobicity: 0.3
Predicted LogP: 0.42
Hydrogen bond donors: 1
Hydrogen bond receptor: 4
# of rotatable bonds: 1

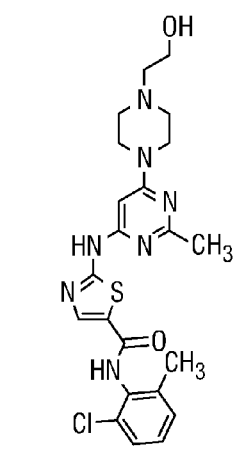

Dasatinib
MW: 488
Experimental LogP/Hydrophobicity: 1.8
Hydrogen bond donors: 3
Hydrogen bond receptor: 8
# of rotatable bonds: 7

*FIG. 7A*

Imatinib
MW: 493
Experimental LogP/Hydrophobicity: 3
Predicted LogP: 3.47
Hydrogen bond donors: 2
Hydrogen bond receptor: 7
# of rotatable bonds: 7

Sofarenib
MW: 465
Experimental LogP/Hydrophobicity: 3.8
Hydrogen bond donors: 3
Hydrogen bond receptor: 3
# of rotatable bonds: 6

Cabozantinib
MW: 501
Predicted ALogP: 4.34
Hydrogen bond donors: 2
Hydrogen bond receptor: 6
# of rotatable bonds: 8

Pazopanib
MW: 437
Predicted ALogP: 3.74
Hydrogen bond donors: 2
Hydrogen bond receptor: 7
# of rotatable bonds: 5

Sunitinib
MW: 398
Experimental LogP/Hydrophobicity: 2.5
Predicted LogP: 3.24
Hydrogen bond donors: 3
Hydrogen bond receptor: 3
# of rotatable bonds: 7

Pranlukast
MW: 481
Predicted LogP: 4.84
Hydrogen bond donors: 2
Hydrogen bond receptor: 7
# of rotatable bonds: 9

MOLECULAR DIAGNOSTIC METHODS FOR PREDICTING BRAIN METASTASIS OF BREAST CANCER

The present application claims priority to U.S. Provisional Patent Application No. 61/386,186, filed Sep. 24, 2010, the contents of which is specifically incorporated herein in its entirety by express reference thereto.

STATEMENT REGARDING FEDERALLY SPONSORED RESEARCH OR DEVELOPMENT

This invention was made with government support under Grant No. CA149196 from the National Institutes of Health. The government has certain rights in the invention.

BACKGROUND OF THE INVENTION

Field of the Invention

The present invention relates to the prognosis of the progression of breast cancer in a patient, and more particularly to the prediction of the occurrence of metastasis in one or more tissue or organ of patients affected with a breast cancer. In particular embodiments, methods are provided for drug repositioning in patients with breast cancer brain metastasis, and for improving patient outcomes. Compositions and diagnostic kits for determining the likelihood of brain metastasis of breast cancer are also provided.

Description of Related Art

Central nervous system (CNS) metastases is the most common type of brain malignancy, and breast cancer is the second most common type of malignancy to cause CNS metastases. The incidence of brain metastases in breast cancer has been reported up to 26-48% in clinical series, and it is expected to continue to rise as we achieve better systemic control of the disease. Brain metastases are associated with poor patient survival and poor quality of life.

Breast cancer is the most common malignant disease among Western women. Unfortunately, it is not the primary tumor, but the occurrence of metastases in distant organs that is the major cause of death for breast cancer patients. In fact, in patients where solid secondary tumors are identified, the long-term survival rate falls from 90% to around 5%. Despite the progress in the development of targeted therapies, approximately 40% of treated patients relapse and ultimately die of metastatic breast cancer.

Malignant breast tumors can invade and damage nearby tissues and organs, and can also metastasize, entering the bloodstream or lymphatic system. When breast cancer cells metastasize outside the breast, they are often found in the lymph nodes under the arm (i.e., the axillary lymph nodes). If the cancer has reached these nodes, it means that cancer cells may have spread to other lymph nodes or other organs, such as bones, liver, brain or lungs. Breast cancer metastasis of various organs also occurs without previous spreading to lymph nodes. Intensive research in recent years has focused on early detection, treatment, and prevention of metastatic breast cancer.

As noted in U.S. Patent Application Publ. No. 20100113297 (specifically incorporated herein in its entirety by express reference thereto), the rational development of preventive, diagnostic and therapeutic strategies for women at risk for breast cancer would be significantly enhanced by a better understanding of the molecular map of the tumorigenic process, but, "relatively little is known of the molecular events that mediate the transition of normal breast cells to the various stages of breast cancer progression. Similarly, little is known of the molecular events that mediate the transition of cells from one stage of breast cancer to another, and finally to metastasis."

The treatment of brain metastases in breast cancer remains challenging. Whole-brain radiation therapy (WBRT) for palliation as a backbone in the management of brain metastasis yields an extended median survival time of only about 3 to 6 months, and often severely impacts the quality of life in those final months. Surgical resection of the tumor prolongs survival only in patients having a single lesion, and a well-controlled systemic disease. The use of stereotactic radiosurgery in combination with WBRT has provided better local control; nevertheless, minimal overall survival benefit is often seen. For drug treatment options, corticosteroids are used to reduce peritumoral edema, and to provide symptomatic relief. The use of systemic chemotherapy and hormonal therapy has been generally disappointing, which is often attributed to the impermeability of the blood-brain barrier (BBB) and the blood-tumor barrier (BTB), and efflux of the drug by P-glycoprotein (Pgp) activity. Unfortunately, there are no approved or widely accepted treatment methods for brain metastases of breast cancer other than the limited aforementioned strategies. What is lacking in the art are methods for accurately predicting the likelihood of brain metastasis of breast cancer, and methods for identifying and/or repositioning known or novel therapeutics for use in the treatment of metastatic breast cancer.

SUMMARY OF THE INVENTION

The present invention overcomes these and other limitation inherent in the prior art by providing a noninvasive molecular diagnostic test that may performed on a tumor biopsy sample. Importantly, this novel method may be performed on a small amount of the tissue that was previously removed from the patient during the original surgical lumpectomy, mastectomy, or core biopsy. Proteins are extracted from the tissue sample, and contacted with a reverse-phase protein microarray chip to determine expression of one or more genetic "markers" that have been identified as diagnostic of the disease.

In particular embodiments, the inventors have identified a unique 31-protein signature, whose presence in the biopsied sample is highly predictive of brain metastasis of breast cancer. Using the results obtained from this molecular analysis of tumor cells, oncologists are now able to determine the likelihood of cancer progression and metastasis, and better formulate a customized treatment plan tailored to the unique genetic characteristics of the particular tumor.

The present invention, in some embodiments thereof, relates to methods and kits for predicting cancer metastasis in a mammalian subject, and more particularly for predicting cancer metastasis of a non-neuronal cancer, such as breast cancer, in a human patient.

In a first embodiment, the invention provides a method of predicting central nervous system (CNS) metastasis of a non-neuronal cancer such as breast cancer in a subject, the method comprising determining the presence of a 31-gene signature within a biological sample taken from cells or tissues of the subject, wherein the identification of the 31-gene signature a is indicative of an increased likelihood of CNS metastasis of the non-neural cancer.

In another aspect, the invention provides a method of predicting central nervous system (CNS) metastasis of a non-neuronal cancer in a subject, the method comprising determining a gene expression level or a protein activity level of a 31-gene signature, in a sample of the subject wherein the presence of each of the 31 signature genes within the sample, and correlating the level to that found in a sample from an unaffected control subject is indicative of the likelihood of CNS metastasis of the non-neural cancer in the subject. Such methods may further optionally include one or more additional steps such as determining the level of gene expression or the activity of the encoded protein includes comparing the subject results to those of a sample from an unaffected individual that does not have metastatic disease is further indicative of the likelihood of CNS metastasis of the non-neural cancer in the subject.

As noted herein, the method generally involves analysis of the 31-gene signature described herein, and determination of the presence of one or more various combinations of at least 5 or more of the following mammalian proteins: growth factor receptor-bound protein 2 (GRB2), KH domain-containing, RNA-binding, signal transduction-associated protein 1 (KHDRBS1), ret proto-oncogene (RET), proto-oncogene tyrosine-protein kinase Fyn (FYN), kinase insert domain receptor (KDR), non-catalytic region of tyrosine kinase adaptor protein 1 (NCK1), WAS/WASL-interacting protein family member 1 (WIPF1), RAF proto-oncogene serine/threonine-protein kinase (c-Raf; RAF1), tyrosine 3-monooxygenase/tryptophan 5-monooxygenase activation protein (YWHAB), mitochondrial ATP synthase subunit alpha (ATP5A1), mitogen-activated protein kinase kinase kinase 3 (MAP3K3), protein transport protein Sec16A (SEC16A), D-3-phosphoglycerate dehydrogenase (PHGDH), inhibitor of nuclear factor kappa-B kinase subunit beta (IKBKB), proto-oncogene c-Rel (REL), NF-kappa-B inhibitor beta (NFKBIB), transcription factor p65 (RELA), A-kinase anchor protein 8-like protein (AKAP8L), rRNA 2'-O-methyltransferase fibrillarin (FBL), Deleted in Breast Cancer 1 protein (KIAA1967), T-complex protein 1 subunit theta (CCT8), Ras GTPase-activating-like protein (IQGAP2), NF-kappa-B p105 subunit (NFKB1), E2F transcription factor 1 (E2F1), methyl-CpG-binding domain protein 1 (MBD1), histone-lysine N-methyltransferase (SUV39H1), filamin-A (FLNA), NF-kappa-B essential modulator (IKBKG), VIM, histone deacetylase 1 (HDAC1), and histone deacetylase 2 (HDAC2).

The invention further provides a method for treating a subject having a non-neuronal cancer, the method that generally includes the steps of: (a) determining a level or an activity of each of a 31-node network signature that comprises the following mammalian proteins: growth factor receptor-bound protein 2 (GRB2), KH domain-containing, RNA-binding, signal transduction-associated protein 1 (KHDRBS1), ret proto-oncogene (RET), proto-oncogene tyrosine-protein kinase Fyn (FYN), kinase insert domain receptor (KDR), non-catalytic region of tyrosine kinase adaptor protein 1 (NCK1), WAS/WASL-interacting protein family member 1 (WIPF1), RAF proto-oncogene serine/threonine-protein kinase (c-Raf; RAF1), tyrosine 3-monooxygenase/tryptophan 5-monooxygenase activation protein (YWHAB), mitochondrial ATP synthase subunit alpha (ATP5A1), mitogen-activated protein kinase kinase kinase 3 (MAP3K3), protein transport protein Sec16A (SEC16A), D-3-phosphoglycerate dehydrogenase (PHGDH), inhibitor of nuclear factor kappa-B kinase subunit beta (IKBKB), proto-oncogene c-Rel (REL), NF-kappa-B inhibitor beta (NFKBIB), transcription factor p65 (RELA), A-kinase anchor protein 8-like protein (AKAP8L), rRNA 2'-O-methyltransferase fibrillarin (FBL), Deleted in Breast Cancer 1 protein (KIAA1967), T-complex protein 1 subunit theta (CCT8), Ras GTPase-activating-like protein (IQGAP2), NF-kappa-B p105 subunit (NFKB1), E2F transcription factor 1 (E2F1), methyl-CpG-binding domain protein 1 (MBD1), histone-lysine N-methyltransferase (SUV39H1), filamin-A (FLNA), NF-kappa-B essential modulator (IKBKG), VIM, histone deacetylase 1 (HDAC1), and histone deacetylase 2 (HDAC2) in a sample of the subject; and (b) determining a treatment regimen based on the level or activity of each of the proteins in the 31-node network.

Such methods may further optionally include the additional steps of determining a level and or activity of at least one additional markers involved in cell proliferation and mitosis, wherein an increase in the additional marker is further indicative of CNS metastasis of the neuronal cancer. Exemplary additional marker include, without limitation, one or more oncogenes, transcription factors, growth factors, cancer markers, kinases, or one or more proteins such as KIFC1 (kinesin family member C1), KIF2C (kinesin family member 2C), KIF14 (kinesin family member 14), CCNB2 (cyclin B2), SIL (SCL-TAL1 interrupting locus), TNPO1 (transportin I), and any combinations thereof.

Exemplary treatment regimens include, without limitation, one or more of CNS radiotherapy, intrathecal chemotherapy, intravenous chemotherapy, and any combination thereof, and may include a previously unknown drug, or a therapy not previously identified as being useful in the treatment of brain metastatic breast cancer. Exemplary repositioned drugs identified using the 31-gene signature of brain metastasis of breast cancer include, without limitation, dasatinib or sunitinib.

The invention also provides a method for determining brain metastatic potential in breast cancer patients. Such method generally includes at least the steps of obtaining a sample from an individual, identifying one or more marker-derived polynucleotides from the sample, using a detection mechanism to search for one or more positive matches of the polynucleotides and the markers in Table 3, and developing a quantitative expression profile based on the results obtained therefrom. Such method may further include the optional step of evaluating the quantitative expression profile using one or more risk analyses, wherein the one or more risk analyses includes a statistical model or machine-learning algorithm. Such methods may also further optionally include the step of placing an individual in two or more categories, with such categories including, without limitation, "high risk", "higher risk" "average risk," "intermediate risk, "lower risk," "low risk," etc. based on the statistical model or machine-learning algorithm. In certain applications, the risk analysis may include one or more linear discriminate analyses, or assessing one or more clinico-pathologic variables, or any combination thereof.

The invention also provides a diagnostic kit for predicting CNS metastasis of a non-neuronal cancer in a subject, which generally includes at least one agent for specifically determining the level of gene expression or activity of the encoded protein products of one or more of the genes or gene products in the identified 31-gene signature. Exemplary kits can include one or more gene chips, protein microarrays, and the like.

The kit optionally further includes instructions for screening a drug library to identify a therapeutic agent for treating the non-neuronal cancer in the subject, and may optionally include one or more reagents for specifically determining a level of gene expression, or an activity of at least one protein product selected from the group consisting of an oncogene, a protein kinase, a transcription factor, an anchor protein, a transport protein, a mitochondrial protein, an activation protein, and an inhibitor.

In particular embodiments, the kit is adapted and configured for prediction of brain metastasis of breast cancer in a human, and may further include one or more instructions of reagents adapted and configured for determining a level and or activity of at least one additional marker involved in cell proliferation and mitosis, wherein an increase in the additional marker is further indicative of CNS metastasis of the neuronal cancer.

According to another aspect of certain embodiments of the present invention there is provided a kit for predicting CNS metastasis of a non-neuronal cancer in a subject, the kit comprising a packaging material that comprises at least one agent for specifically determining the presence of, or identifying the expression level and/or activity of each of thirty-one distinct genomic markers (set forth herein in Table 3), wherein the presence of the 31-gene signature is indicative of an increased likelihood of metastasis of a breast cancer to the brain of the subject being tested are preferably one or more of the mammalian proteins set forth and described in Table 3, which include, without limitation, growth factor receptor-bound protein 2 (GRB2), KH domain-containing, RNA-binding, signal transduction-associated protein 1 (KHDRBS1), ret proto-oncogene (RET), proto-oncogene tyrosine-protein kinase Fyn (FYN), kinase insert domain receptor (KDR), non-catalytic region of tyrosine kinase adaptor protein 1 (NCK1), WAS/WASL-interacting protein family member 1 (WIPF1), RAF proto-oncogene serine/threonine-protein kinase (c-Raf; RAF1), tyrosine 3-monooxygenase/tryptophan 5-monooxygenase activation protein (YWHAB), mitochondrial ATP synthase subunit alpha (ATP5A1), mitogen-activated protein kinase kinase kinase 3 (MAP3K3), protein transport protein Sec16A (SEC16A), D-3-phosphoglycerate dehydrogenase (PHGDH), inhibitor of nuclear factor kappa-B kinase subunit beta (IKBKB), proto-oncogene c-Rel (REL), NF-kappa-B inhibitor beta (NFKBIB), transcription factor p65 (RELA), A-kinase anchor protein 8-like protein (AKAP8L), rRNA 2'-O-methyltransferase fibrillarin (FBL), Deleted in Breast Cancer 1 protein (KIAA1967), T-complex protein 1 subunit theta (CCT8), Ras GTPase-activating-like protein (IQGAP2), NF-kappa-B p105 subunit (NFKB1), E2F transcription factor 1 (E2F1), methyl-CpG-binding domain protein 1 (MBD1), histone-lysine N-methyltransferase (SUV39H1), filamin-A (FLNA), NF-kappa-B essential modulator (IKBKG), VIM, histone deacetylase 1 (HDAC1), and histone deacetylase 2 (HDAC2).

In exemplary embodiments, the thirty-one genomic markers that comprise the signature are preferably one or more of the mammalian proteins set forth and described in Table 3, which include, without limitation, growth factor receptor-bound protein 2 (GRB2), KH domain-containing, RNA-binding, signal transduction-associated protein 1 (KHDRBS1), ret proto-oncogene (RET), proto-oncogene tyrosine-protein kinase Fyn (FYN), kinase insert domain receptor (KDR), non-catalytic region of tyrosine kinase adaptor protein 1 (NCK1), WAS/WASL-interacting protein family member 1 (WIPF1), RAF proto-oncogene serine/threonine-protein kinase (c-Raf; RAF1), tyrosine 3-monooxygenase/tryptophan 5-monooxygenase activation protein (YWHAB), mitochondrial ATP synthase subunit alpha (ATP5A1), mitogen-activated protein kinase kinase kinase 3 (MAP3K3), protein transport protein Sec16A (SEC16A), D-3-phosphoglycerate dehydrogenase (PHGDH), inhibitor of nuclear factor kappa-B kinase subunit beta (IKBKB), proto-oncogene c-Rel (REL), NF-kappa-B inhibitor beta (NFKBIB), transcription factor p65 (RELA), A-kinase anchor protein 8-like protein (AKAP8L), rRNA 2'-O-methyltransferase fibrillarin (FBL), Deleted in Breast Cancer 1 protein (KIAA1967), T-complex protein 1 subunit theta (CCT8), Ras GTPase-activating-like protein (IQGAP2), NF-kappa-B p105 subunit (NFKB1), E2F transcription factor 1 (E2F1), methyl-CpG-binding domain protein 1 (MBD1), histone-lysine N-methyltransferase (SUV39H1), filamin-A (FLNA), NF-kappa-B essential modulator (IKBKG), vimentin (VIM), histone deacetylase 1 (HDAC1), and histone deacetylase 2 (HDAC2).

According to some embodiments of the invention, the kit further comprises one or more agents for specifically determining a level and/or activity of each of one or more genes, or their translated protein products, selected from the group consisting of growth factor receptor-bound protein 2 (GRB2), KH domain-containing, RNA-binding, signal transduction-associated protein 1 (KHDRBS1), ret proto-oncogene (RET), proto-oncogene tyrosine-protein kinase Fyn (FYN), kinase insert domain receptor (KDR), non-catalytic region of tyrosine kinase adaptor protein 1 (NCK1), WAS/WASL-interacting protein family member 1 (WIPF1), RAF proto-oncogene serine/threonine-protein kinase (c-Raf; RAF1), tyrosine 3-monooxygenase/tryptophan 5-monooxygenase activation protein (YWHAB), mitochondrial ATP synthase subunit alpha (ATP5A1), mitogen-activated protein kinase kinase kinase 3 (MAP3K3), protein transport protein Sec16A (SEC16A), D-3-phosphoglycerate dehydrogenase (PHGDH), inhibitor of nuclear factor kappa-B kinase subunit beta (IKBKB), proto-oncogene c-Rel (REL), NF-kappa-B inhibitor beta (NFKBIB), transcription factor p65 (RELA), A-kinase anchor protein 8-like protein (AKAP8L), rRNA 2'-O-methyltransferase fibrillarin (FBL), Deleted in Breast Cancer 1 protein (KIAA1967), T-complex protein 1 subunit theta (CCT8), Ras GTPase-activating-like protein (IQGAP2), NF-kappa-B p105 subunit (NFKB1), E2F transcription factor 1 (E2F1), methyl-CpG-binding domain protein 1 (MBD1), histone-lysine N-methyltransferase (SUV39H1), filamin-A (FLNA), NF-kappa-B essential modulator (IKBKG), VIM, histone deacetylase 1 (HDAC1), and histone deacetylase 2 (HDAC2). In particular applications of the present method, each of the 31 markers denoted herein will be examined and their levels evaluated in the cells or tissues of a mammalian patient at risk for developing one or more brain metastases of breast cancer.

The molecular assays described herein for specifically predicting brain metastasis will provide clinicians for the first time a molecular diagnostic tool to facilitate individualized patient-specific therapeutic regimens to more effectively treat brain metastatic breast cancer. The results afforded by the present methods will assist physicians in selecting existing blood-brain barrier-penetrating chemotherapeutics, identifying new uses for existing compounds, and conceiving entirely new classes of drugs that may be used to effectively target the particular type of breast cancer in individual patients.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 1A shows Cyto and pathway location (Add GO). Shown are Kaplan-Meier curves and p values for brain metastasis-free survival on the basis of BCBM-GNS status in three independent cohorts breast tumors; FIG. 1B EMC $^-$192, p=0.000147; FIG. 1C EMC −286 (EMC −192), p=6.75e $^-$07; and FIG. 1D EMC $^-$82 (EMC $^-$286 (EMC $^-$192)), p=0.00851;

FIG. 2B and FIG. 2C show in vitro BBB transmigration activity of the indicated cell lines and conditions. The number of transmigrated cells relative to the parental cell lines is plotted. N=12, p-value were calculated by one-tailed unpaired t-test. FIG. 2B shows Invasion siRNA and FIG. 2C shows a western immunoblot analysis of RET, FYN, β-actin, and KDR in the indicated cell lines and sh RNAs knockdown cell lines. FIG. 2D, FIG. 2E, and FIG. 2F shows the in vitro invasion activity of the indicated cell lines treated by different concentrations of sunitinib and dasatinib. The number of invased cells relative to the parental cell lines is plotted. N=12 p values were calculated by one-tailed unpaired t-test. FIG. 2E and FIG. 2F show the expression of down-stream pathway proteins under the treatment of sunitinib and dasatinib at indicated concentrations;

FIG. 3A-1, FIG. 3A-2, FIG. 3B-1, FIG. 3B-2, FIG. 3C, FIG. 3D-1, and FIG. 3D-2 show immunohistochemistry staining for the brain sections of the animals receiving sunitinib and dasatinib or vehicle treatment (FIG. 3A-1 and FIG. 3A-2); Sunitinib and dasatinib inhibit brain metastasis in two 231-BR models examined by ex vivo whole brain imaging; sunitinib inhibits p-RET, dasatinib inhibits p-FYN (FIG. 3B-1 and FIG. 3B-2) and H&E staining on whole brain sections (FIG. 3C). FIG. 3D-1 and FIG. 3D-2 shows sunitinib and dasatinib inhibit brain metastasis in two 231-BR models examined by GFP western immunoblot on whole brain lysates of the animals. HC: 231-BR-HER2 animal treated with vehicle, HSL: 231-BR-HER2 animal treated low dose of Sunitinib 40 mg/kg; HSH: 231-BR-Her2 animal treated high dose of Sunitinib 80 mg/kg: VC: 231-BR-vector animal treated with vehicle; VSL: 231-BR-vector animal treated low dose of Sunitinib 40 mg/kg; VSH: 231-BR-vector animal treated high dose of Sunitinib 80 mg/kg; *P<0.05 vs HC; ^p<0.05 vs VC.

FIG. 4A-1, FIG. 4A-2, FIG. 4A-3, FIG. 4A-4, FIG. 4B-1, FIG. 4B-2, FIG. 4B-3, and FIG. 4B-4 show sunitinib inhibits perivascular invasion (FIG. 4A-1 and FIG. 4A-2) and proliferation of tumor cells in two 231-BR models examined by immunohistochemistry of CD31 and Ki67 staining. *P<0.05 vs VC; ^p<0.05 vs. HC; (FIG. 4B-2, FIG. 4B-2, FIG. 4B-3, and FIG. 4B-4) dasatinib inhibit perivascular invasion and proliferation of tumor cells in two 231-BR models examined by immunohistochemistry of CD31 and Ki67 staining. *P<0.05 vs VC; ^p 0.05 vs HC;

FIG. 5A-1. FIG. 5A-2, FIG. 5B-1 FIG. 5B-2, FIG. 5C, and FIG. 5D demonstrate that sunitinib and dasatinib inhibit the mammo-neurosphere formation. These figures show characterization of the mammoneurospheres derived from brain metastatic loci of the 231-BR animal model. Mammospheres were cultured from the mouse mammary gland xenograft tumor by isotopic injection of 231-parental cells. Neurospheres were cultured from the hippocampus of embryonic mouse (FIG. 5A-1 and FIG. 5A-2); FIG. 5B-1 and FIG. 5B-2 show the mammoneurospheres where disrupted and the cells plated onto glass coverslips in medium supplemented with 1% fetal calf serum. After 10 days of adherent culture, the cells were stained with antibodies to CD44, CD24, CD133, CK5 and CK18; FIG. 5C and FIG. 5D show the mammo-neurosphere formation efficiency after treatment of xenograft tumors in vivo. 231-BR xenograft tumors were either left untreated, or were treated with sunitinib or dasatinib and mammo-neurosphere formation evaluated 14 days after treated. FIG. 5D shows Kaplan-Meier curves and p values for brain metastasis-free survival of the animals being transplanted with mammoneurosphere-dissociated cells ($1.75 \times 10^5$) after drug treatment in vitro for 48 hours.

FIG. 6A-1, FIG. 6A-2, FIG. 6A-3, FIG. 6A-4, FIG. 6A-5, FIG. 6A-6, and FIG. 6A-7 show the relationship between BCBN-GN, ER (ER+, p=7.49e-06 and ER−, p=0.000714), PR (PR=, p=3.07e-09 and PR−, p=0.00256) and HER2 (HER2=, p=0.00137 and HER2−, p=9.26e-08) status in EMC286 breast tumors. P value for the indicated comparison calculated by Fisher's exact test (FIG. 6A-1);

FIG. 6B-1, FIG. 6B-2, FIG. 6B-3, and FIG. 6B-4 show relationship between BCBN-GN, ER (ER−, p=0.0847), PR(PR−, p=0.00994) and Her2 (HER2−, p=0.00131) status in MSK82 breast tumors. P value for the indicated comparison calculated by Fisher's exact test (FIG. 6B-1);

FIG. 6C-1, FIG. 6C-2, FIG. 6C-3 and FIG. 6C-4 show the relationship between BCBN-GN, ER (ER, p=0.0001), PR(PR, p=0.0009) and Her2 (HER2, p=0.0005) status in EMC192 breast tumors. P value for the indicated comparison calculated by Fisher's exact test (FIG. 6C-1);

FIG. 7A, FIG. 7B, and FIG. 7C show the chemical structures for the candidate drugs and parameters for the "Rule of Five;"

FIG. 9A-1, FIG. 9A-2, FIG. 9A3, FIG. 9A-4, FIG. 9A-5, FIG. 9A-6, FIG. 9B and FIG. 9C show the plasma and brain distribution of sunitinib and dasatinib in the xenograft animal models (FIG. 9A-1, FIG. 9A-2, FIG. 9A-3, FIG. 9A-4, FIG. 9A-5 and FIG. 9A-6); FIG. 9B shows the chromatograms of dasatinib and testosterone for authentic plasma sample 6-hr post last-dose; FIG. 9C shows the chromatograms of sunitinib and testosterone for authentic mouse plasma sample 6-hr post last dose.

DESCRIPTION OF ILLUSTRATIVE EMBODIMENTS

Figure 1A:
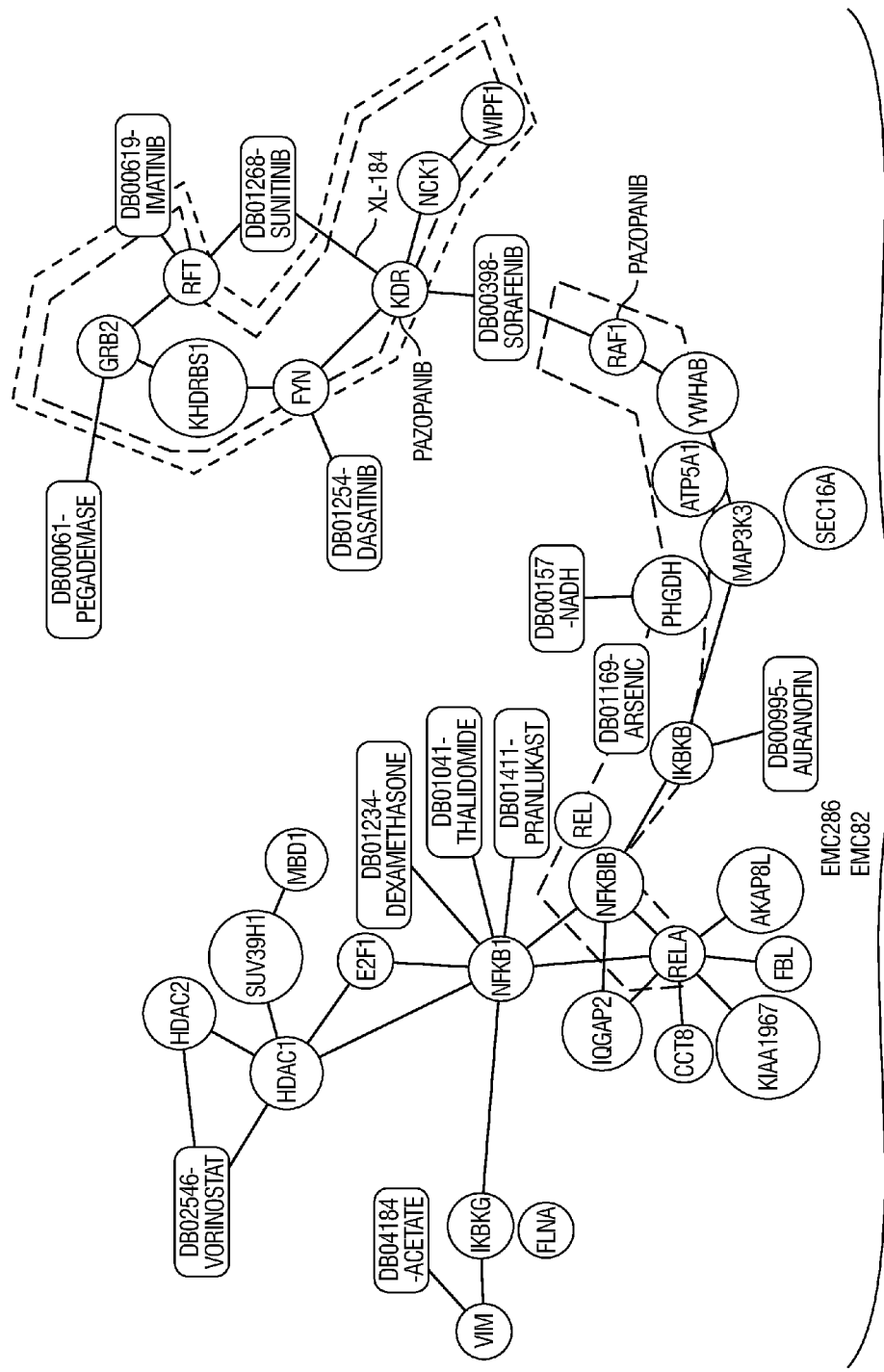
FIG. 1A, FIG. 1B, FIG. 1C and FIG. 1D show a 31-gene network signature derived from total 612 primary breast tumor microarrays and the mapped targeted drugs from brain metastasis of breast cancer.
Figure 1B:
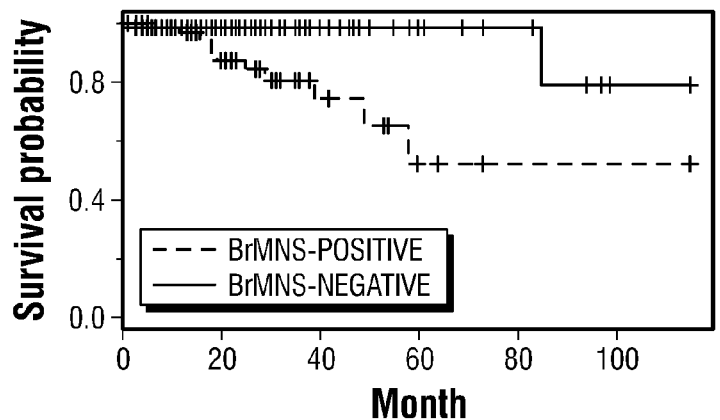
Figure 1C:
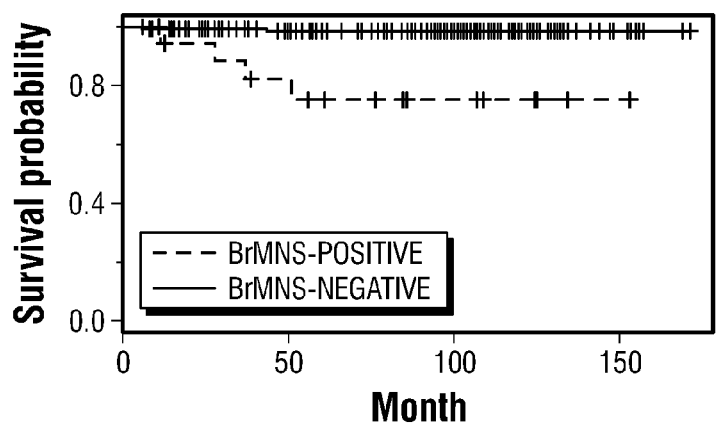
Figure 1D:
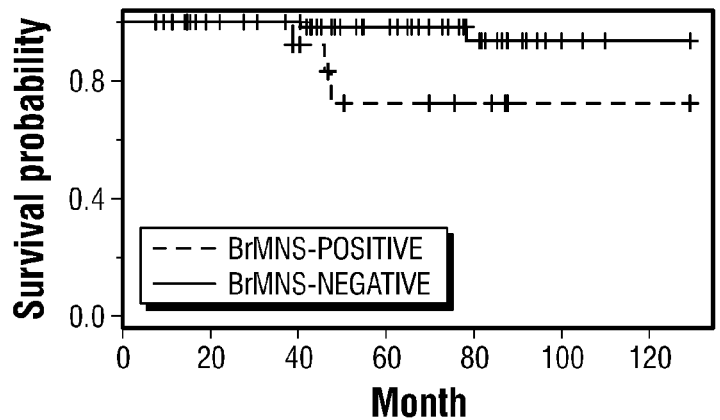

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Brain Metastases in Breast Cancer

The incidence of brain metastases in breast cancer has been reported up to 26-48% in clinical series (Palmieri et al., 2006). It is expected to continue to rise in the incidence as better systemic control of the disease is achieved, and brain is a sanctuary site for the tumor cells (Ono et al., 2009; Narita and Shibui, 2009; Walbert and Gilbert, 2009). Brain metastases are associated with poor patient survival, with a median survival of four months after diagnosis of the metastases, and poor quality of life (Weil et al., 2005; Ryberg et al., 2005). Treatment for brain metastases of breast cancer is designated an unmet medical need by the U.S. Food and Drug Administration. While advances have been made in the treatment of early breast cancer, and there have been modest steps forward in controlling distant metastases in organs other than the brain, almost no progress has been made in the treatment, prevention, or eradication of metastases to the brain. Surgery and radiation, the mainstays of treatment, have remained unchanged for decades. The blood-brain barrier serves as an obstacle to many breast cancer therapies (including conventional chemotherapy and Herceptin), making the urgency of this problem apparent.

Women whose lives are being extended by chemotherapy and targeted therapies such as Herceptin are now more likely to die of brain metastases (Burstein et al., 2005; Gabos et al., 2006; Duchnowska and Szczylik, 2005). Researchers estimate that as many as a quarter to a third of women with metastatic breast cancer will develop brain metastases at some stage of their disease.

Many investigators have sought to identify molecular correlates of tissue tropism in cancer cells. In one approach, central nervous system (CNS) tropism was engineered by in vivo selection of CNS-homing cells from a human breast cancer cell line and from patient-derived breast cancer cells (Bos et al., 2009). Comparative gene expression array of parental and CNS tropic cells identified seventeen genes correlated with CNS tropism. Others have investigated proteins as predictors of CNS metastases, either by protein expression arrays or by targeted antibody assessment of candidate proteins (Gaedcke et al., 2007; Kennecke et al., 2010; Martin et al., 2008). The interesting targets identified through these studies for molecular associated therapies include cyclooxygenase 2,α-2,6-sialyltransferase ST6GALNAC5 and HSP27 (Bos et al., 2009; Martin et al., 2008). In an example of the value of genetic information, a collaborative team was able to identify fifty-one genes that were over-expressed in patients with breast cancer who were more likely to have brain metastases (Klein et al., 2009). Although some advocate prophylactic treatment of patients with these genetic profiles, a more sophisticated and prudent method would be the development of inhibitors and/or modulators of the enzymes or proteins encodes by these genes. This process is, however, costly and time-consuming.

Although molecular tests such as Oncotype DX®, a 21-gene RT-PCR assay that quantifies the likelihood of disease recurrence in women with early-stage breast cancer, and assesses the likely benefit from certain types of chemotherapy, are available to, currently, there are no diagnostics tests available to accurately predict metastasis of breast cancer, and brain metastasis of breast cancer in particular. Diagnostics such as MammaPrint®, a 70-gene microarray test, are available that assess the risk that a breast tumor will spread to other parts of the body, but they, too, are unable to accurately predict brain metastasis of breast cancer.

Tumor cells are believed to pose preferential ability to colonize in certain organs. Till recently, molecular factors that may contribute to organ-specific metastasis of breast cancer to the brain have been identified by experiment human breast cancer carcinoma cell line. However, the emerging of newly opened ~50 breast cancer brain metastasis datasets including gene expression microarray data as well as the clinical annotation, would enable one to have a better systems and integrative understanding of the nature of breast cancer brain metastases by a de novo systems approach, and more imperative to develop effective regimens to prevent and control this aggressive stage of the disease.

The present computational systems biology study revealed that the protein network motifs are enriched in cancer signaling pathways and are important in studying cancer drug targets, treatment response genes, and cancer-related mutated genes. A preliminary network signature was identified with 101 gene nodes from network motifs via the comparative analysis for the Affymetrix HGU133A genome microarray data of 11 primary breast cancers with brain metastasis and 41 primary breast cancers relapsed at other anatomical sites. The short paths composed by the 101 genes can classify the brain metastasis patients from non-brain metastasis patients with 96.43% accuracy. Furthermore, by conducting a univariate analysis in an independent cohort of 192 clinically annotated breast tumors (EMC-192 sets), the inventors validated and narrowed the defining network signature first down to a subset of 31 genes (listed in Table 3), whose overall expression score was associated with brain relapse ($P<0.05$). A core interventional signaling network for breast cancer brain metastasis was then constructed based upon these results, from which predictive analysis of the aggressiveness or likelihood of brain metastasis of the identified tumor type using a facile, molecular diagnostic is made possible for the first time.

While the constructed network has utility in identifying and/or developing new drugs, one important focus of the present invention was using such a network for repositioning of existing known therapeutics to achieve faster translational impact. As evidence of this new utility, nine CNS drug candidates were identified via the targets in the network, and which were also consistent with conventional "Rule of Five" chemical structure analysis. The efficacy of these repositioned drugs was confirmed by their preventing the metastatic colonization of brain by a brain-seeking derivative of the MDA-MB-231 human breast carcinoma cell line (i.e., 231-BR cells). Using the molecular signatures identified in the present invention, two FDA-approved drugs sunitinib and dasatinib [identified via the known targets FLK1 (vascular endothelial growth factor receptor, VEGF-R), RET (proto-oncogene tyrosine-protein kinase receptor ret), and FYN (proto-oncogene tyrosine-protein kinase Fyn)] were repositioned in the network signature, with the ability of penetrating BBB (blood-brain barrier) as well, on a preclinical murine model of the disease.

Sunitinib has previously been approved for the treatment of patients with advanced or metastatic renal cell carcinoma (RCC) and/or metastatic malignant gastrointestinal stromal tumors. Just recently, it has been reported that the efficacy result of sunitinib on RCC brain metastasis was encouraging in the expanded-access trial of sunitinib for 4,564 patients with metastatic RCC and bad-performance status or poor prognosis clinical status. Dasatinib, a second-generation TKI approved for use in imatinib-resistant chronic myelogenous leukemia, also shows promise for glioblastoma therapy. Prior to the present invention, neither of these two drugs, however, had been tested for pre-clinical or clinical efficacy against breast tumors with brain metastasis. Their identification in the present methods as exemplary repositionable drugs, suggests wide applicability of the disclosed network signature-oriented methods.

Network Signature Orientated Drug Repositioning

Mapping key signaling molecules in biochemical pathways is central to drug discovery efforts. The pathways that drive brain metastasis of breast tumors are still poorly understood. Once they have been elucidated, targeted agents can then be developed. However, even the signal transduction can be partly explicated, there still exists a key challenge: the key pathway components will have to be validated as potential druggable targets. Thus, the present strategy for the breast cancer brain metastasis drug reposition was to first identify a signaling network signature that explicitly reveals cause-effect relationship between targets and pathways of interests and then to map approved drugs for the druggable targets in the newly constructed brain metastasis signaling network.

Identifying and Validating the Signaling Network Signature for Breast Cancer Brain Metastasis First, based on filtered PPIs and available signaling pathways, it was shown that a special interacting pattern, i.e., a network motif, plays a key role in cellular signal transduction, and especially, network motifs that are clustered among cancer signaling pathways attract more drugs (FDA approved drugs and anti-neoplastic drugs, etc.) targeting on their proteins than the random selected proteins. Second, based on identified clustering network topology, selected signaling pathways ('MAPK', 'ErbB', 'Wnt', 'Notch', 'VEGF', 'Cell Cycle', and 'P53'), and microarray data for breast cancer (11 brain metastasis patients and 41 non-brain-metastasis patients), a computational model was constructed that can derive those critical molecule-paths with differentially expressed genes passing through at least two signaling pathways. Because the selected molecule-paths share some important genes, for example, 'TP53', 'IKBKB', 'MAP3K3', and 'RELA', they could be merged into a whole signal transduction network or mapping. This molecular mapping involved not only essential signaling molecules and their interactions among different signaling pathways, but also included important differential genes from microarray expressions. 101 gene nodes were identified in the initial network, with the gene paths being able to classify metastasis patients with 96.43% accuracy.

Because the datasets of 52 Affymetrix expression profiles used for discovery of molecular networks was deemed too small to provide the desired confidence interval, the inventors chose to perform a univariate analysis in an independent cohort of 192 clinically annotated breast tumors (EMC-192 sets). The resulting network signature was validated, and narrowed to only 31 genes (shown in Table 3), whose overall expression score was associated with brain relapse (P<0.05). A core intervention signaling network for breast cancer brain metastasis was then constructed from the 31-gene signature, and these data were then used to reposition two FDA-approved molecules not previously implicated in the treatment of brain metastatic breast cancer.

Evaluating Drug Efficacy on Brain Metastasis Breast Cancer Animal Models

Two mouse xenograft models of brain metastasis, generated by transfecting HER2-overexpressing 231-BR brain-seeking breast cancer cells with an EGFP expression vector that contained or lacked the HER2 cDNA, may be used to examine the in vitro and in vivo effects of the repositioned candidate drugs. By left ventricle injection of $1.75 \times 10^5$ cells in 0.1 mL PBS to the female BALB/c nude mice (5-7 weeks old; Charles River Laboratories, Wilmington, Mass., USA), multiple brain metastases were examined at 15-30 days after the injection by GFP fluorescence imaging and H&E staining. Both the 231-BR-HER2 and 231-BR-vector cell lines showed 100% brain metastatic activity. In vitro, sunitinib malate (previously "SU11248", Sutent®, Pfizer Oncology, New York, N.Y., USA), was shown to inhibit the cell proliferation, migration, invasion and mammosphere form efficiency in 231-BR cells (both with and without HER2). Importantly, the initial in vivo study demonstrated that the number of metastasis loci in the sunitinib-treated group was less than in the vehicle-treated group as determined by whole-brain and quarterly-sliced brain GFP imaging.

A total of 240 female BALB/c nude mice were used in a study designed to test the two repositioned drugs. In the study, mice (n=20 mice per group) are left-ventricle injected with 231-BR-vector or 231-BR-HER2 cells, then treated with either sunitinib (40 or 80 mg/kg) or dasatinib (Sprycel®, Bristol-Myers Squibb, Princeton, N.J., USA) (50 or 150 mg/kg) and vehicle 4 days after cell injection, once daily by oral gavage till the euthanasia. Mice are then euthanized by $CO_2$ asphyxiation when they show signs of neurological impairment. The whole brain is then removed from the skull and subjected to GFP fluorescent imaging to detect the presence of the injected 231-BR by the Maestro 420 In Vivo Spectral Imaging System (Cambridge Research and Instrumentation/Caliper Life Sciences, Hopkinton, Mass., USA), and use the data processing software (Nuance Technology) to distinguish or unmix images of fluorescence from multiple sources. After fluorescence imaging, brain sections (10 µm thick) are serially cut and one section every 50 µm will be stained with H&E, and the immunohistochemistry for CD34, VEGF-R, cRET and FYN performed according to standard procedures. The whole slide montage image is then acquired by Olympus IX81 automatic microscope, and InForm software (Cambridge Research and Instrumentation/Caliper Life Sciences) is used for the segmentation and intensity analysis.

Analysis of variance (ANOVA) is deployed for analyzing experimental data. Each group of data was examined about their normality with the Shapiro-Wilk test, and then Bartlett's test was employed to test multi-group's homogeneity of variance; if the p value was significant in the ANOVA test, then a T-test was employed to analyze the significant changed groups. For the in vivo mouse studies, data was pooled from two experiments and a oneway ANOVA was performed for each animal model and cell line model, and drug dose specified as the factor.

Exemplary Definitions

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range. The term "e.g.," as used herein, is used merely by way of example, without limitation intended, and should not be construed as referring only those items explicitly enumerated in the specification. In accordance with long standing patent law convention, the words "a" and "an" when used in this application, including the claims, denotes "one or more."

EXAMPLES

The following examples are included to demonstrate illustrative embodiments of the invention. It should be appreciated by those of ordinary skill in the art that the techniques disclosed in these examples represent techniques discovered to function well in the practice of the invention, and thus can be considered to constitute preferred modes for its practice. However, those of ordinary skill in the art should, in light of the present disclosure appreciate that many changes can be made in the specific embodiments which are disclosed and still obtain a like or similar result without departing from the spirit and scope of the invention.

Example 1

Strategy of Drug Repositioning for Breast Cancer Brain Metastasis

In addition to the general requirements of tumor cells metastasize to distant organs, it is believed that tumor cells poses preferential ability to colonize in certain organs. Molecular factors that may contribute to organ-specific metastasis of breast cancer to the lung, bone and brain have been identified by experimental studies from the Messague lab, from lung-, bone- and brain-colonizing variants of a human breast cancer carcinoma cell line. These advances, along with more and more public available clinically annotated breast tumors data, open up new vistas for developing de novo systems approach to have a better systems biology understanding of the nature of breast cancer cells that cause brain metastases, and more imperative to develop effective regimens to prevent and control this stage of the disease.

The present systems bioinformatics study revealed that the network motifs of protein are enriched in cancer signaling pathways, and are important in studying cancer drug targets, treatment response genes, and cancer-related mutated genes. A first network signature was subsequently identified with 101 genes from network motifs via the comparative analysis for our Affymetrix HGU133A genome microarray data of 11 primary breast cancers with brain metastasis and 41 primary breast cancers relapsed at other anatomical sites. Based on the univariate analysis in an independent cohort of 192 clinically annotated breast tumors (EMC-192 sets), the network signature was validated and reduced first to a set of 31, and later a set of 5, genes whose overall expression score was associated with brain relapse ($P<0.05$). A core intervention signaling network for breast cancer brain metastasis was constructed.

Instead of developing new drugs, the FDA-approved drug sunitinib identified via the known targets FLK1 (vascular endothelial growth factor receptors, VEGF-R) and RET (proto-oncogene tyrosine-protein kinase receptor ret) was positioned in the network signature, with the ability of penetrating BBB as well, on preclinical mouse models to test the efficacy of sunitinib on prohibiting the metastatic colonization of brain by a brain-seeking derivative of the MDA-MB-231 human breast carcinoma cell line (i.e., 231-BR cells).

The role of VEGF in breast cancer brain metastases has been reported that raised VEGF expression contributes to the ability of breast cancer cells to form brain metastasis. Targeting endothelial cells with a VEGF receptor specific tyrosine kinase inhibitor reduced angiogenesis and restricted the growth of the brain metastases. Sunitinib has been approved for the treatment of patients with advanced or metastatic renal cell carcinoma (RCC) and/or metastatic malignant gastrointestinal stromal tumors after disease progression or intolerance to imatinib mesylate. Just recently, it has been reported that the efficacy result of sunitinib on RCC brain metastasis was encouraging in the expanded-access trial of sunitinib for 4564 patients with metastatic RCC and bad-performance status or poor prognosis clinical status, the objective response rate for the brain metastases subgroup was 12%. Sunitinib inhibits cellular signaling by targeting multiple RTKs, includes all platelet-derived growth factor receptors (PDGF-R), VEGF-R, KIT (CD117, stem cell factor receptor), RET, CSF-1R (colony stimulating factor receptor Type 1), and flt3 (Fms-like tyrosine kinase-3). However, sunitinib has not yet demonstrated clinical efficacy against breast tumors with brain metastasis.

The blood brain barrier (BBB) may be more leaky and permeable than previously thought in patients with brain metastasis such that these agents may cross the BBB but not achieve therapeutic concentrations in the brain. Patients without prior exposure to agents, such as cyclophosphamide, methotrexate, 5-fluorouracil, vincristine and doxorubicin, can have significant objective responses in the brain metastases. Today, most patients, however, would likely have received such agents in the adjuvant setting, thus emphasizing the importance of both chemo-sensitivity and CNS penetration for the effective treatment of brain metastasis.

Numerous retrospective studies of breast cancer patients with brain metastases found that over-expression of HER2 was associated with the development of brain metastatic disease. In addition, Palmieri et al. previously reported that among resected brain metastases from 123 breast cancer patients, 36% over-express HER2, indicating an enrichment of HER2 over-expression in breast cancer cells in the brain compared with those in primary tumors (Tham et al., 2006). For the present brain metastasis network signature (BrMNS), the association of BrMNS status with brain relapse remained significant within both the Her2+ and Her2− tumors in our 52 sets and the EMC-192 sets. Thus, two mouse xenograft models of brain metastasis (generated by transfecting HER2-overexpressing MDA-MB-231-BR (231-BR) brain-seeking breast cancer cells with an expression vector that contained or lacked the HER2 cDNA) were used to examine the in vitro and in vivo effects of sunitinib. In vitro, sunitinib inhibited the cell proliferation, migration, invasion and mammosphere form efficiency in 231-BR cells (both with and without HER2). Among mice injected with 231-BR-vector or 231-BR-HER2 cells, those treated with 40 or 80 mg sunitinib/kg body weight had significant fewer macro and micro metastases 32 days after starting treatment than those treated with the vehicle ($p<0.05$). The present study revealed two significant findings: first, the new systems biology modeling presented herein has discovered the breast cancer brain metastasis network signature; and second, based on the repositioning strategy employed by the present inventors, sunitinib has first been validated for use in preclinical models for activity against brain metastases of breast cancer.

Materials and Experimental Methods

Drugs and Cell Lines.

Sunitinib malate was purchased from LC Laboratory (Woburn, Mass., USA) and dissolved in 0.1 M citrate buffer (pH 4.7) at a stock concentration of 3 mg/mL. The human MDA-MB-231-BR "brain-seeking" breast cancer cell line (hereafter referred to as 231-BR cells) was previously described (Han et al., 2004). The 231-BR cells were transduced to express enhanced green fluorescent protein (EGFP) and transfected to overexpress HER2 as described in Palmieri et al. (21). Briefly, the retroviral vector pLEGFP-C1 (BD Biosciences, San Jose, Calif., USA) was transfected into the murine fibroblast PT67 packaging cell line. After 24 hours, EGFP-expressing cells were selected in the presence of 1 mg/mL G418 (Invitrogen, Carlsbad, Calif., USA) and colonies were expanded. EGFP virus was harvested from the PT67 cells and used to infect 231-BR cells. The following day, 231-BR cells were selected in the presence of 0.8 mg/mL G418. EGFP expressing cells were then co-transfected with pCMV4.HER2 full length human cDNA and pSVzeo to confer antibiotic resistance. The sequence of the HER2 insert in pCMV4. HER2 was confirmed by sequencing. Stable colonies were selected in the presence of 0.750 mg/mL zeocin. A vector control cell line was simultaneously established by transfecting both pCMV4 that lacked inserted cDNA and pSVzeo into the 231-BR-EGFP cells and selecting stable colonies in the presence of 0.750 mg/mL zeocin. The 231-BR cells that were transfected with vectors that contained or lacked the HER2 cDNA were maintained in Dulbecco's modified Eagle Medium (DMEM, Invitrogen) supplemented with 10% fetal bovine serum (FBS, Invitrogen) and 1% penicillin—streptomycin solution (Invitrogen). The human breast cancer SKBr3 cell line was purchased from the American Type Culture Collection (Manassas, Va., USA) and maintained in DMEM with 10% FBS.

Cell Proliferation Assay.

231-BR-vector and 231-BR-HER2 cells were plated at a density of $5 \times 10^3$ cells per well in 96-well plates in DMEM plus 10% FBS and incubated overnight to allow cells to adhere to the substratum. The cells were treated with various concentrations (0.1-0 µM) of sunitinib or with DMSO (i.e., the diluent for sunitinib) as a control. The number of viable cells was determined every 24 hours till 120 hours after sunitinib addition by adding 3-(4,5-dimethyl-2-thiazolyl)-2,5-diphenyl-2H-tetrazolium bromide (MTT; Sigma Chemical Co., St. Louis, Mo., USA) at a final concentration of 0.5 mg/mL to each well. After a 2-hour incubation at 37° C., DMSO was added to the wells to dissolve the cells and solubilize the MTT, and absorbance was measured at 570 nm. Data were presented as a percentage of the vehicle-treated control cells at each time point tested. Three separate experiments were performed, with six replicate wells for each data point.

Time-Lapse Living Cell Tracking.

231-BR-vector and 231-BR-HER2 cells were plated in 24-well plates (25,000 cells per well), which was coated with a thin layer of Matrigel. After serum starvation overnight, the cells were exposed to sunitinib or DMSO for 24 hours. Then, cells were replaced with normal medium after washing by warm PBS. Time-lapse cellular images were acquired using an Olympus Live Cell Imaging system every 15 minutes for 24 hours, giving a total of 96 images for each position. The motility ability of individual cells was characterized by using an automated cell tracking algorithm proposed by our group (50). In summary, the cell tracking method consists of three steps: first, a bank of Laplacian-of-Gaussian (LOG) filters were applied to the cellular image to yield a feature image, in which the high intensity pixels indicate the positions of cell centers; second, the mean shift algorithm was used to track the cells in the feature image; and finally, the cell disappearing, appearing, splitting, and merging were handled.

Cell Invasion Assay.

Cell invasion was examined with the use of 48-well Boyden insert chambers. Briefly, the top and bottom compartments of the chambers were separated by polycarbonate (polyvinylpyrrolidone-free) nucleopore filters (8-µm pore size, Neuro Probe, Gaithersburg, Md., USA) coated with Matrigel (BD Biosciences). FBS (1%) in DMEM was used as the chemoattractant in the bottom chamber. 231-BR-vector and 231-BR-HER2 cells were pretreated for 24 hours with Sunitinib (0.1 or 10 µM) or diluent (DMSO). The pretreated cells ($3 \times 10^5$ cells/mL) were added to the top chamber in DMEM supplemented with sunitinib or diluent (DMSO). The chambers were incubated for 4 hours in a 37° C. incubator with 5% $CO_2$. The chambers were disassembled and the filters were fixed and stained with the use of a Diff-Quik kit (Fischer Scientific, Pittsburgh, Pa., USA). Cells that had migrated and invaded to the undersurface of the membrane were counted with the use of a light microscope. Three separate studies were performed with four replicate wells for each data point in study 1 and three replicate wells in each of studies 2 and 3.

Flow Cytometric Analysis for Cell Cycle Distribution.

Cells were serum starved overnight and subsequently treated with sunitinib or DMSO for 24 hrs, then harvested by trypsinization, pelleted by centrifugation, and washed once with cold PBS. While vortexing cells, ice-cold 75% ethanol was added drop wise to resuspend the cells. The cells were fixed in 75% ethanol overnight at −20° C. until staining. Before staining, 1-3 millions of cells were pelleted, washed once with PBS, followed by resuspension in 500 µL PBS containing 50 µg/mL propidium iodide (PI; BD Pharmingen, San Diego, Calif., USA), 20 µg/mL RNAse A (Invitrogen), and 0.03% Triton X-100. Incubation was carried in the dark at 37° C. for 30 min. Cells were counted on a FACSCalibur cell sorter using CellQuest software (Beckton Dickinson, Mountain View, Calif., USA). Cell cycle analysis was performed by a commercial DNA analysis package (Modfit LT 2.0, Verity Software House Inc., Topsham, Me., USA), and the percentages of cells in the G0/G1, S, and G2/M phases of the cell cycle were determined.

Mammosphere-Forming Efficiency (MSFE) Analysis.

Single-cell suspensions of cell lines were plated on non-adherent (polyhema-coated) plastic and counted with a hematocytometer, and 20,000 cells were then seeded into a six-well ultralow attachment plate in Dulbecco's modified Eagle's medium/F-12 containing 5 mg/mL insulin, 0.5 mg/mL hydrocortisone, 2% B27 (Invitrogen Ltd.), and 20 ng/mL epidermal growth factor. Cultures were fed twice weekly and passaged every 2 weeks. Mammospheres were counted by week 2. When passaged, mammospheres were harvested, incubated with trypsin for 3 minutes at 37° C., and dispersed by pipetting with a 23-gauge needle. After checking for single cells, the cells were pelleted and suspended in mammosphere culture medium. MSFE was calculated by dividing the number of mammospheres by the number of seeded cells. In addition, established mammospheres were serially passaged by dissociation, and single cells were replated on fresh nonadherent plastic to form secondary mammospheres, which were counted using an Olympus IX81 microscope with Slidebook software after 2 weeks.

In Vivo Animal Studies.

Animal procedures were conducted in accordance with the guideline of IACUC and institutional regulations. In two studies, a total of 120 female BALB/c nude mice (5-7 weeks old; Charles River Laboratories, Frederick, Md., USA) were anesthetized with isoflurane/$O_2$ and injected in the left cardiac ventricle with 231-BR-vector or 231-BR-HER2 cells ($1.75 \times 10^5$ cells in 0.1 mL serum-free medium; n=30 mice per cell line/study). Sunitinib treatment began 5 days after cell injection. Mice were randomly assigned to receive vehicle (0.5% hydroxypropylmethylcellulose with 0.1% Tween 80 in water) or sunitinib (40 or 80 mg/kg body weight) once daily by oral gavage for 24 days (n=14-18 mice per treatment group). Mice were euthanized by $CO_2$ asphyxiation at the end of treatment or when they showed signs of neurological impairment. The whole brain was removed from the skull and subjected to fluorescence imaging to detect the presence of the injected 231-BR cells. EGFP fluorescence was detected in whole brains and 4 quarters of 2 mm-thick brain slices with the use of a Maestro 420 In Vivo Spectral Imaging System (Cambridge Research and Instrumentation, Woburn, Mass., USA) and data acquisition and processing software that could distinguish or unmix images of fluorescence from multiple sources (Nuance Technology, Burlington, Mass., USA). Paraffin-embedded brain sections (10 μm thick) were serially cut and 5 H & E-stained serial sections and 5 CD34-stained sections every 200 μm of the brain were analyzed for the presence of metastatic lesions with the use of an Olympus Nanozoomer microscope scanner (Olympus). Micrometastases (i.e., those ≤50 $\mu m^2$) per section were counted as were every large metastasis (i.e., those >50 $\mu m^2$) in each section, and the intensity of CD34-positive signals in the sections were quantified by Slidebook software (Olympus). The >50 $\mu m^2$ metric for large metastases represents the mouse equivalent of the proportion of a magnetic resonance imaging—detectable brain metastasis (5 mm) to the length of a human brain. All analyses were carried out by two investigators who were blinded to experimental group assignment. Two separate studies were performed, and the data were pooled for statistical analysis.

Example 2

A Systems Biology Strategy of Drug Repositioning in Cancer and its Application for Breast Cancer Brain Metastasis Drug repositioning is the application of known drugs and compounds to new indications (Ashburn and Thor, 2004). A significant advantage of drug repositioning is that the repurposed drugs can bypass much of the early cost and time over the de novo drug development. The study of drug repositioning has so far been focused on two strategies, one is "on-target repositioning," which applies a drug's known pharmacological mechanism to a different therapeutic indication; for example, comparing the structural similarities of small molecules (Keiser et al., 2009; Miller, 2002) or known side effects (Campillos et al., 2008). In contrast, "off-target repositioning" attempts to describe the pharmacological mechanisms still unclear for known molecules. A number of approaches have recently been developed for "off-target repositioning" by using gene signatures for drug treatment (Lamb et al., 2006; Shats et al., 2010) i.e., subsets of genes or drug-similarity gene network (Minn et al., 2005). With regard to repositioning drugs for targeting brain metastasis, as there is no approved or widely accepted drugs to facilitate "off-target repositioning" approach, the present invention defines a breast cancer brain metastasis-gene network signature (BCBM-GNS) for repositioning known drugs that inhibit the targets in the network signature.

Drug repositioning is growing in popularity. Nevertheless, most successful crossovers are by serendipity. The present invention provides a new systems biology strategy that combines "dry lab" bioinformatics analysis with "wet lab" pre-clinical validation to reposition known drugs for cancer treatment. The utility of the strategy is illustrated by identifying a signal network signature to enable repositioned drugs targeting breast cancer brain metastasis, which still has no cure. A 31-gene signal network signature was derived by network biology-based analysis on gene expression profiles of primary breast tumors, leveraging the similarity characteristics of the metastatic breast cancer in the brain with originating tumors at the primary sites. Instead, to develop de novo inhibitors and/or modulators, these genes were mapped to a centralized known drug database, and ten candidate drugs were obtained that possessed central nervous system permeability, and could antagonize the targets of the 31-identified signature proteins (Table 3). Among the ten drugs, sunitinib and dasatinib were validated in triple negative and Her2-overexpressing xenografts as inhibitors of the metastatic colonization in brain through inhibition of perivascular invasion, proliferation of tumor cells, and angiogenesis. These two drugs were also capable of inhibiting the mammo-neurosphere-initiating cells that reside in brain metastatic lesions. The animals that were injected with drug-treated sphere-dissociated cells showed a significant delay in brain metastasis occurrence. This strategy permits identification of a signaling network signature and enables drug repositioning in breast and other cancer types.

Recent findings based on expression profiling of primary breast tumors and their matched metastases, as well as clinical validation studies by Minn and colleagues are supporting the idea, that poor prognosis—as well as organ-specific metastasis genes can be detected already in the primary tumors (Minn et al., 2005; Ramaswamy et al., 2003; Weigelt et al., 2003). In this study, 31-node BCBM-GNS has been identified, which was derived directly from patient primary tissue instead of CNS-homing cells.

In addition, from a systems biology perspective, it is becoming increasingly clear that the identification of protein-protein interaction networks may better gauge the level of perturbation of a biological system as a whole (Barabasi and Oltvai, 2004; Hartwell et al, 1999), compared with single genes. Thus, a network biology approach was used to define the network signature, in which the 31 proteins have certain patterns of protein-protein interaction (PPI), and the PPI based sub-networks are highly correlated with the clinical brain metastasis status. With the identified signature genes, instead of developing inhibitors and/or modulators de novo, these genes were mapped to a database of nearly 6,000 known drugs with their known targets and pharmacology information. A repositioning drug candidate was selected if it meets two criteria: first, the drug antagonizes the target among of the 31-gene encoded proteins, and second, the structure of the drug, or existing experimental evidence has demonstrated the drug has CNS permeability (Pajouhesh and Lenz, 2005). Three out of 10 repositioned drug candidates in the present example have shown efficacy on targeting brain metastasis. These include vorinostat (Palmieri et al., 2009), pazopanib (Gril et al., 2011), and XL-184 (Gordon, et al., 2011).

In a preclinical validation study, two drugs, sunitinib and dasatinib, both reduced the brain metastatic colonization in triple-negative and Her2-overexpressing xenografts by inhibiting the perivascular invasion and proliferation of tumor cells. Sunitinib also showed effects on reducing the enlarged and tortuous blood vessels in the metastatic loci and the surrounding edema. Furthermore, an initial study has shown that these two drugs were capable of inhibit tumor-initiating cells residing in the brain metastatic lesions, as measured by the mammo-neurosphere formation assay. Animals that received drug-pre-treated tumor cell injection also showed significant delay in brain metastasis occurrence.

Materials and Methods

Drugs and Cell Lines.

Sunitinib malate and dasatinib were purchased from LC Laboratory (Woburn, Mass., USA). Sunitinib was dissolved in 0.1 M citrate buffer (pH 4.7) at a stock concentration of 3 mg/mL. Dasatinib was dissolved at 10 mM in 100% dimethyl sulfoxide (DMSO). The human MDA-MB-231-BR "brain-seeking" breast cancer cell line (231-BR cells) (Bos et al., 2009) was transfected with GFP (National Cancer Institute, Bethesda, Md., USA) (Yoneda et al., 2001). MDA-MB-231 parental cell lines and derivatives were cultured in DMEM supplemented with 10% FBS, 1 mg/mL fungizone, and 100 U/mL penicillin/streptomycin. Primary human endothelial cells (HUVEC, ScienCell) and astrocytes (ScienCell) were cultured in M199 medium supplemented with 2.5% fetal bovine serum (FBS), 10 mg/mL insulin, 0.5 mg/mL hydrocortisone, 20 ng/mL EGF, 100 ng/mL cholera toxin, 1 mg/mL fungizone, and 100 U/mL penicillin/streptomycin.

Knockdown Cell Lines.

Knockdown of RET, KDR and FYN was achieved by shRNA lentiviral particles from Santa Cruz biotechnology (Santa Cruz, Calif., USA). The efficiency of the knockdown was confirmed by quantitative PCR with reverse transcription (qRT-PCR) TaqMan gene expression assays (Applied Biosystems), or western immunoblotting analysis (anti-pRET, anti-pFYN and anti-pKDR antibodies were purchased from Santa Cruz, Calif., USA). β-actin was used as endogenous controls for both qRT-PCR and western hybridization analyses. Only cell lines with a transduction rate over 80% were used in further studies.

Cell Invasion Assay.

Cell invasion was examined with the use of 48-well BD Biocoat Matrigel Cell Invasion Chamber (Becton Dickinson, Bedford, Mass., USA). 231-BR-vector and 231-BR-HER2 cells were pretreated for 4 hours with sunitinib or dasatinib. The pretreated cells ($3\times10^5$ cells/mL) were added to the top chamber in DMEM supplemented with sunitinib or dasatinib. The chambers were incubated for 24 hours in a 37° C. incubator with 5% $CO_2$. Instead of counting the invaded cell from random selected fields of the membrane, whole membrane montage images were taken and the total number of cells on the underside of the membrane was determined to calculate the "Invasion Index."

In Vitro Blood-Brain Barrier Assay.

The analysis on cancer cell lines penetrating in vitro BBB was performed as described (Bos et al., 2009). $10^5$ human primary brain microvascular endothelial cells (HBMECs, ACBRI379 from Cell Systems Corporation) were placed on the upper chamber of the inserts, and human primary astrocytes (ACBRI371 from Cell Systems Corporation) were placed on the counter side of the insert membrane. In this study, Evans blue-conjugated albumin (0.45% in phenol red-free medium) was used to examine the permeability. Controls included astrocyte alone, HBMECs alone, HBMECs on both sides of the insert membrane and insert alone.

In Vivo Animal Studies.

Animal procedures were conducted in accordance with the guidelines of IACUC and institutional regulations. Female BALB/c nude mice (7 weeks old; Charles River Laboratories, Frederick, Md., USA) were anesthetized with isoflurane/$O_2$ and injected in the left cardiac ventricle with cell lines (231-BR-HER2 or 231-BR-vector cells) or mammo-neurosphere-derived single cells ($1.75\times10^5$ cells in 0.1 mL serum-free medium). The animals injected with the cell lines were randomly divided into 5 treatment groups: vehicle, low dose sunitinib (40 mg/kg), high dose sunitinib (80 mg/kg), low dose dasatinib (25 mg/kg), high dose dasatinib (50 mg/kg). Treatment started 3 days after cell injection. Both sunitinib and dasatinib were administered orally once daily for 28 days. The remaining mice were injected with single cells dissociated from the mammo-neurospheres, which had been pre-treated with sunitinib (1 μM or 5 μM), dasatinib (100 nM or 1000 nM) or vehicle control, for 48 hours. Appearance of brain metastasis of the mice was monitored every week by IVIS200 bioluminescent imaging. The body condition was monitored once every day, and the mice were euthanized by $CO_2$ asphyxiation if there were signs of neurological impairment or if the body condition score was ≤2.

The animals were euthanized at 6 hrs after last treatment. Whole brain was immediately harvested and rinsed with ice-cold saline to remove extraneous blood. The whole brain was subjected to fluorescence imaging to detect the presence of the injected cells. GFP fluorescence was detected in whole brain using a Maestro 420 In Vivo Spectral Imaging System (Cambridge Research and Instrumentation, Woburn, Mass. USA), and data acquisition and processing software that could unmix images of fluorescence from multiple sources (Nuance Technology, Burlington, Mass., USA). After fluorescence imaging, some of the mouse brains were carried for histological study, and others were used for examining the GFP expression in brain lysates.

Histological Analysis and Microscopy.

Brain sections (10 μm thick) were serially sectioned. One section from every 300 μm was stained with H&E and immunohistochemistry for p-RET, p-FYN, Ki67 and CD31. Briefly, the immunohistochemistry was performed on formalin-fixed, paraffin-embedded brain sections. The antibodies were incubated after heat-induced epitope retrieval (HIER) with citrate buffer (pH 6.0) and steam pretreatment for 30 min. Biotinylated secondary antibodies were used, and the detection was performed with DAB Peroxidase Substrate Kit (SK-4100; Vector Laboratories). Slides were counterstained with hematoxylin (Fisher Scientific) and mounted in Permount (Fisher Scientific). The whole section montage images were acquired by Olympus BX61 microscope, and a software algorithm was developed for the segmentation and quantification analysis. An image analysis algorithm was also developed to automatically quantify the number and area of the large lesions in the montage H&E gray-scale images, as described previously (Zhao et al., 2011).

Determination of Drug Concentrations in Mouse Plasma and Brain Using HPLC-MS/MS.

Brain metastatic xenograft mice were orally fed with sunitinib and dasatinib once daily for 14 days starting from 2 weeks after tumor cell injection. Blood and whole brain of the mice were harvested 6 hours after the last treatment. Plasma was isolated from blood by centrifugation at 3000 rpm for 10 min at 4° C. Half of each brain was flash frozen using liquid nitrogen. All plasma and brain samples were stored at −80° C. until analysis by HPLC-MS/MS. Linear ion trap quadrupole LC/MS/MS 3200Q trap mass spectrometer (Applied Biosystem/MDS SCIEX, Foster City, Calif., USA) equipped with HPLC system was used to determine sunitinib and dasatinib in aqueous and biological matrices using testosterone as an internal standard (IS). The positive ion mode for MS/MS analyses was selected, and the quantification was performed using MRM method with the transitions of m/z 400→m/z 284 for sunitinib, m/z 488→m/z 401 for dasatinib and m/z 289→m/z 109 for testosterone (1S).

The separation was performed by injecting 10 μL of the sample on Acquity HPLC BEH C18 column (50×2.1 mm I.D., 1.7 μm, Waters, Milford, Mass., USA). Gradient elution (with a mobile phase consisting of 0.1% formic acid [A] and 100% acetonitrile [B]) was adapted in the following sequence 0-5% B at 0-0.5 min, 5-90% B at 0.5-2.4 min, 90-5% B at 2.4-3.1 min to separate sunitinib, dasatinib and testosterone (IS) from the matrices. The flow rate was 0.45 mL/min using a column temperature of 45° C. The retention time of sunitinib, dasatinib and IS were 1.62, 1.58 and 1.85 min, respectively. A good linear relationship with coefficients of determination≥0.99 was achieved over the sunitinib concentration ranges of 119-13300 ng/mL for plasma and 89-9961 ng/g for the brain tumor, and concentration ranges of 35-45000 ng/mL for plasma and 18-21940 ng/g for the brain tumor for dasatinib.

Isolation of Brain Metastatic Cells and Mammo-Neurosphere Culture.

A cell suspension containing $1.75 \times 10^5$ 231-BR cells in 0.1 mL serum-free medium was injected in the left cardiac ventricle of anesthetized 6-7-week-old BALB/c nude mice. Tumor development was monitored by weekly bioluminescence imaging using the IVIS-200 imaging system from Xenogen as previously described (Zhao et al., 2011). Brain metastatic lesions were confirmed by MRI and histological analysis after necropsy. Brain lesions were localized by ex vivo bioluminescence imaging, and resected under sterile conditions. The brain tissue was minced and placed in culture medium containing a 1:1 mixture of DMEM/Ham's F12 supplemented with 0.125% collagenase III and 0.1% hyaluronidase. Samples were incubated at room temperature for 4-5 hr, with gentle rocking. After collagenase treatment, cells were briefly centrifuged, resuspended in 0.25% trypsin, and incubated for a further 15 min in a 37° C. water bath. Single-cell suspensions were suspended at a density of 40,000 cells/mL in mammosphere medium, and seeded into low-adherent six-well plates (2.5 mL per plate) (Corning Life Sciences). Mammosphere medium contains mammary epithelial growth medium (MEGM, Lonza, Walkersville, Md., USA) supplemented with B27 and bFGF, and EGF at final concentrations of 20 ng/mL each). Cultures were fed weekly and passaged every 2 weeks. When passaged, spheres were collected, dissociated with trypsin (0.05%) for 5 min at 37° C., filtered through a 40-micron filter, counted, and replated at 20,000 cells/mL in MEGM plus supplements.

Differentiation of Mammo-Neurosphere Cells and Immunofluorescent Staining.

Disaggregated mammo-neurospheres were seeded on glass coverslips in mammosphere medium supplemented with 5% fetal bovine serum (FBS). Cells were allowed to adhere and differentiate for 7 days before fixing and staining. Differentiated mammo-neurosphere-derived cells grown on glass coverslips or mammo-neurospheres in suspension were fixed in 4% paraformaldehyde for 10 minutes, washed in PBS, and then permeabilised in 0.1% Triton X-100 for 5 min. After further washing in PBS, cells were incubated for 1 hour at room temperature with neat primary antibody nestin (1:200, Millipore), cytokeratin 5 (CK5) (1:200, Santa Cruz Biotechnology), CK18 (1:200, Santa Cruz Biotechnology), CK19 (1:100, Labvision), FITC-CD44 (BD Pharmingen), PE-CD24 (BD Pharmingen) and PE-CD133 (eBioscience). Following a wash in PBS, the cells were incubated for 1 hour at room temperature in secondary antibody Alexa 488-conjugated rabbit anti-mouse (Molecular Probes/Invitrogen Corporation, Carlsbad, Calif., USA) diluted 1:500 in PBS. Cells were washed with PBS before coverslips were air-died and mammospheres stained in suspension were spun-down with all supernatant removed. Coverslips and spheres were then stained and mounted with 10 mg/mL DAPI (4,6-diamidino-2-phenylindole dihydrochloride) (Sigma-Aldrich, Poole, UK) in aqueous mountant (Dako 2972; DakoCytomation, Glostrup, Denmark) and viewed under a Olympus FV1000 confocal microscope (Olympus).

Mammo-Neurosphere Formation Efficiency after Drug Treatment In Vivo.

Using cells derived from the other half of the brain tissue shared with the brain drug concentration study, the inventors tested whether sunitinib and dasatinib targeted mammo-neurosphere-initiating cells during the course of treatment. For each mouse and treatment, individual tumors were dissociated to single cells by collagenase digestion. Dissociated tumor cells were filtered through a 40-micron filter, and plated 20,000 cells/mL of mammosphere medium in low-adherent 24-well plates (Corning Life Sciences). For the secondary mammosphere formation efficiency (MSFE) assay, spheres were collected, dissociated with trypsin (0.05%) for 5 minutes at 37° C., filtered through a 40-micron filter, counted, and replated at 20,000 cells/mL MEGM plus supplements. Spheres (>50 micron) were imaged and counted using Olympus BX81 microscope under the automatic montage function.

RNA Isolation and Gene-Expression Profiling.

Core biopsies from primary tumors of 52 breast cancer patients were obtained using an MC1410 MaxCore biopsy instrument. Two to three core biopsy specimens were immediately transferred for snap freezing at −80° C. for cDNA array analysis. RNA was isolated (RNeasy kit, QIAGEN) and reverse transcription performed in accordance with protocols recommended by the manufacturer (Affymetrix) using commercially-available buffers and proteins. From each biopsy specimen, 15 μg of labeled cRNA was hybridized onto the Human Genome U133 GeneChip using recommended procedures for pre-hybridization, hybridization, washing, and staining with streptavidin-phycoerythrin (SA-PE). The analytical approach to the data analysis is as described previously (Chang et al., 2003).

$RT^2$-PCR Array.

A customized $RT^2$-PCR array was developed to examine the expression of 31 genes in the network-based signature and $RT^2$ Real-Timer SyBR Green/ROX PCR Mix were purchased from SuperArray Bioscience Corporation (Frederick, Md., USA). PCR was performed on ABI Prism 7700 Sequence Detector (Applied Biosystems). Relative changes in gene expression were calculated using the $\Delta Ct$ (threshold cycle) method. Five housekeeping genes were included on the array (GUSB, TRFC, RPLP, GAPDH, and ACTB) to normalize the RNA amounts.

Human Breast Tumor Microarray Data Sets.

Four cohorts of breast tumors that include patients with brain metastasis were used for analysis. The BCM-52 cohort includes 11 patients that were examined with both primary tumor and brain metastasis when performed the biopsy. Other 41 patients were examined with both primary tumor and other organ metastasis when performed the biopsy. EMC-192 (Bos et al., 2009) cohort includes 16 samples that the patients had brain relapse, and 75% is from patients that relapsed to different organs and received first-line chemotherapeutics. EMC-286 (Wang et al., 2005) cohort includes 10 samples that the patients had brain relapse, and 97% is T1-T2. The MSK-82 (Minn et al., 2005) cohort included 5 samples that the patients had brain relapse, and 91% is T2-T4.

Network-Based Signature Analysis.

The inventors developed a new network-biology based approach to reposition drugs for brain metastasis of breast cancer (BCBM) patients. A new concept called Cancer-Signaling Bridge (CSB), permitted the identification of key signaling network or network-based signatures for BMBC. CSBs are helpful to expand the cancer drug-targets of singling pathways to individual cancer related genes or proteins. The network-based signature was obtained by the following steps:

(i) identify enriched signaling pathways for BCBM derived from gene expression signature: Pathway enrichment analysis was implemented on the merged 420 microarray data of three cohorts, i.e. BCM-52, EMC-286 and EMC-82, to find the enriched signaling pathways for BCBM. First, the gene signature for BCBM was addressed. Every gene in the signature shows significantly differential expressions between brain metastasis and control group (P<0.01, student t test). Then, the significances or P-values of enrichments of signaling pathways are calculated by right-tailed Fisher's Exact Test, only over-represented pathways that have more genes in the gene signature than expected by chance, are significant. Core analysis of IPA (Ingenuity Pathway Analysis) was employed to address the enriched signaling pathways.

(ii) identify CSBs connected with the enriched signaling pathways: The enriched signaling pathways was denoted as $S=\{S_i\}$ and the connected CSBs as $\pi^s=\{\pi_j^s\}$. Each CSB comprises a set of proteins and a set of interactions among the proteins. Here, $\pi^s$ only presents the sets of proteins in the CSBs and each CSB represents a protein set $\pi_j^s=\{p_1, p_2, \ldots, p_n\}$, where n is the number of elements in the protein set. For each CSB $\pi_j^s$, there exists at least one signaling pathway $S_i$ that contains at least one protein in $\pi_j^s$, such that $|\pi_j^s \cup S_i|>0$.

(iii) Two scores to evaluate the association between network and BMBC: For a simulated signaling network $N_k$, two types of scores, differential expression score (DES) and signaling pathway score (SPS), are proposed to evaluate its association with BCBM. DES and SPS are defined as followings respectively, $$DES_k = \frac{1}{|N_k|} \sum_{i=1}^{|N_k|} -\log_{10}(P-value_i) \quad (1)$$

$$SPS_k = \frac{1}{|N_k|} \left| \bigcup_{l=1}^{|N_k|} \zeta_l \right| \quad (2)$$

where P-value$_l$ is the statistical P value of protein $P_l$ in the network, and $\zeta_l$ is the subset of enriched signaling pathways S in which each signaling pathway includes protein $P_l$. DES in Eq. (1) aims to assess the statistics of differential expression of $N_k$ between BCBM and control patient groups, and SPS in Eq. (2) is able to evaluate to what degree the simulated network is associated with the key enriched signaling pathways for BCBM.

(iv) Multiple Objective programming to find network-based signature: To maximize the two types of scores in Eq. (1) and Eq. (2), Multiple Objective programming was employed to find the network-based signature for BCBM.

$$\text{Max}_x \ goal_1 = \frac{1}{N} \left| \bigcup_{i=1}^{N} (S_i \cap I(x_i)) \right| \left( goal_1 \geq a \sum_{i=1}^{N} x_i \right) \quad (3)$$

$$\text{Max}_x \ goal_2 = \sum_{i=1}^{N} P-value_i \cdot x_i \left( goal_2 \geq b \sum_{i=1}^{N} x_i \right) \quad (4)$$

$$\text{s.t.} \begin{cases} 2 \leq \sum_{i=1}^{N} x_i \leq N & (5) \\ \sum_{i=1}^{N} \sum_{j=1}^{N} A_{ij} x_i x_j \geq \sum_{i=1}^{N} x_i - 1 & (6) \\ x_i = 0, 1 & (7) \\ i = 1, 2, \ldots, N \end{cases}$$

where Eq. (3) and Eq. (4) are to maximize the scores, SPS and DES, respectively, $A_{ij}$ in Eq. (6) is the connectivity matrix for the protein-protein interactions derived from the CSBs $\pi^s$ connected with enriched signaling pathways S, N in Eq. (5) determines the scale of the output network, $x_i$ in Eq. (7) is a variable indicating whether the protein $P_i$ is in the output network.

Hierarchical Clustering. Hierarchical clustering is used to group similar objects into "clusters." The pvclust package was used in R to do the hierarchical clustering on the cohorts, EMC-192, EMC-286 and EMC-82. To investigate the roles of proposed network-based signature in different cohorts, a feature selection based on the hierarchical clustering is performed. Every feature in the hierarchical clustering is not for a single protein but for a subnetwork that comprises 2 to 5 proteins. The gene expression for the feature across samples are defined as:

$$I_{feature} = \frac{1}{\sum_{1}^{N_f} \frac{1}{p_j}} \sum_i \frac{1}{p_i} I_i \quad (8)$$

where $p_i$ is the statistical P-value of protein $P_i$ between BMBC and control groups (student's t-test), $I_i$ is an expression vector that the mean-merged probe expression for coding-gene (or genes) for protein $P_i$, $N_f$ is the number of proteins in the feature f. The feature selection is performed using a greedy algorithm. Briefly, an initial clustering is performed using all features, then the features are sorted by their AU P-values that are calculated via multiscale bootstrap resampling, and eventually determining whether to retain or discard it by a defined clustering performance.

Statistical Methods.

Results were expressed as means±standard deviation (SD) and all statistical tests were two-sided (a P value of <0.05 was considered statistically significant). For the in vivo study results, each group of data were examined the normality with the Jarque-Bera test first, and then Levene's F-test was employed to test multi-group homogeneity of variance (HOV). If the groups enrolled follow the HOV, a t-test was employed for analyzing experimental data. Otherwise, Wilcoxon rank test is executed. For the in vitro study results, analysis of variance (ANOVA) was deployed for the data analysis, with compound doses or different compounds specified as the factor. Survival analysis is implemented by an R package 'Survival'.

Results

Critical Network Biology Approaches Used for Identifying the Network Signature.

Network motif is a sub-graph of proteins that occurs more frequently in the protein-protein interaction (PPI) network than those in random networks and is assumed to be a basic functional unit within a cell (Milo et al., 2002). Network motifs allow the study of not only signaling pathways, but also the communication between different signaling pathways and disease-related genes or proteins. A filtered human protein interactome (FHI) from IntAct, DIP, MIPS, and MINT PPI databases was generated by filtering in the PPIs that were confirmed by at least two independent methods for either 'physical interaction' or 'direct interaction (Han et al., 2004; Batada et al., 2006). This FHI contains 2,887 proteins with 3,681 interactions and then network motifs were detected using mfinder2.1 software. Two types of motifs were identified for our further study-ID: 238, a three-node motif or undirected triangle, and ID: 13260, a four-node motif or undirected square. There are two three-node motifs and several four-node motifs in undirected networks. The triangle, i.e., ID: 238, was chosen because this sub-graph is the only three-node network motif for PPI networks. In other words, the triangle, i.e., ID: 238, occurs more frequently in a real network than random ones (Z-score 25.08, P<0.001), while another one (ID: 78), occurs less frequently in a real network than random ones (Z-score is −25.08, P=1) (Milo et al., 2002). The undirected square (ID: 13260) was chosen since other four-node undirected network motifs can be decomposed into the three-node triangle (ID: 238) and the four-node square (ID: 13260). Therefore, the choice of the two particular motifs represents the most general case for three-node and four-node motifs. Interestingly, we found that the existing drug targets were significantly enriched in motif clusters in the FHI network, which indicates the potential role of network motifs in drug discovery.

The overlap between cancer-related genes and gene-coding proteins was also examined in Online Mendelian Inheritance in Man (OMIM) (Hamosh et al., 2005; Yildirim et al., 2007), and the signaling proteins in Nature Curated pathways (NCI-PID) and BioCarta pathways (Schaefer et al., 2009). A particular network motif, called cancer-signaling bridges (CSBs), was identified which connects a signaling pathway with cancer-related genes or proteins by its component proteins CSBs have been confirmed to be enriched in these connections between oncogenic signaling pathways and cancer-related genes or proteins. CSB mapping allows signaling pathways to connect with significantly more cancer-related genes compared to database mapping ($P<10^{-10}$, Mann-Whitney U test). The CSBs are used to expand the signaling pathways to different types of cancers, and it was found that most CSBs were specifically connected to an individual type of cancer. The drug-target analysis indicated that cancer-related genes/proteins connected within CSBs are much more likely to be targeted by anti-cancer drugs.

Identification of Brain Metastasis-Gene Network Signature (BCBM-GNS).

Using CSBs to expand the existing signaling pathways and, more importantly, the number of cancer drug-targets, the inventors next generated a comprehensive brain metastasis signaling network to facilitate the drug repositioning. The network-based signature is identified by the following steps. The first step enriches signaling pathways identified by brain metastasis-differential expressed genes, Pathway enrichment analysis was implemented on the merged 420 microarray data of three cohorts, i.e., BCM-52, EMC-286 and EMC-82 (all were conducted on Affymetrix HG-133A platform), to find the enriched signaling pathways for breast cancer brain metastasis (BCBM). Differential genes for BCBM were identified. Every gene in the final network signature shows significantly differential expressions between brain metastasis and control group (P<0.01, student t test). Then, the significances or P-values of enrichments of signaling pathways were calculated by right-tailed Fisher's Exact Test, only over-represented pathways that have more differential genes than expected by chance, are selected as significant pathways. The core analysis of IPA (Ingenuity Pathway Analysis) was employed to address the enriched signaling pathways.

In the second step, CSBs were connected with the enriched signaling pathways. The enriched pathways were denoted in the network signature as $S=\{S_i\}$ and the connected CSBs as $\pi^s=\{\pi_j^s\}$ in the signaling network simulation study. Two types of scores, differential expression score (DES) and signaling pathway score (SPS), are proposed to evaluate its association with brain metastasis. DES aims to assess the statistic of differential expression of sub-network, and SPS is able to evaluate to what degree the simulated network is associated with the key enriched signaling pathways. To maximize the two types of scores, a multiple objective programming was applied to find the network-based signature for brain metastasis.

Applying the CSBs-based method to our in-house BCM-52 data, a pre-network-based signature was established with 101 gene nodes and 192 PPI paths associated with brain relapse. To prioritize the sub-networks even further, the inventors screened for those whose DES and SPS scores were associated with brain relapse in other three independent clinically annotated breast tumor cohorts (EMC-192, EMC-286, and MSK-82). Univariate analysis in these tumors showed a 31-gene sub-network was highly correlated (p<0.01) with brain relapse (FIG. 1A, FIG. 1B, FIG. 1C, and FIG. 1D). The association of the 31-gene BCBM-GNS status with brain relapse remained significant within ER+/PR+/HER2+ and ER−/PR−/HER2− early stage tumors; ER−, PR−, HER2− local advanced tumors; and also ER−, PR−, HER2− patients receiving adjuvant therapy (FIG. 6A-1, FIG. 6A-2, FIG. 6A-3, FIG. 6A-4, FIG. 6A-5, FIG. 6A-6, FIG. 6A-7, FIG. 6B-1, FIG. 6B-2, FIG. 6B-3, FIG. 6B-4, and FIG. 6C-1, FIG. 6C-2, FIG. 6C-3, FIG. 6C-4). Eleven out of the 31 genes encoded proteins are the targets of 15 FDA-approved or clinical trial drugs (Table 1).

TABLE 1

Brain metastasis repositioning drug list and their BBB permeability

| Drug target | Drug name | "Rule of Five" for CNS drugs | BBB permeability and anti-brain mets efficacy |
|---|---|---|---|
| HDAC1, HDAC2 | Vorinostat | ✓ | 2009, *Clin Can Res* |
| PHGDH | NADH | | |
| RET | Imatinib | ✓ | |
| KDR | Cabozantinib | ✓ | 2011, *J Clin Oncol* |
| KDR, RET | Sunitinib | ✓ | 2009, *Lancet Oncol* |
| RAF1, KDR | Sorafenib | ✓ | 2010, *Clin Can Res* |
| | Pazopanib | | |
| FYN | Dasatinib | ✓ | 2008, *Blood* |
| NFKB1 | Dexamethasone | ✓ | |
| | Pranlukast | | |
| | Thalidomide | | |
| IKBKB | Auranofin | | |
| | Arsenite | | |
| GRB2 | Pegademase | | |
| VIM | Acetate | | |

A core subset of the BCBM-GNS was identified that contained seven genes, and was the most confident part of the BCBM-GNS to distinguish the patients with BCBM from controls accurately and classify the patients with different metastasis-free survival probabilities exactly in different cohorts (FIG. 1A). Four out of the 7 genes encoded proteins are the targets of 6 FDA-approved or clinical trial drugs, i.e., Pegademase, Imatinib, Sunitinib, Dasatinib, Sorafenib, and Cabozantinib (FIG. 1A).

Figure 2A:
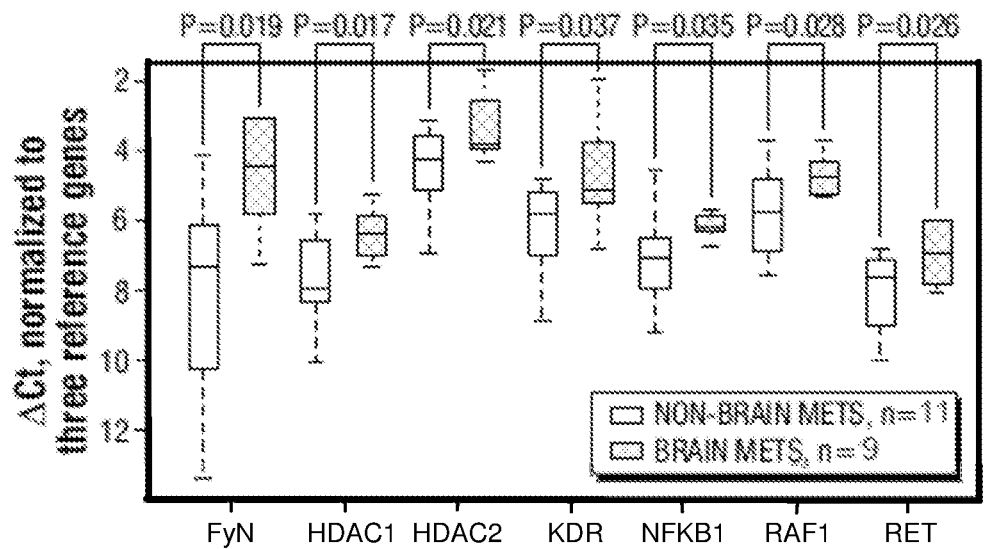
FIG. 2A, FIG. 2B, FIG. 2C, FIG. 2D, FIG. 2E, and FIG. 2F show $RT^2$-PCR array for validating the 31 drug target genes in 20 patients' tissues.

The inventors next confirmed measurements of these microarray RNA levels by the correlation of normalized microarray data versus a 31-gene low density array (LDAs), based on real time quantitative RT-PCR (QRT-PCR) (Rodriguez et al., 2010). Primary breast tumor tissues of twenty breast cancer patients were used for this $RT^2$-PCR array study, in which 9 patients had brain relapse. To compare expression profiles between specimens, normalization based on three reference genes was used. A geometric averaging of three reference genes was used for normalization in a manner previously described (Vandesompele et al., 2002). The average expression of the mean of the three reference genes was $C_T=22.98$. The expression of thirty-one genes normalized to ACTB, GAPDH and RPLP0 at $p<0.05$ was confirmed. The correlation coefficients between the two methods were significantly positive for 24 of 31, (77.42) of the genes ($p<0.05$). In particular, seven drug-target genes (FYN, HDAC1, HDAC2, KDR, NFKB1, RAF1 and RET), were significantly highly expressed in primary tumor of brain relapsed patients (FIG. 2A).

BCBM Repositioning Drug Candidates.

Figure 7B:
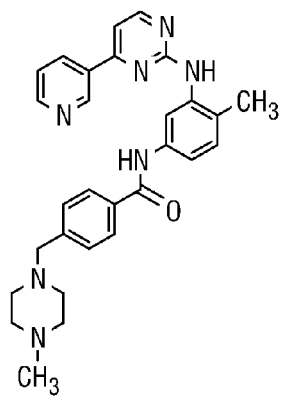
Figure 7B:
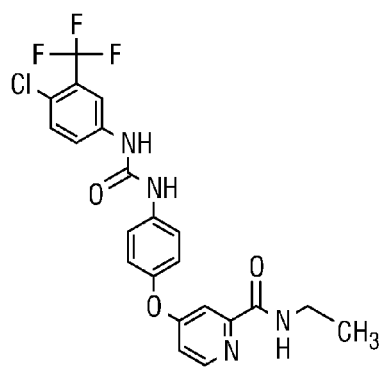
Figure 7B:
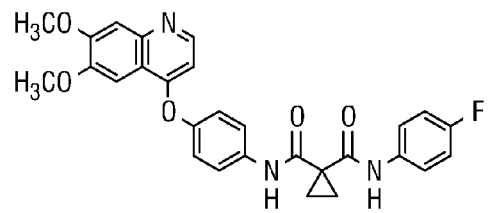
Figure 7C:
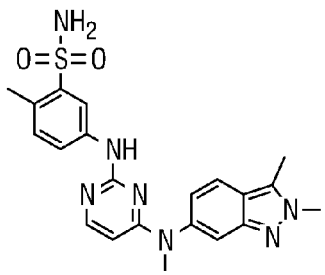
Figure 7C:
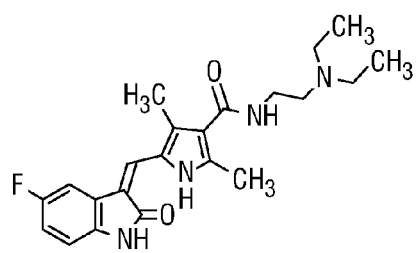
Figure 7C:
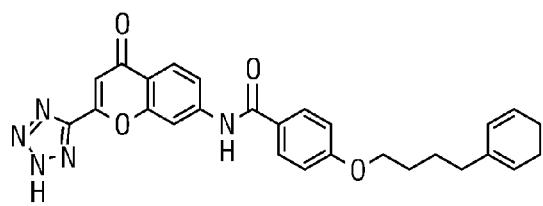
Figures 1, 9A:
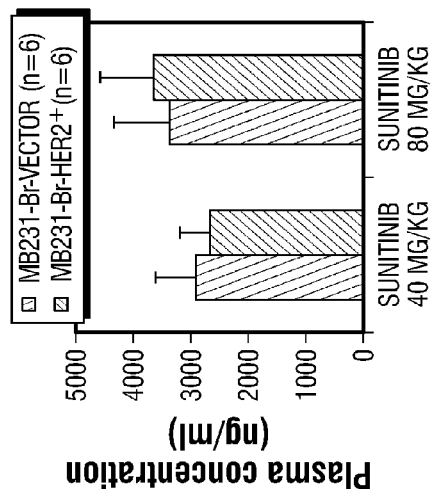
Figures 2, 9A:
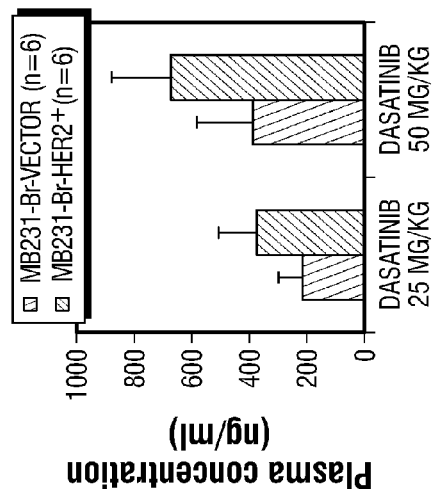

With the BCBM-GNS, all thirty-one genes were mapped into a database of known drugs, giving a total of 15 potential drug candidates. Based on the chemical structures (Pajouhesh and Lenz, 2005) (FIG. 7A, FIG. 7B, and FIG. 7C) and existing evidence for showing the CNS permeability of the drugs, the group was further narrowed to ten drugs that have the potential to benefit BCBM. Three of these 10 drugs have been tested preclinically or clinically to demonstrate efficacy on treating brain metastasis, i.e., Vorinostat, pazopanib, and cabozantinib. In addition, among the ten repositioned drug candidates, dexamethasone is currently often used in clinic as palliation to improve symptoms, and thalidomide has been reported to add advantage as immunomodulatory and anti-angiogenesis in combining with temozolomide or radiation therapy for brain metastasis treatment (Hwu et al., 2005; Hwu et al., 2003).

Sunitinib has been approved for the treatment of patients with advanced or metastatic renal cell carcinoma (RCC) and metastatic malignant gastrointestinal stromal tumors (Motzer et al., 2006; Motzer et al., 2006). It has been reported that the efficacy result of sunitinib on RCC brain metastasis was encouraging in the expanded-access trial of sunitinib for 4,564 patients with metastatic RCC and poor-performance status or poor prognosis clinical status, that the objective response rate for the brain metastases subgroup was 12% (Gore et al., 2009). Dasatinib is an oral dual BCR/ABL and Src-family tyrosine kinase inhibitor approved for use in patients with chronic myelogenous leukemia (CML). It has been reported to be able to cross the BBB, and efficient in managing intracranial leukemic disease (Porkka et al., 2008). In addition, the "rule of five" chemical structure (Pajouhesh and Lenz, 2005) for sunitinib and dasatinib support their penetration ability through BBB.

Figure 2B:
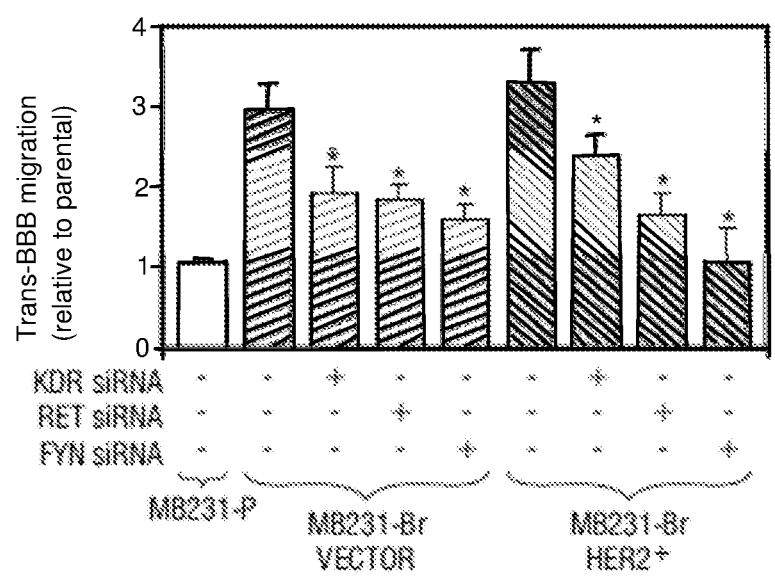
Figure 2C:
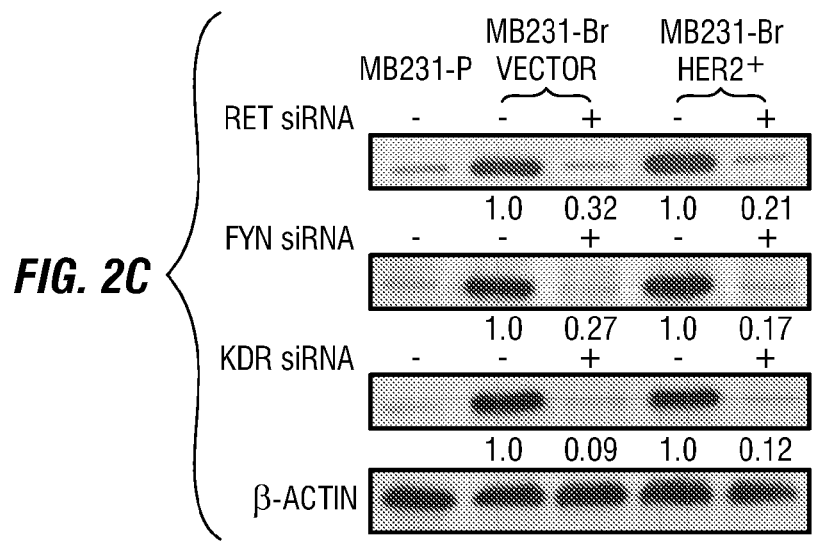
Figure 2D:
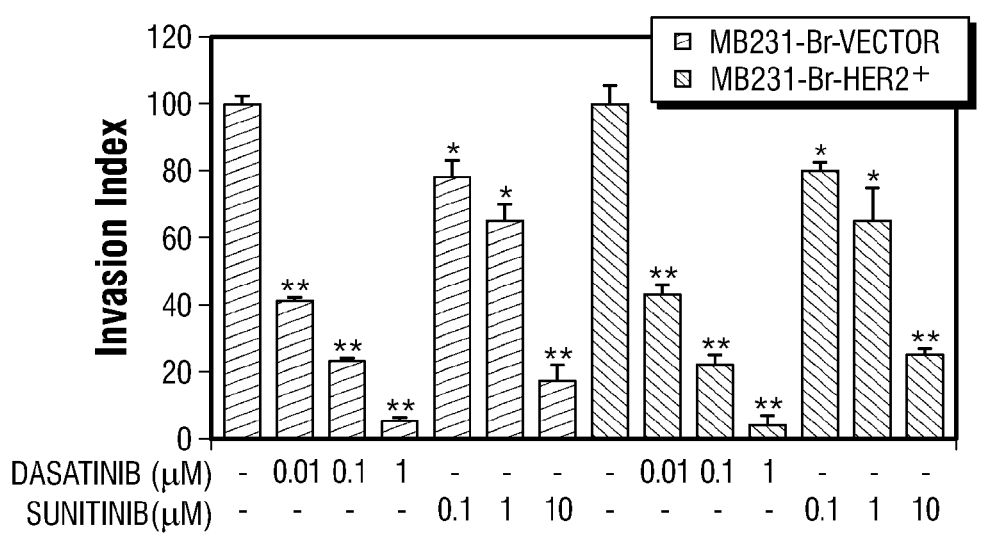
Figure 2E:
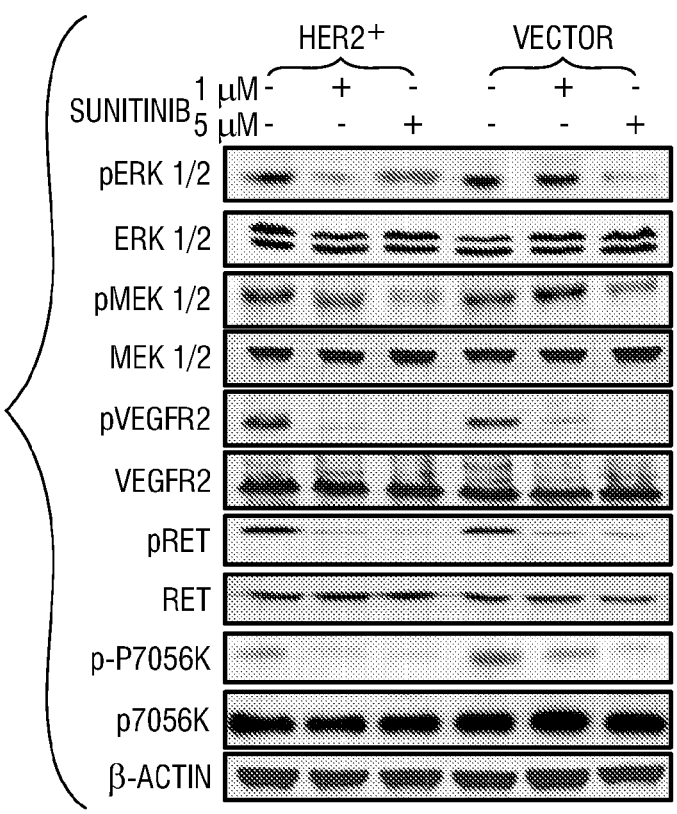
Figure 2F:
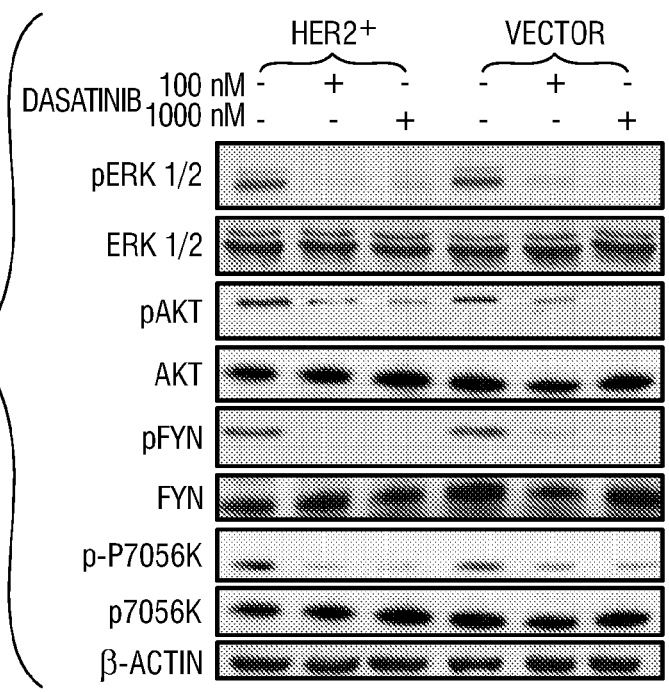
Figure 8:
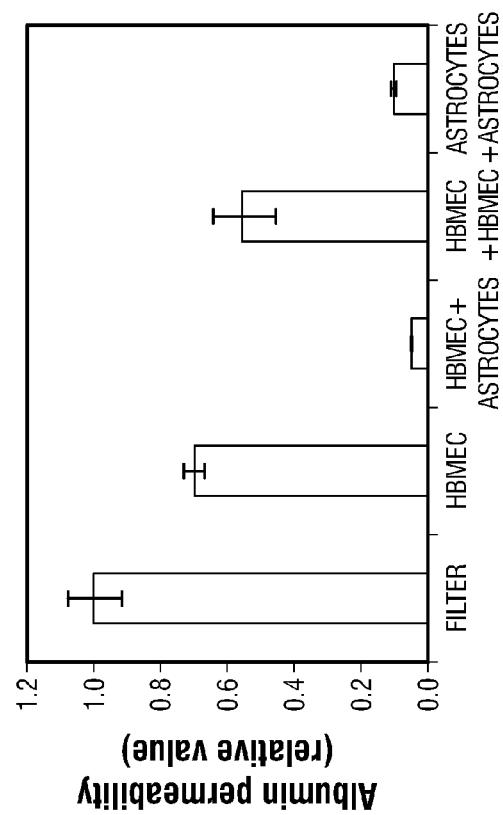
FIG. 8 shows albumin permeability analysis to determine the tightness of the in vitro BBB layer. Absorbance at 620 nm is shown relative to an empty tissue culture insert. Data are the average of triplicate determination s±sd.
Figures 3, 9A:
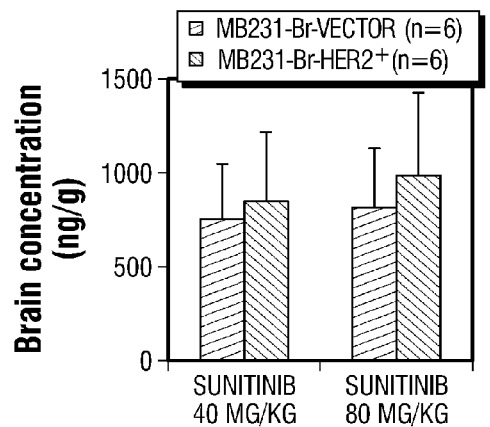
Figures 4, 9A:
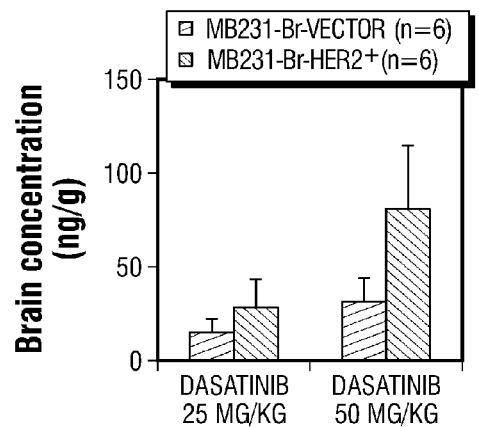
Figures 5, 9A:
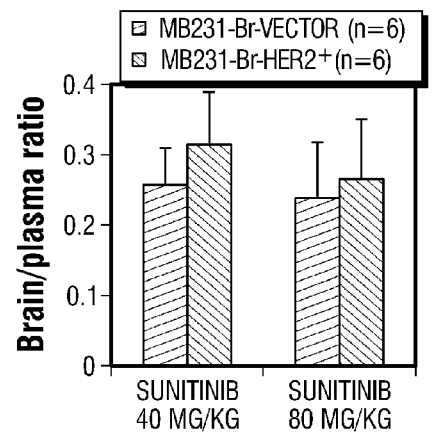
Figures 6, 9A:
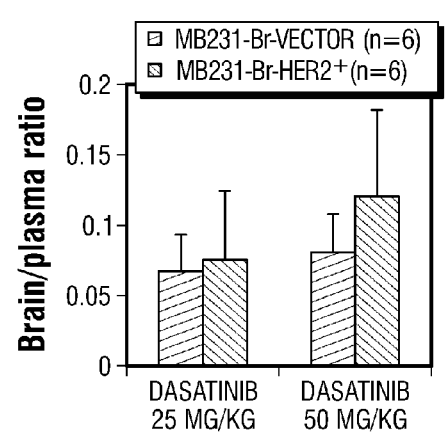
Figure 9B:
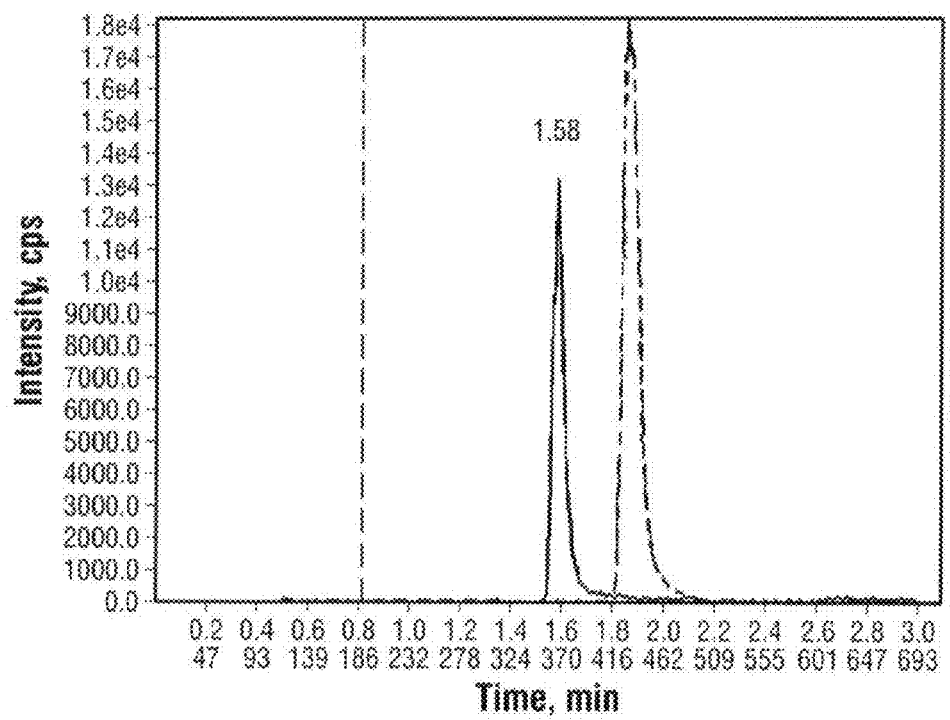
Figure 9C:
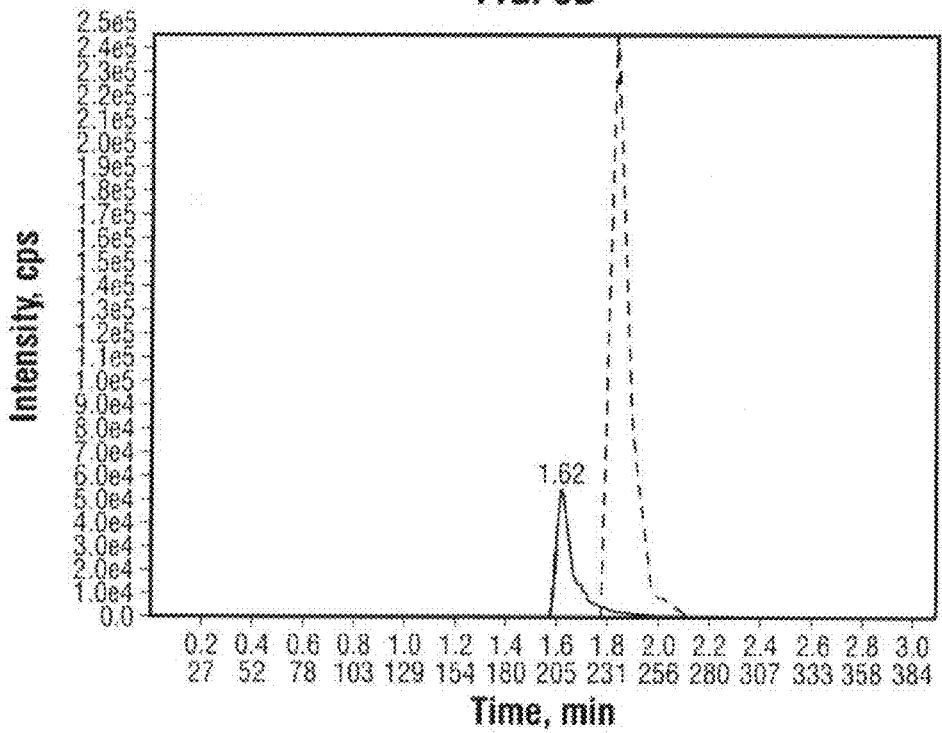
Figure 10A:
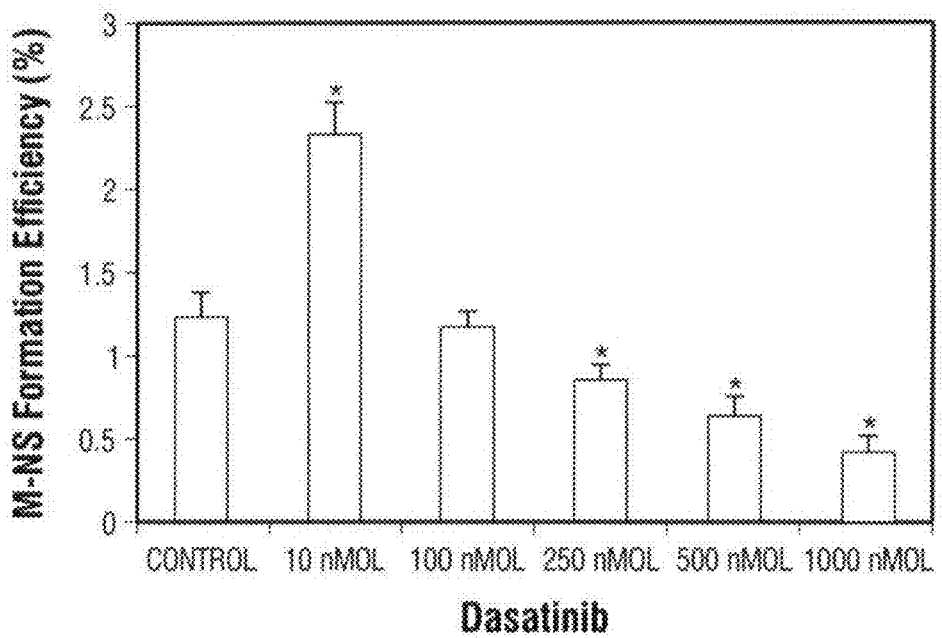
FIG. 10A and FIG. 10B show in vitro second mammo-neurosphere formation efficiency of dasatinib and sunitinib. *p<0.05 vs control; **p<0.01 vs control.
Figure 10B:
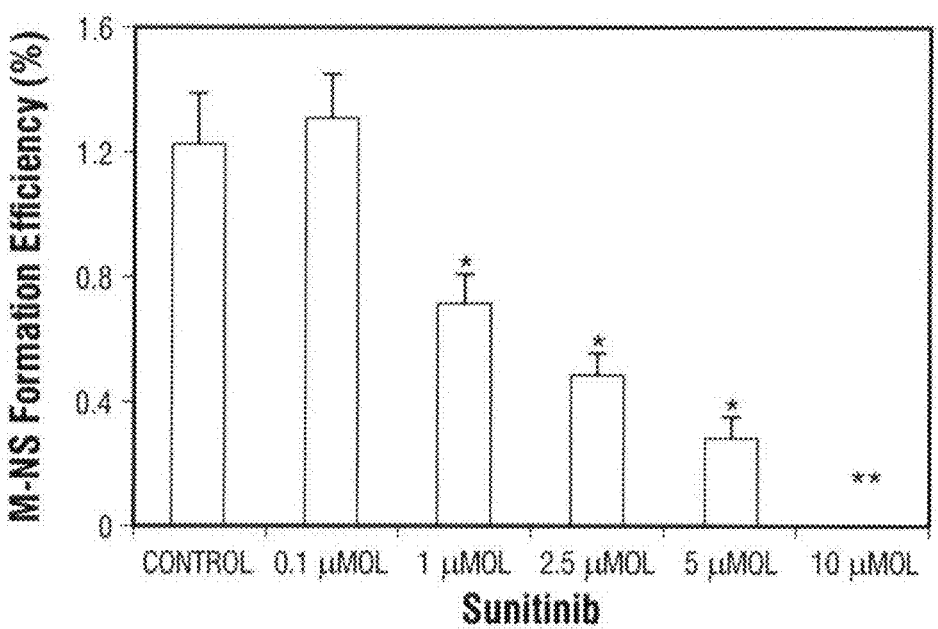

Before investigating the efficacy of sunitinib and dasatinib on BCBM animal models, the role of their targets was evaluated in mediating the transmigration through in vitro blood-brain barrier (BBB) of the brain metastatic breast cancer cell lines. An in vitro BBB model was used, which included human primary brain microvascular endothelial cells (BMECs) and astrocytes, which forms a tight barrier that lacks the permeability to albumin (FIG. 8). The ability to pass through the in vitro BBB of MB231-BR and MB231-BR-HER2 was significantly decreased by RNA interference (RNAi)-mediated knockdown of RET, KDR, and FYN expression (FIG. 2B and FIG. 2C). Drug treatment by sunitinib and dasatinib to inhibit the phosphorylation of KDR, RET and FYN proteins, as well as the downstream pathway proteins, inhibited the cell migration and invasion in a dose-dependent manner (FIG. 2D, FIG. 2E, and FIG. 2F).

Figures 1, 3A:
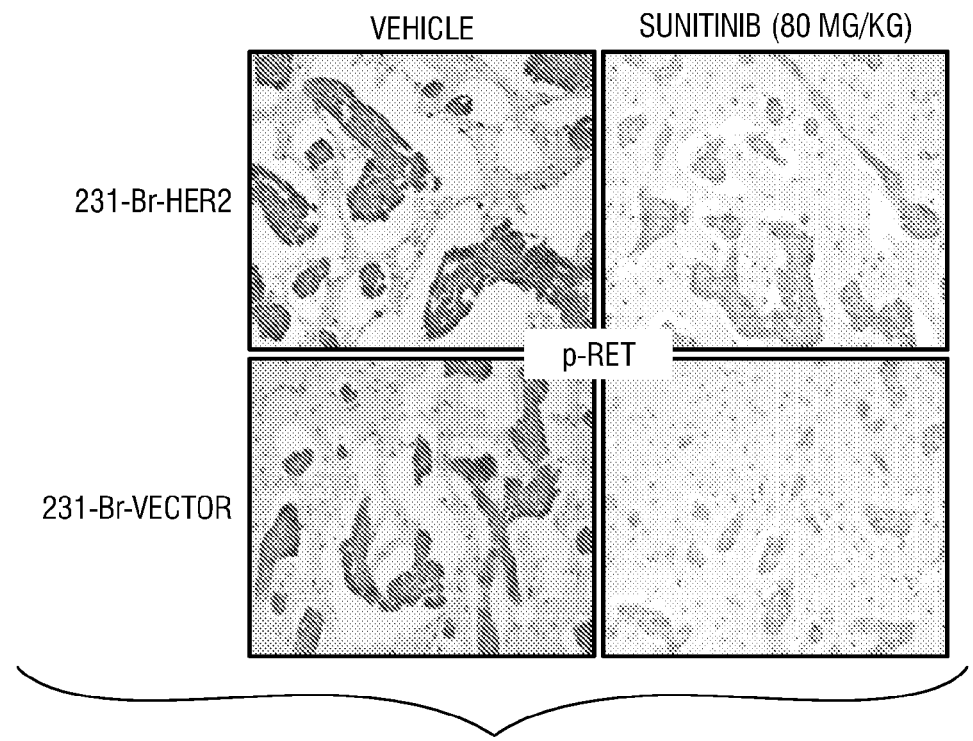
Figures 2, 3A:
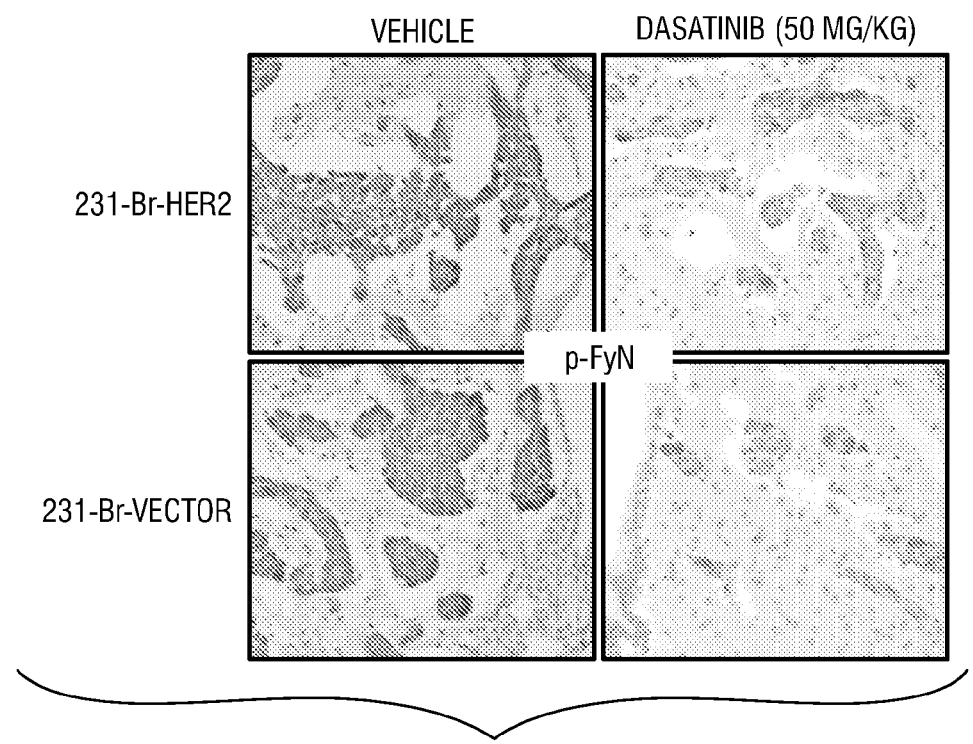

The brain distribution of the two drugs in MB231-BR and MB231-BR-HER2 was further examined in brain metastatic xenografts. After the brain metastases were established for two weeks, the animals were orally given the sunitinib and dasatinib once daily for 14 days, which is the time that the drug concentration in plasma reach to steady state (Atkins et al., 2006). The blood and whole brain of the mice were harvested six hours after the last treatment and the drug concentrations were measured by HPLC-MS/MS. The brain-to-plasma ratios for sunitinib ranged from 0.24-0.31 and dasatinib 0.06-0.12 in the brain metastatic xenografts (FIG. 9A-1, FIG. 9A-2, FIG. 9A-3, FIG. 9A-4, FIG. 9A-5, FIG. 9A-6, FIG. 9B, and FIG. 9C). Furthermore, both sunitinib and dasatinib effectively inhibited their respective targets in brain metastases tissues, as evidenced by immunohistochemistry analysis for pRET and pFYN (FIG. 3A-1 and FIG. 3A-2). These results indicated that both of the two drugs achieve certain pharmacological concentrations in the brain metastases of breast cancer xenografts.

Efficacy of Sunitinib and Dasatinib in Inhibiting Brain Metastasis In Vivo.

Recent studies show that triple-negative breast cancers (TNBC), which refer to ER−, PR− and HER2−, are more likely to develop brain metastasis (Fulford et al., 2007; Smid et al., 2008; Lin et al., 2008; Neman et al., 2010). Association of the BCBM-GNS status with brain relapse is significant within ER−, PR−, and HER2− tumors in both early stage and local advanced tumors. However, it was also found that the signature was significantly associated with ER+, PR+, and HER2+ in early stage tumors. Studies also presented HER2 expression trends from resected human brain metastases and data from an experimental brain metastasis assay, indicate a functional contribution of HER2 to brain metastatic colonization (Tham et al., 2006; Hicks et al., 2006; Palmieri et al., 2007). Both HER2 over-expressing 231-BR cell line as HER2+ xenograft model[51], and 231-BR as triple negative model (Shapira et al., 2006; Chang et al., 2007) were used to test the drug efficacy. Three days after intracardiac injection of the tumor cells, mice were randomly assigned to receive sunitinib (40 or 80 mg/kg body weight) or dasatinib (25 or 50 mg/kg body weight) or vehicle solution once daily by oral gavage (n=14-19 mice per group). Mice received 28 days treatment, and all mice were sacrificed, and brains were harvested for ex vivo whole-brain fluorescent imaging of EGFP-positive brain metastases. In general, there were obviously less EGFP-positive loci in each of the two drug-treated groups as compared with the vehicle control in both the HER2+ and triple negative models (FIG. 3B-1 and FIG. 3B-2 and FIG. 3D-1 and FIG. 3D-2).

Figure 3C:
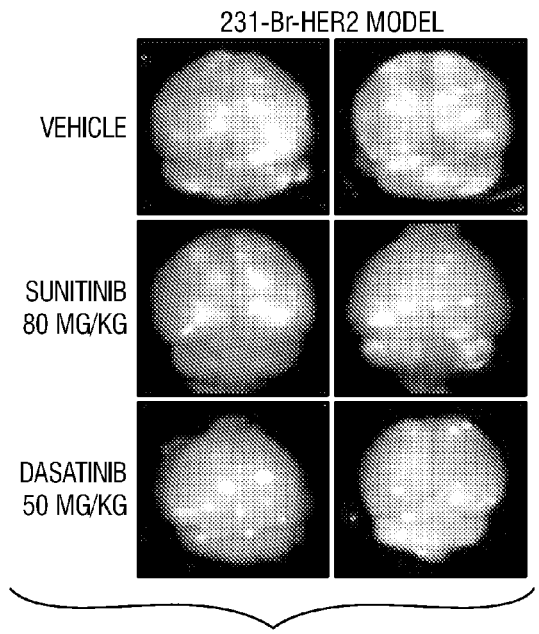
Figure 3C:
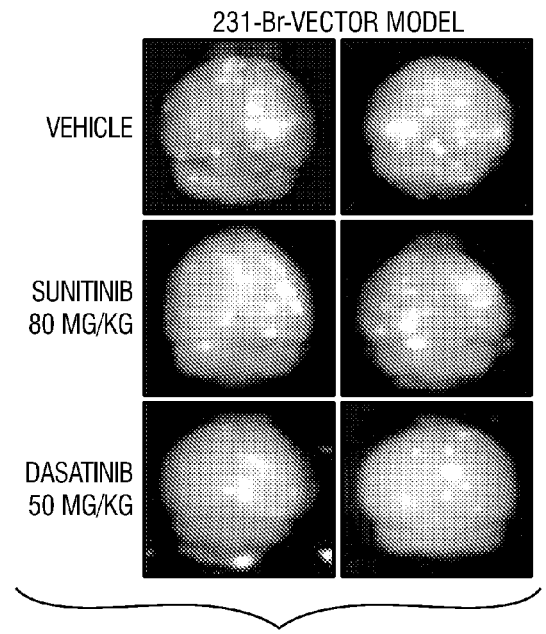
Figure 3C:
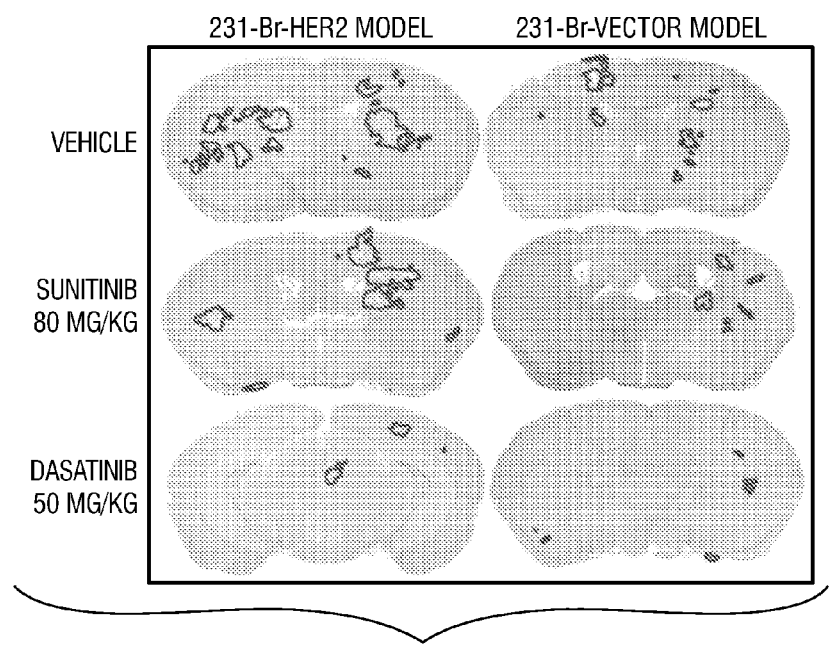
Figures 1, 3D:
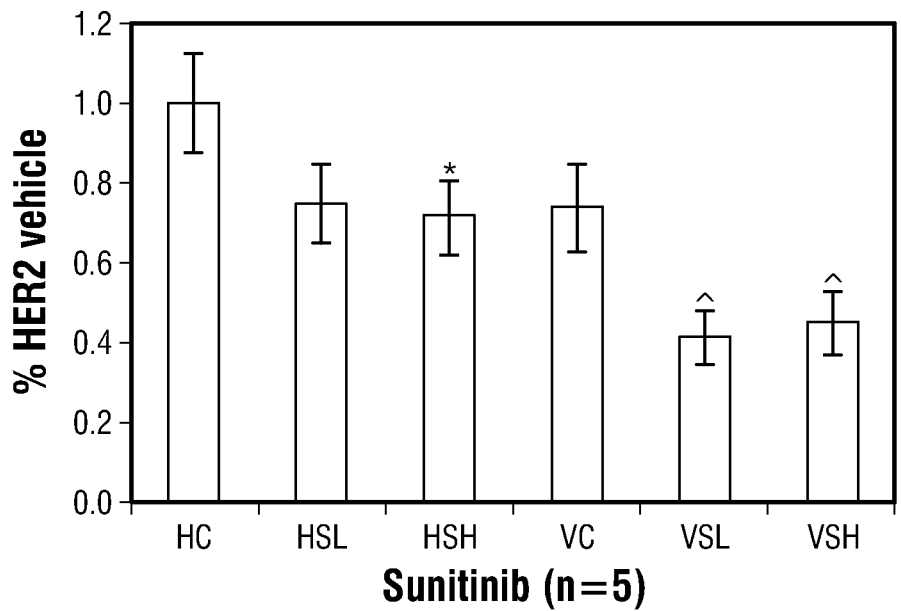
Figures 2, 3D:
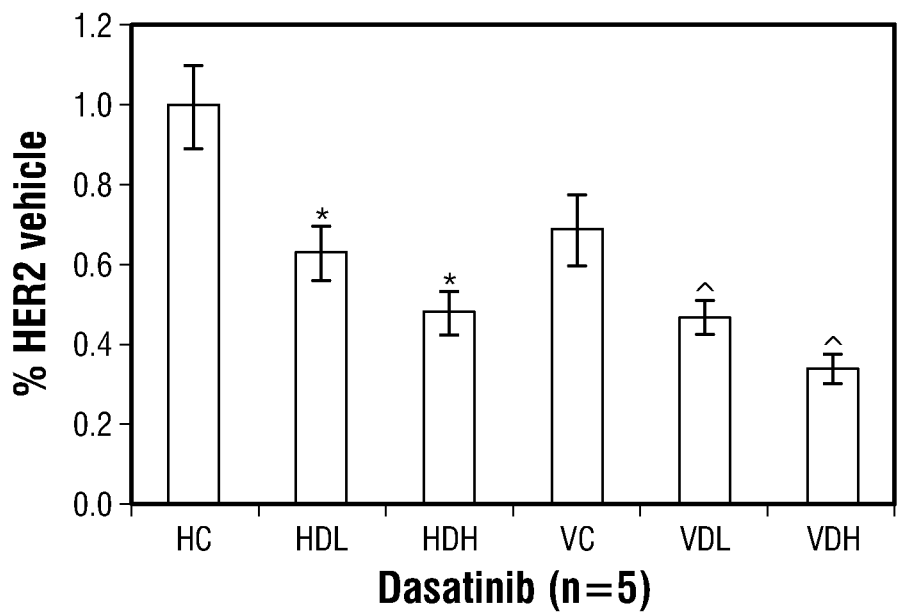
Figures 1, 4A:
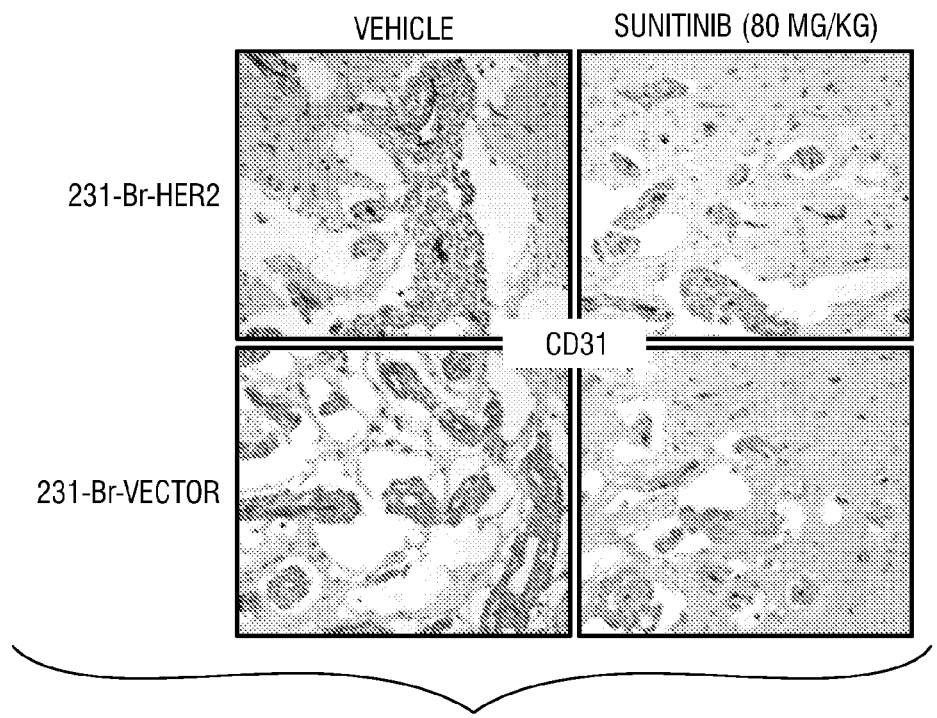
Figures 2, 4A:
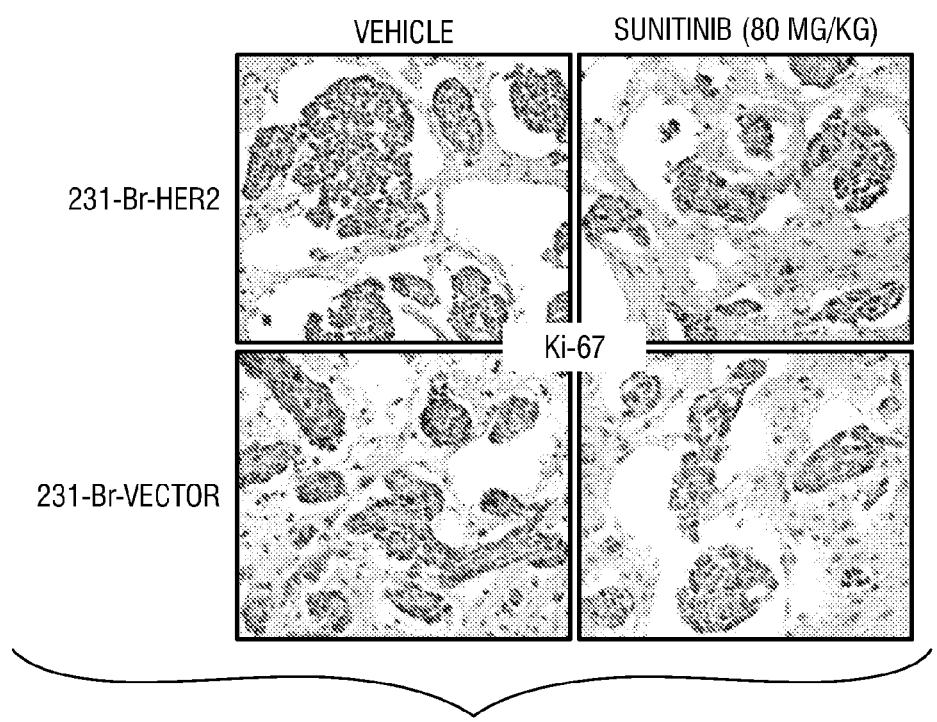
Figures 3, 4A:
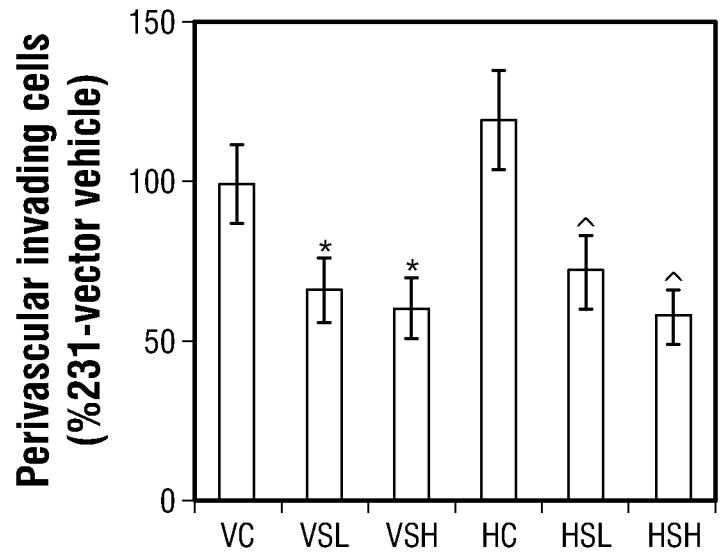
Figures 4, 4A:
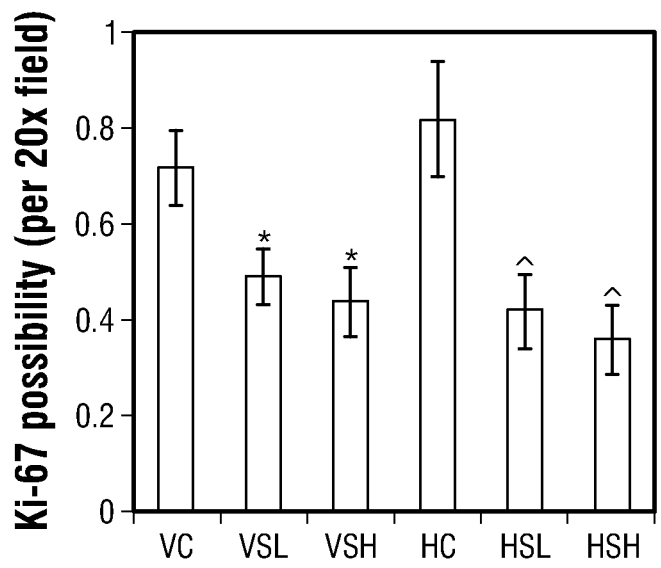
Figures 1, 4B:
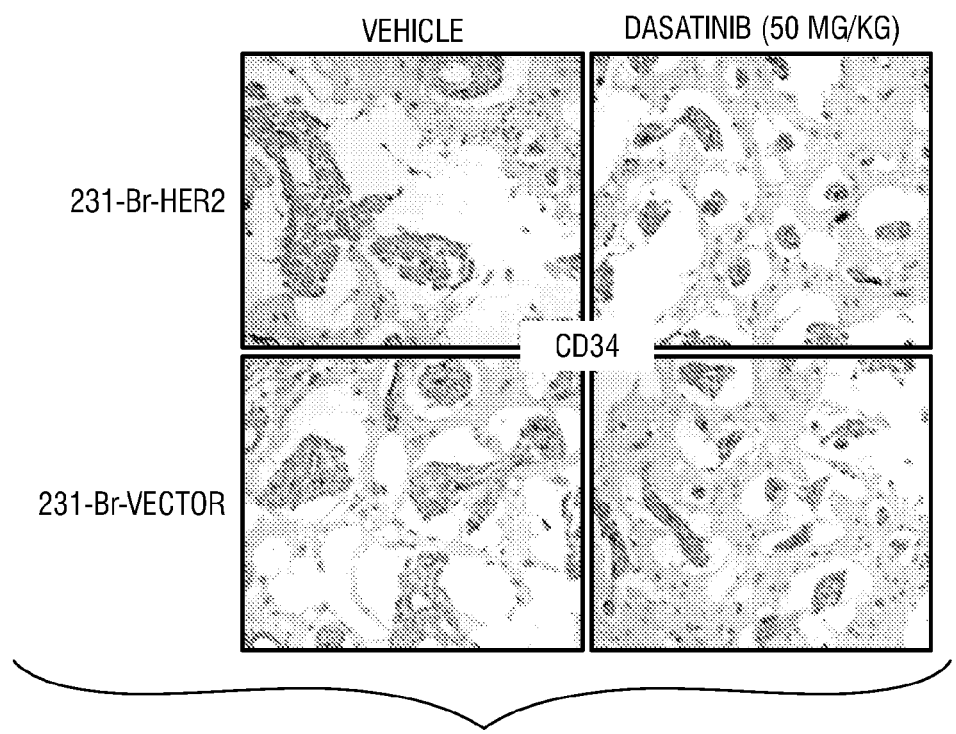
Figures 2, 4B:
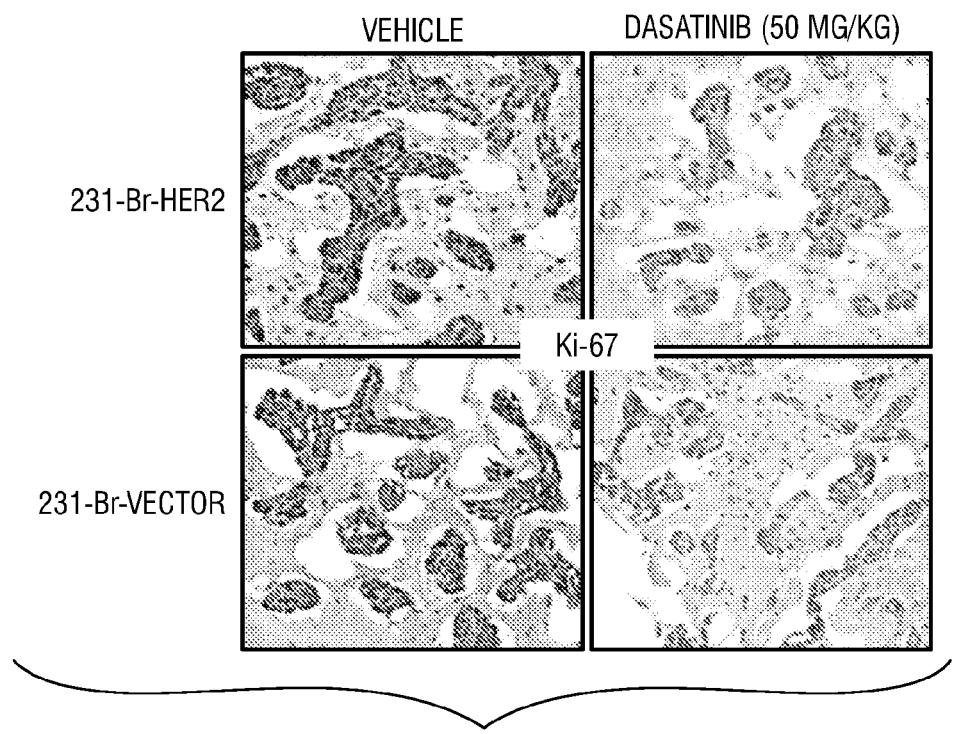
Figures 3, 4B:
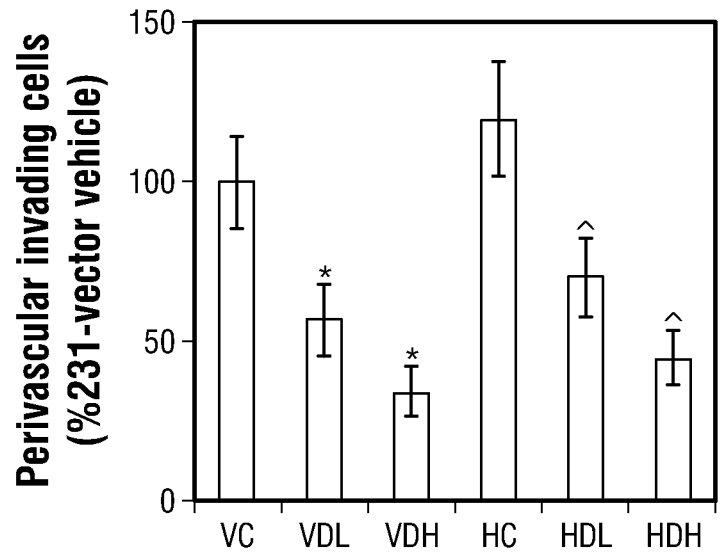
Figures 4, 4B:
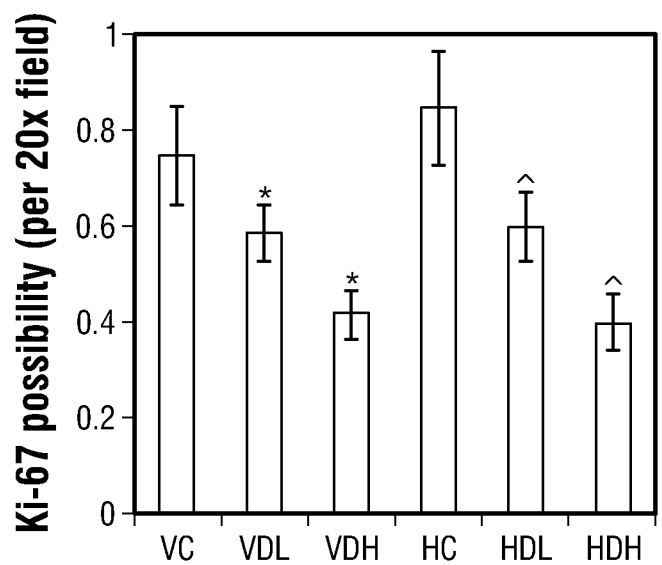

To quantify the effects of sunitinib and dasatinib on brain metastasis, a computerized imaging analysis algorithm (Zhao et al., 2011) was developed to count the number and area of large metastatic lesions (>50 $\mu m^2$) and the number of micrometastasis (≤50 $\mu m^2$) in H&E-stained brain sections (FIG. 3C and Table 2) automatically.

TABLE 2

Sunitinib and Dasatinib inhibit brain metastasis in 231-BR models, cons

| | | 231-BR-HER2 model | | | | | 231-BR-vector model | | | |
|---|---|---|---|---|---|---|---|---|---|---|
| Treatment | n | large metastases # | p | Micro metastases # | p | n | large metastases # | p | Micro metastases # | p |
| vehicle | 18 | 20.2 ± 2.7 | | 293.6 ± 38.5 | | 19 | 14.8 ± 2.8 | | 218.3 ± 33 | |
| Sunitinib 40 mg/kg | 16 | 15.6 ± 1.9 | 0.046 | 228.1 ± 28.3 | 0.067 | 17 | 11.8 ± 2.0 | 0.075 | 156.1 ± 25 | 0.049 |
| Sunitinib 80 mg/kg | 17 | 15.2 ± 2.1 | 0.048 | 199.8 ± 24.1 | 0.043 | 16 | 10.2 ± 1.3 | 0.045 | 150.2 ± 22 | 0.047 |
| Dasatinib 25 mg/kg | 15 | 12.5 ± 1.8 | 0.035 | 175.7 ± 27.8 | 0.041 | 18 | 8.6 ± 1.5 | 0.031 | 144.6 ± 12.5 | 0.012 |
| Dasatinib 50 mg/kg | 14 | 8.7 ± 1.6 | 0.026 | 113.2 ± 23.8 | 0.019 | 16 | 7.5 ± 1.3 | 0.029 | 99.5 ± 10.3 | 0.009 |

* Mice were injected with $1.75 \times 10^5$ 231-BR-HER2 or 231-BR-vector cells through the left ventricle, and treated with low-dose or high-dose of sunitinib, dasatinib, or vehicle started 3 days later. The treatment was performed once daily for 28 days. Number and area of metastases were determined in 30 step-sections from the mouse brains described in Materials and Methods Among mice injected with 231-BR-vector cells, those treated with 80 mg sunitinib/kg body weight had 31% fewer large metastasis than those treated with vehicle (p<0.05), whereas treatment with 40 mg sunitinib/kg body weight had fewer large metastasis than those treated with vehicle but not with statistical difference. For dasatinib treatment, 41.9-49.3% fewer large metastases were detected in the 25 or 50 mg dasatinib/kg treated mice than vehicle group (p<0.05). In terms of micrometastases, mice treated with 40 or 80 mg sunitinib/kg body weight had 28.5-31.3% fewer micrometastases, and mice treated with 25 or 50 mg dasatinib/kg body weight had 33.8-54.4% fewer micrometastases than vehicle-treated mice (p<0.05). Among mice injected with 231-BR-HER2 cells, those treated with 40 or 80 mg sunitinib/kg body weight had 22.7-24.8% fewer large metastases, and mice treated with 25 or 50 mg dasatinib/kg body weight had 38.1-56.9% fewer large metastases than those treated with vehicle (p<0.05). There were 22.3-31.9% and 40.2-61.4% fewer micrometastases in mice treated with 40 or 80 mg sunitinib/kg body weight and 25 or 50 dasatinib/kg body weight, respectively, compared with than vehicle treated mice (p<0.05). These data indicate that sunitinib and dasatinib suppressed the colonization and outgrowth of brain metastasis at both doses tested. However, an insignificant difference was observed in the two drugs' effects on 231-BR-vector and 231-BR-HER2 models.

To discover the possible mechanism of sunitinib and dasatinib on metastases in vivo, their effects on a) tumor cell perivasvular invasion, b) tumor cell proliferation and apoptosis, and c) angiogenesis were examined. With CD31 staining, a single endothelial cell or a cluster of endothelial cells positive for CD31 was considered a vessel. Perivascular invasive cells, counted as the number of cells in the metastatic lesion tightly associated with vessels, were significantly decreased by both of the two drugs under two doses on the two xenograft models (FIG. 4A-1, FIG. 4A-2, FIG. 4A-3, FIG. 4A-4, FIG. 4B-1, FIG. 4B-2, FIG. 4B-3 and FIG. 4B-4). The percentage of Ki67-positive cells in the tumor section showed notable decreases in the sunitinib and dasatinib-treated groups (FIG. 4A-1, FIG. 4A-2, FIG. 4A-3, FIG. 4A-4, FIG. 4B-1, FIG. 4B-2, FIG. 4B-3 and FIG. 4B-4). Apoptosis as measured by TUNEL, was rarely detected in the tumor section in all groups. The number of microvessels in big metastatic lesions was not significantly changed in the sunitinib treatment groups compared with vehicle group, but it was noticed there were less enlarged size and tortuous vessels within the metastasis lesions, and the lesion-surrounding edema areas were significantly less in the 40 mg and 80 mg sunitinib/kg-treated mice than the vehicle-treated mice (FIG. 4A-1, FIG. 4A-2, FIG. 4A-3, FIG. 4A-4, and FIG. 10A and FIG. 10B).

Sunitinib and Dasatinib Inhibit the Mammo-Neurosphere-Initiating Cells Reside in the Brain Metastatic Lesions.

Recent studies indicate that the molecular machinery for cancer invasion and metastasis is similar to that involved in the activation, mobilization, and homing of normal stem cells (Lapidot and Kollet, 2002; Kang et al., 2005; Kaplan et al., 2005; Dewan et al., 2006). In addition, despite extensive intratumor heterogeneity, comparison of paired samples of primary tumors and autologous lymph node and/or distant-site metastases usually reveals striking similarities on tissue morphology, repertoire of somatic genetic mutations, expression of tumor-suppressor and immunomodulatory proteins, expression of epigenetically controlled genes, and overall transcriptional profile as defined by gene expression arrays (as reviewed in Dalerba et al., 2007), thus tumor-initiating cells (TICs) are proposed to be responsible for metastasis (Marotta and Polyak, 2009; Li and Neaves, 2006). In attempt to explore the possible role of TICs in brain metastasis and more important the therapeutic strategy based on the TICs-metastasis theory, published breast TICs microarray datasets (GSE7513 and GSE7515) were used to explore possible drugs that may target a TICs network signature, and both sunitinib and dasatinib stood out as candidate drugs through our analysis.

Figures 1, 5A:
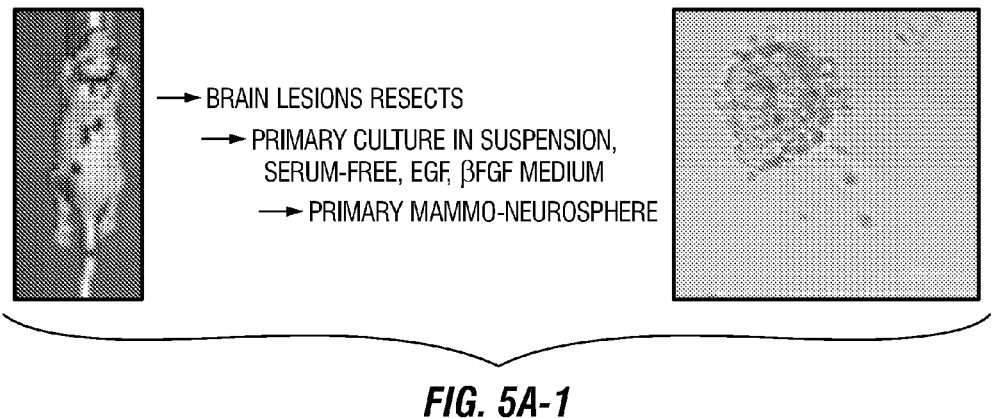
Figures 2, 5A:
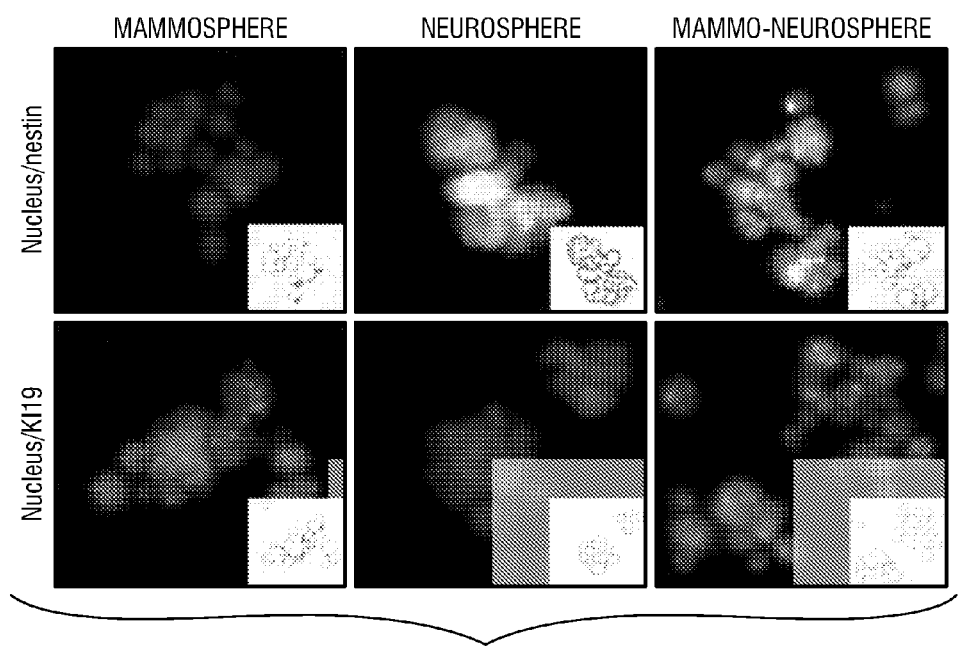

To determine whether these two drugs inhibited the brain tropism TICs, brain metastatic cells from the brain lesions of 231-BR brain metastatic mice were cultured in non-adherent mammosphere culture condition (Grimshaw et al., 2008) to form mammo-neurospheres. It was found that these cells were capable of forming spheres that could be passaged, and were human keratin-19 (Alix-Panabieres et al., 2009) and nestin positive (FIG. 5A1 and FIG. 5A-2). A majority of the sphere cells were CD44$^+$/CD24$^-$ and CD133$^+$ (FIG. 5B-1 and FIG. 5B-2). After dissociation and plating with serum onto adherent dishes, the cells can differentiate, as determined by the increased expression of cytokeratin 5 and 18 (FIG. 5B-1 and FIG. 5B-2). By injecting the same number ($1.75 \times 10^5$) of sphere-dissociated cells and 231-BR cells to the mouse left ventricle, the sphere derived cells induced earlier initiation of brain metastasis than the 231-BR cells (p<0.01) (FIG. 5D), as monitored by non-invasive bioluminescent imaging.

Figure 5C:
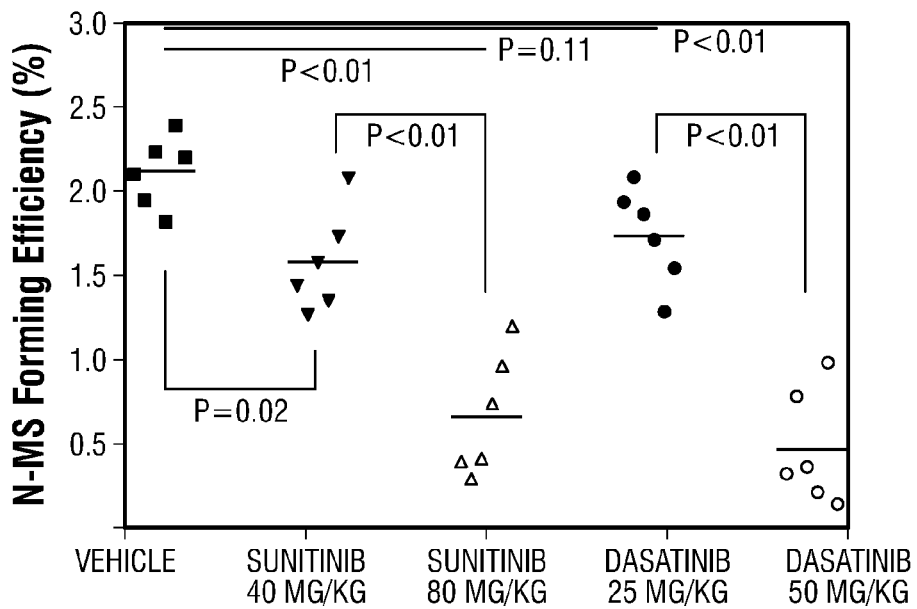
Figure 5D:
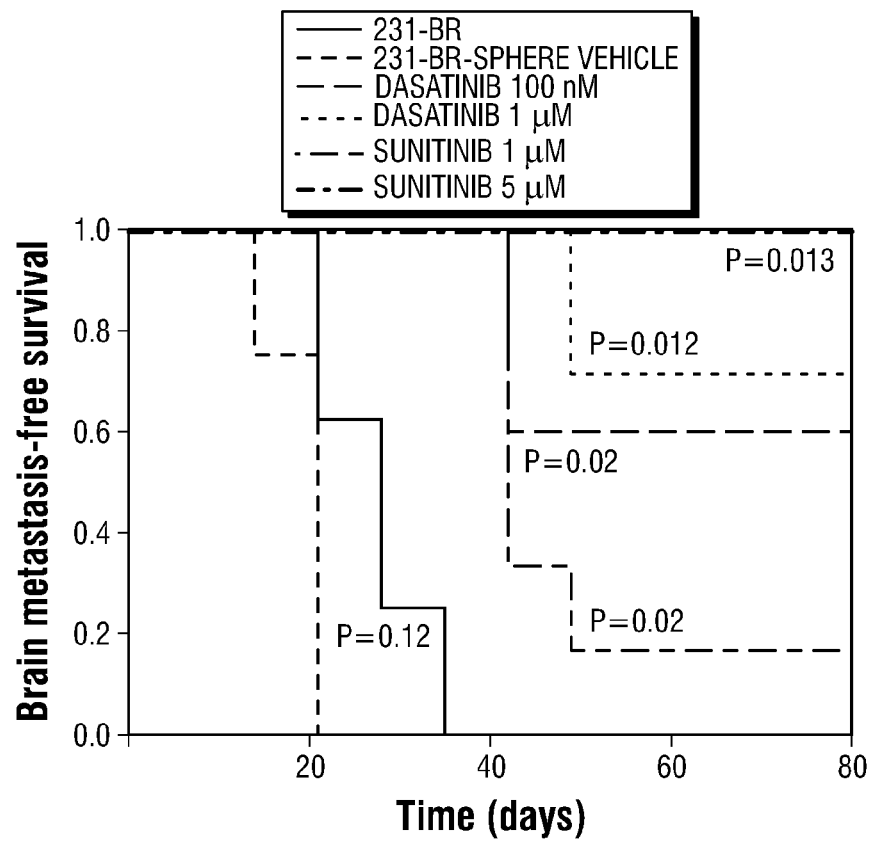
Figures 5, 6A:
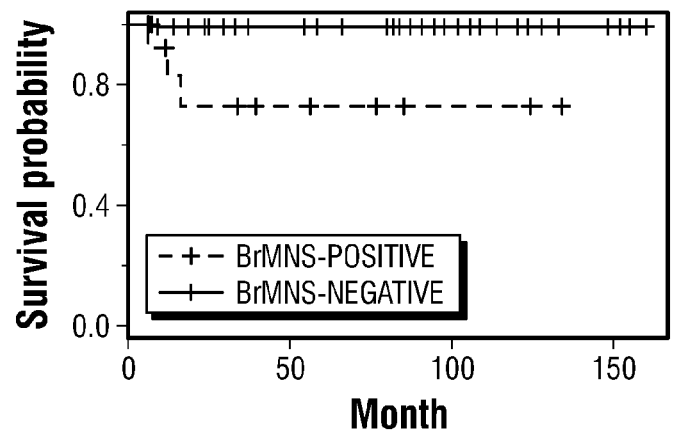
Figures 6, 6A:
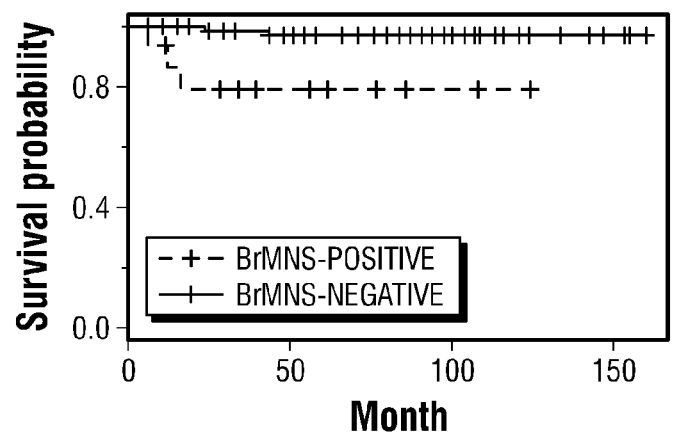
Figures 6, 6A, 7:
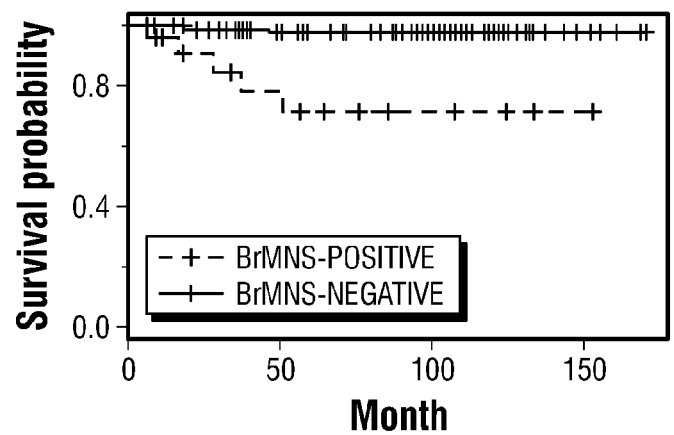
Figures 1, 6C:
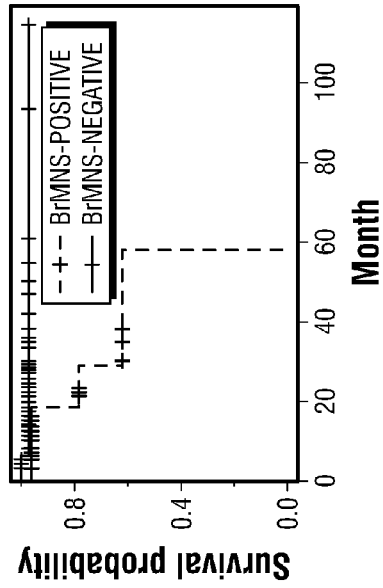
Figures 3, 6C:
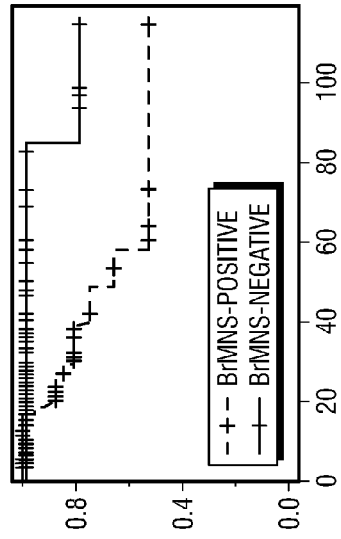
Figures 2, 6C:
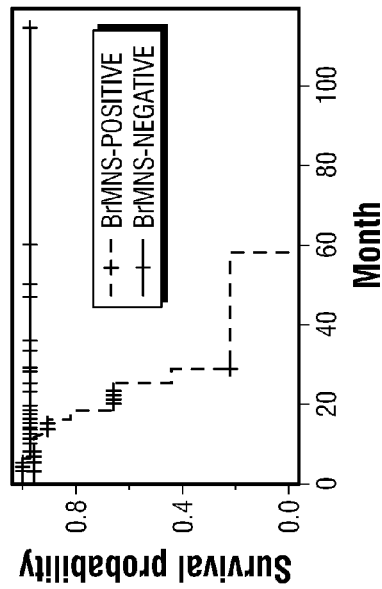

After the brain metastases were established for two weeks, the animals were orally given the sunitinib and dasatinib once daily for 14 days, at which the two drugs achieved certain pharmacological concentrations in the brain metastatic lesions. When taking the brain lesions for mammo-neurosphere culture, both sunitinib and dasatinib reduced the secondary MSFE compared to vehicle control (p<0.05) (FIG. 5C). Animal transplant experiments were also carried out to assess the in vivo brain metastasis formation ability of sphere-dissociated cells after drug treatment in vitro for 48 hours. For control cells treated with DMSO, all the injections resulted in brain metastasis formation when $1.75 \times 10^5$ cells were injected. When the cells were treated with sunitinib (1 µM and 5 µM) or dasatinib (100 nM and 1 µM), the brain metastases formation was significantly decreased in the mice (p<0.01), and most strikingly, 5 µM sunitinib treatment resulted in no detectable brain metastasis in 15 mice till 70-days post injection (FIG. 5D). These data highlighted a new mechanism for sunitinib and dasatinib to inhibit the brain tropism TICs, and thus inhibit the brain metastasis.

TABLE 3

31-GENE SIGNATURE FOR PREDICTING BRAIN METASTATIC BREAST CANCER

| | Gene Name | Full Name | Function |
|---|---|---|---|
| 1 | MBD1 | methyl-CpG binding domain protein 1 | Transcriptional repressor that binds CpG islands in promoters where the DNA is methylated at position 5 of cytosine within CpG dinucleotides. |
| 2 | NFKBIB | nuclear factor of kappa light polypeptide gene enhancer in B-cells inhibitor beta | Inhibits NF-kappa-B by complexing with and trapping it in the cytoplasm |
| 3 | SEC16A | SEC16 homolog A | Defines endoplasmic reticulum exit sites (ERES) and is required for secretory cargo traffic from the endoplasmic reticulum to the Golgi apparatus. |
| 4 | IKBKG | inhibitor of kappa light polypeptide gene enhancer in B-cells, kinase gamma | This gene encodes the regulatory subunit of the inhibitor of kappaB kinase (IKK) complex, which activates NF-kappaB resulting in activation of genes involved in inflammation, immunity, cell survival, and other pathways. |
| 5 | MAP3K3 | mitogen-activated protein kinase kinase kinase 3 | Component of a protein kinase signal transduction cascade. Mediates activation of the NF-kappa-B, AP1 and DDIT3 transcriptional regulators |
| 6 | SUV39H1 | suppressor of variegation 3-9 homolog 1 | Histone methyltransferase that specifically trimethylates 'Lys-9' of histone H3 using monomethylated H3 'Lys-9' as substrate |
| 7 | RAF1 | v-raf-1 murine leukemia viral oncogene homolog | Involved in the transduction of mitogenic signals from the cell membrane to the nucleus. Part of the Ras-dependent signaling pathway from receptors to the nucleus. Protects cells from apoptosis mediated by STK3 |
| 8 | PHGDH | phosphoglycerate dehydrogenase | catalyzes the transition of 3-phosphoglycerate into 3-phosphohydroxypyruvate, which is the first and rate-limiting step in the phosphorylated pathway of serine biosynthesis |
| 9 | RET | ret proto-oncogene | receptor with tyrosine-protein kinase activity; important for development |
| 10 | KIAA1967 | KIAA1967 | Inhibits SIRT1 deacetylase activity leading to increasing levels of p53/TP53 acetylation and p53-mediated apoptosis. Inhibits SUV39H1 methyltransferase activity |
| 11 | NCK1 | NCK adaptor protein 1 | Adapter protein which associates with tyrosine-phosphorylated growth factor receptors or their cellular substrates. Maintains low levels of EIF2S1 phosphorylation by promoting its dephosphorylation by PP1. Plays a role in the DNA damage response |
| 12 | NFKB1 | nuclear factor of kappa light polypeptide gene enhancer in B-cells | is involved in many biological processed such as inflammation, immunity, differentiation, cell growth, tumorigenesis and apoptosis |
| 13 | REL | v-rel reticuloendotheliosis viral oncogene homolog | Proto-oncogene that may play a role in differentiation and lymphopoiesis. |
| 14 | KDR | vascular endothelial growth factor receptor 2 | Receptor for VEGF or VEGFC. Has a tyrosine-protein kinase activity. The VEGF-kinase ligand/receptor signaling system plays a key role in vascular development and regulation of vascular permeability. |
| 15 | IQGAP2 | IQ motif containing GTPase activating protein 2 | Binds to activated CDC42 and RAC1 but does not seem to stimulate their GTPase activity. Associates with calmodulin |
| 16 | FBL | fibrillarin | Involved in pre-rRNA processing |
| 17 | IKBKB | inhibitor of kappa light polypeptide gene enhancer in B-cells, kinase beta | Acts as part of the IKK complex in the conventional pathway of NF-kappa-B activation and phosphorylates inhibitors of NF-kappa-B thus leading to the dissociation of the inhibitor/NF-kappa-B complex and |

TABLE 3-continued

31-GENE SIGNATURE FOR PREDICTING BRAIN METASTATIC BREAST CANCER

| | Gene Name | Full Name | Function |
|---|---|---|---|
| 28 | FYN | FYN oncogene related to SRC, FGR, YES | ultimately the degradation of the inhibitor Src kinases consist of eight non-receptor tyrosine kinases (Src, Fyn, Yes, Lck, Lyn, Hck, Fgr and Blk) that interact with the intracellular domains of growth factor/cytokine receptors, GPCRs and integrins |
| 29 | AKAP8L | A kinase (PRKA) anchor protein 8-like | involved in nuclear envelope breakdown and chromatin condensation. May regulate the initiation phase of DNA replication when associated with TMPO-beta |
| 20 | RELA | v-rel reticuloendotheliosis viral oncogene homolog A | involved in many biological processed such as inflammation, immunity, differentiation, cell growth, tumorigenesis and apoptosis |
| 21 | KHDRBS1 | p21 Ras GTPase-activating protein-associated p62 | Recruited and tyrosine phosphorylated by several receptor systems, for example the T-cell, leptin and insulin receptors. Once hosphorylated, functions as an adapter protein in signal transduction cascades by binding to SH2 and SH3 domain-containing proteins. Role in G2-M progression in the cell cycle. |
| 22 | GRB7 | growth factor receptor-bound protein 7 | Interacts with the cytoplasmic domain of the epidermal growth factor receptor which is then inhibited |
| 23 | E2F1 | E2F transcription factor 1 | Transcription activator that binds DNA cooperatively with dp proteins through the E2 recognition site, 5'-TTTC[CG]CGC-3' found in the promoter region of a number of genes whose products are involved in cell cycle regulation or in DNA replication. |
| 24 | HDAC1 | histone deacetylase 1 | Responsible for the deacetylation of lysine residues on the N-terminal part of the core histones (H2A, H2B, H3 and H4). Histone deacetylation gives a tag for epigenetic repression and plays an important role in transcriptional regulation, cell cycle progression and developmental events. |
| 25 | HDAC2 | histone deacetylase 2 | Responsible for the deacetylation of lysine residues on the N-terminal part of the core histones (H2A, H2B, H3 and H4). Histone deacetylation gives a tag for epigenetic repression and plays an important role in transcriptional regulation, cell cycle progression and developmental events. |
| 26 | WIPF1 | Wiskott-Aldrich syndrome protein interacting protein | have direct activity on the actin cytoskeleton. Induces actin polymerization and redistribution. |
| 27 | GRB2 | growth factor receptor-bound protein 2 | Adapter protein that provides a critical link between cell surface growth factor receptors and the Ras signaling pathway |
| 28 | CCT8 | T-complex protein 1, theta subunit | Molecular chaperone; assists the folding of proteins upon ATP hydrolysis |
| 29 | ATP5A1 | ATP synthase alpha chain, mitochondrial | Mitochondrial membrane ATP synthase produces ATP from ADP in the presence of a proton gradient across the membrane which is generated by electron transport complexes of the respiratory chain. |
| 30 | VIM | vimentin | Vimentins are class-III intermediate filaments found in various non-epithelial cells, especially mesenchymal cells |
| 31 | YWHAB | brain protein 14-3-3, beta isoform | 14.3.3 proteins are a group of highly conserved proteins that are involved in many vital cellular processes such as metabolism, protein trafficking, signal transduction, apoptosis and cell cycle regulation |

Discussion

The present method provides an improved strategy for drug repositioning by identifying a network-based biomarker signature to guide drug target identification, and perform a systems testing on preclinical models for the drug efficacy. In genomics, the biomarker challenge is to identify unique molecular signatures in complex biological mixtures that can be unambiguously correlated to biological events in order to validate novel drug targets and predict drug responses. Applying biomarkers for drug repositioning is especially valuable, as they would help to prioritize drug discovery resources by enabling proof-of-concept studies for using known drugs to target novel therapeutic targets. However, most cancer gene signature studies are focused on identifying individual genes, which are mostly changed in the occurrence of cancer events. In doing so, the complex biological interactions of molecules are neglected. Moreover, these methods also miss less changed genes that are not considered to be a part of the identified gene signature. Recently, gene expression signatures have been shown to identify patterns of pathway deregulation in tumors and thus pathway signatures have been explored in human cancers as a guide to targeted therapies (Bild et al., 2006). Currently, the cancer signaling pathway information is far less comprehensive, thus CSBs were applied to expand the existing pathways for constructing more comprehensive pathways maps and identify the network-based biomarker signature. The panel of biomarkers with native interactions among them in a small-scale network is more relevant to biological events than single gene biomarker, and in this study, it demonstrated promising value in prognosis prediction and drug target discovery.

Overall, the expression pattern of the 31 genes assembled by multiple 5-gene short paths predicted for patients at high risk for brain relapse in the 612 clinical annotated cohorts. Furthermore, among the 31 genes identified in the initial signature, three of them encode critical receptor tyrosine kinase, which play important roles in cancer and neurodendocrine and neuronal functions, i.e., RET, Fyn and KDR, have been examined in preclinical studies, and may serve as potential biomarkers to guide drug treatment with compounds such as sunitinib and dasatinib. The expression of RET, Fyn and KDR was examined in total 612 primary breast tissue microarray with 42 brain metastasis cases, and validated their high expressions by RT-PCR in 20 primary breast tissue with 11 brain metastasis cases. Preclinical study results demonstrated that sunitinib and dasatinib both inhibit brain metastasis in animal models, and targeting of these these proteins provides compelling evidence that they may be useful in prioritizing sunitinib and dasatinib on primary breast cancer patients with high risk of brain relapse.

RET is expressed in discrete subsets of neurons in the central and peripheral nervous systems (Arighi et al., 2005). RET gain-of-function mutations result in multiple endocrine neoplasia type 2. Recent evidence demonstrate a potentially important role for RET in breast cancer (Morandi et al., 2011). While, similar to other tyrosine kinases, RET mutations are rarely identified in breast cancer (Kan et al., 2010), RET over-expression with a corresponding increase in protein levels is detected in invasive breast cancers (Esseghir et al., 2007; Plaza-Menacho et al. 2010). Additionally, RET-dependent Glial cell line-derived neurotrophic factor signaling in breast cancer cell lines causes increased cell scattering and anchorage-independent proliferation (Esseghir et al., 2007). RET rearrangements were also detected in high-grade invasive ductal breast cancers (Unger et al., 2010), and furthermore expression of the thyroid cancer-associated RET/PTC1 fusion protein led to mammary gland carcinoma in 18% of transgenic mice (Portella et al., 1996). RET signaling has also been implicated in breast cancer tamoxifen resistance, potentially through estrogen receptor1α phosphorylation causing ligand-independent transcriptional regulation (Morandi et al., 2011). These data strongly suggest a role for RET in breast cancer progression. Although there are no specific RET inhibitors, several small molecule tyrosine kinase inhibitors (TKIs) have activity against RET (Zuercher et al., 2010). Motesanib, sorafenib, sunitinib and vandetanib are all small molecule TKIs that target VEGFRs, RET that are effective at nanomolar concentrations. They have been shown effective alone or in combination with chemotherapy in vivo in various models of breast cancer (Murray et al., 2003), but the data from multiple phase II and III clinical trials have been controversial in their reported antitumor activity, as there has been no selection for patients whose breast cancers show RET overexpression or active RET signaling. Due to the encouraging efficacy result of sunitinib on RCC brain metastasis, and its satisfactory brain distribution in the animal models, sunitinib was selected to treat breast cancer brain metastasis animals in the present example. Sunitinib is also being evaluated as a potential treatment of advanced breast cancer in combination with chemotherapeutic agents both in the adjuvant and neoadjuvant setting. Impressively, in addition to the above TKIs, XL-184, an oral small-molecule TKI that targets KDR, c-Met and RET, has recently been reported that out of 68 brain metastases patients been treat with XL-184, 59 showed a partial or complete response, notable, the response was accompanied by symptom improvement.

Owing to the structural similarity between RTKs, all of these TKIs, including sunitinib target both RET and KDR (commonly known as VEGFR2), and such inhibitors would be predicted to have both anti-tumor and anti-angiogenic effects. KDR, is one of the 31 genes in the primary BCBM-GNS signature, and is one of the best-characterized pro-angiogenic factors reported to date. In human breast cancer, levels of KDR have been correlated with tumor progression and invasion (Forsti et al., 2007). KDR and VEGF are co-expressed in primary breast carcinomas, and their expression is increased when tumors shift to an angiogenic phenotype (Ryden et al., 2003; Yoshiji et al., 1996). Via its interaction with VEGF, KDR mediates many key components of angiogenesis, including endothelial cell proliferation and survival, as well as vessel permeability. In sunitinib-treated animals, no significant changes were found in the number of microvessels in big metastatic loci compared with the control group, but it was observed there were less enlarged and tortuous vessels within the metastatic lesions. Furthermore, the lesion-surrounding edema areas were significantly less, which could be attributed to vascular remodeling, and the anti-permeability effects of sunitinib (Carmeliet and Jain, 2011). In addition to activating KDR on vessels in a paracrine manner, VEGF secreted by tumor cells also activates KDR on itself in an autocrine manner, and directly promotes the growth of tumor cells (Masood et al., 2001). The 231-BR cell lines are high expression of KDR, and therefore it is postulated that by inhibiting the expression of KDR, the brain metastasis colonization and tumor growth are suppressed on two distinct levels.

Another target identified in the present study is Fyn, and thus dasatinib was repositioned to treat the brain metastatic animals. Dasatinib is an oral dual BCR/ABL and Src-family tyrosine kinase inhibitor. Fyn is rather unique among SRC family kinases (SFKs) since it is up regulated at the mRNA level in multiple cancers (Saito et al., 2010; Ban et al., 2008). Selective targeting of Fyn has been proven to be especially effective given the role of Fyn in tumor progression (invasion, metastasis) (Yadav and Denning, 2011). Of note, in triple negative breast cancer (TNBC) dasatinib reduced the aldehyde dehydrogenase 1 (ALDH1) positive cell population, indicating that this drug may be useful in decreasing the putative cancer stem cell population (Kurebayashi et al., 2010). In addition to its effect on cell duplication and apoptosis, one of the important actions of dasatinib relates to inhibition of metastatic dissemination. The inhibitory action of dasatinib on SRC and SFKs appears to be most relevant mechanism of action, through its controls on cell morphology, adhesion, migration and invasiveness via regulation of various signaling pathways downstream several receptors or cytoskeleton components (Ishizawar and Parsons, 2004). Moreover, SRC-Fyn regulates the tumor microenvironment (Haubeiss et al., 2010), although mutations in the ABL kinase are the defining alteration in CML, and have been the basis for molecular targeting of that disease initially with imatinib, and now with dasatinib. Evaluation of ABL activation in a panel of 8 breast cancer cell lines has shown constitutive activation of ABL in "aggressive breast cancer cells" without increases in ABL gene expression (Finn et al., 2007). Interestingly, there is a significantly increased ABL activity in the MDA-MB-231 cells, and this cell line is among those highly sensitive to dasatinib. Fyn mRNA is up-regulated by BCR-ABL1-induced oxidative stress in CML cells (Ban et al., 2008). Thus, the effects of dasatinib on brain metastasis of breast cancer may be mediated by these two mechanisms.

REFERENCES

The following references, to the extent that they provide exemplary procedural or other details supplementary to those set forth herein, are specifically incorporated herein in their entirety by express reference thereto:

Alix-Panabieres, C. et al., Full-length cytokeratin-19 is released by human tumor cells: a potential role in metastatic progression of breast cancer. *Breast Cancer Res.*, 11:R39 (2009).

Andrews D W, Scott C B, Sperduto P W, Flanders A E, Gaspar L E, Schell M C, et al., "Whole brain radiation therapy with or without stereotactic radiosurgery boost for patients with one to three brain metastases: phase III results of the RTOG 9508 randomised trial," *Lancet*, 363(9422):1665-72, 2004.

Aoyama H, Shirato H, Tago M, Nakagawa K, Toyoda T, Hatano K, et al., "Stereotactic radiosurgery plus whole-brain radiation therapy vs stereotactic radiosurgery alone for treatment of brain metastases: a randomized controlled trial," *J. Am. Med. Assoc.*, 295(21):2483-91, 2006.

Arighi, E., Borrello, M. G. and Sariola, H. RET tyrosine kinase signaling in development and cancer. *Cytokine Growth Factor Rev,* 16:441-467 (2005).

Ashburn, T. T. and Thor, K. B. Drug repositioning: identifying and developing new uses for existing drugs. *Nature Rev,* 3:673-683 (2004).

Atkins, M., Jones, C. A. and Kirkpatrick, P. Sunitinib maleate. *Nature Rev.*, 5:279-280 (2006).

Bai, W J, X Z, J M Zhu, L Ji, S T C Wong, "Tracking of migrating glioma cells in feature space. In: Biomedical Imaging: From Nano to Macro, *ISBI 4th IEEE Inte. Symp., p.* 272-275, 2007.

Ban, K. et al., BCR-ABL1 mediates up-regulation of Fyn in chronic myelogenous leukemia. *Blood,* 111:2904-2908 (2008).

Batada, N. N. et al., Stratus not altocumulus: a new view of the yeast protein interaction network. *PLoS Biol.*, 4:e317 (2006).

Bhujwalla Z M, Artemov D, Natarajan K, Ackerstaff E, Solaiyappan M., "Vascular differences detected by MRI for metastatic versus nonmetastatic breast and prostate cancer xenografts," *Neoplasia*, 3(2):143-53, 2001.

Bild, A. H. et al., Oncogenic pathway signatures in human cancers as a guide to targeted therapies. *Nature*, 439:353-357 (2006).

Bos P D, Zhang X H, Nadal C, Shu W, Gomis R R, Nguyen D X, et al., "Genes that mediate breast cancer metastasis to the brain," *Nature*, 459(7249):1005-9, 2009.

Burstein H J, Lieberman G, Slamon D J, Winer E P, Klein P., "Isolated central nervous system metastases in patients with HER2-overexpressing advanced breast cancer treated with first-line trastuzumab-based therapy," *Ann. Oncol.,* 16(11):1772-7, 2005.

Campillos, M., Kuhn, M., Gavin, A. C., Jensen, L. J. and Bork, P. Drug target identification using side-effect similarity. *Science*, 321:263-266 (2008).

Carmeliet, P. and Jain, R. K. Principles and mechanisms of vessel normalization for cancer and other angiogenic diseases. *Nature Rev.,* 10:417-427 (2011).

Chang E L, and Lo S., "Diagnosis and management of central nervous system metastases from breast cancer," *Oncologist* 8(5):398-410, 2003.

Chang, J. C. et al., Gene expression profiling for the prediction of therapeutic response to docetaxel in patients with breast cancer. *Lancet,* 362:362-369 (2003).

Chang, S. B., Miron, P., Miron, A. and Iglehart, J. D. Rapamycin inhibits proliferation of estrogen-receptor-positive breast cancer cells. *J. Surg. Res.*, 138:37-44 (2007).

Cheng X and Hung M C, "Breast cancer brain metastases," *Cancer Metastasis Rev.,* 26(3-4):635-43, 2007.

Dalerba, P., Cho, R. W. and Clarke, M. P. Cancer stem cells: models and concepts. *Annual Rev. Med.,* 58:267-284 (2007).

DeAngelis L M, Delattre J Y, Posner J B. "Radiation-induced dementia in patients cured of brain metastases," *Neurology,* 39(6):789-96, 1989.

Dewan, M. Z. et al., Stromal cell-derived factor-1 and CXCR4 receptor interaction in tumor growth and metastasis of breast cancer. *Biomedicine and pharmacotherapy=Biomed. Pharmacotherapie,* 60:273-276 (2006).

Duchnowska, R. and Szczylik, C. Central nervous system metastases in breast cancer patients administered trastuzumab. *Cancer Treatment Rev.,* 31:312-318 (2005).

Esseghir, S. et al., A role for glial cell derived neurotrophic factor induced expression by inflammatory cytokines and RET/GFR alpha 1 receptor up-regulation in breast cancer. *Cancer Res.,* 67:11732-11741 (2007).

Evans A J, James J J, Cornford E J, Chan S Y, Burrell H C, Pinder S E, et al., "Brain metastases from breast cancer: identification of a high-risk group," *Clin. Oncol. (R. Coll. Radiol.),* 16(5):345-9, 2004.

Finn, R. S. et al., Dasatinib, an orally active small molecule inhibitor of both the src and abl kinases, selectively inhibits growth of basal-type/"triple-negative" breast cancer cell lines growing in vitro. *Breast Cancer Res. Treat,* 105:319-326 (2007).

Forsti, A. et al., Polymorphisms in the KDR and POSTN genes: association with breast cancer susceptibility and prognosis. *Breast Cancer Res. Treat.,* 101:83-93 (2007).

Fulford, L. G. et al., Basal-like grade III invasive ductal carcinoma of the breast: patterns of metastasis and long-term survival. *Breast Cancer Res.,* 9:R4 (2007).

Gabos, Z. et al., Prognostic significance of human epidermal growth factor receptor positivity for the development of brain metastasis after newly diagnosed breast cancer. *J. Clin. Oncol.,* 24:5658-5663 (2006).

Gaedcke, J. et al., Predominance of the basal type and HER-2/neu type in brain metastasis from breast cancer. *Mod. Pathol.,* 20:864-870 (2007).

Gordon, M. S., N. J. V., P. Schoffski, A. Daud, A. I. Spira, B. A. O'Keeffe, T. Rafferty, Y. Lee, R. Berger, G Shapiro Activity of cabozantinib (XL184) in soft tissue and bone: Results of a phase II randomized discontinuation trial (RDT) in patients (pts) with advanced solid tumors. *J. Clin. Oncol.,* 29:3010 (2011).

Gore M E, Szczylik C, Porta C, Bracarda S, Bjarnason G A, Oudard S, et al., "Safety and efficacy of sunitinib for metastatic renal-cell carcinoma: an expanded-access trial," *Lancet Oncol.*, 10(8):757-63, 2009.

Gril, B. et al., Pazopanib reveals a role for tumor cell B-Raf in the prevention of HER2+ breast cancer brain metastasis. *Clin. Cancer Res.*, 17:142-153 (2011).

Grimshaw, M. J. et al., Mammosphere culture of metastatic breast cancer cells enriches for tumorigenic breast cancer cells. *Breast Cancer Res.*, 10:R52 (2008).

Groves M D, Hess K R, Puduvalli V K, Colman H, Conrad C A, Gilbert M R, et al., "Biomarkers of disease: cerebrospinal fluid vascular endothelial growth factor (VEGF) and stromal cell derived factor (SDF)-1 levels in patients with neoplastic meningitis (NM) due to breast cancer, lung cancer and melanoma," *J. Neurooncol.*, 94(2):229-34, 2009.

Hamosh, A., Scott, A. F., Amberger, J. S., Bocchini, C. A. and McKusick, V. A. Online Mendelian Inheritance in Man (OMIM), a knowledgebase of human genes and genetic disorders. *Nucl. Acids Res.*, 33:D514-517 (2005).

Han, J. D. et al., Evidence for dynamically organized modularity in the yeast protein-protein interaction network. *Nature*, 430:88-93 (2004).

Hatake K, Tokudome N, Ito Y., "Next generation molecular targeted agents for breast cancer: focus on EGFR and VEGFR pathways," *Breast Cancer*, 14(2):132-49, 2007.

Haubeiss, S. et al., Dasatinib reverses cancer-associated fibroblasts (CAFs) from primary lung carcinomas to a phenotype comparable to that of normal fibroblasts. *Molec. Cancer*, 9:168 (2010).

Helgason H H, Mallo H A, Droogendijk H, Haanen J G, van der Veldt A A, van den Eertwegh A J, et al., "Brain metastases in patients with renal cell cancer receiving new targeted treatment," *J. Clin. Oncol.*, 26(1):152-4, 2008.

Hendrickson F R, Lee M S, Larson M, Gelber R D., "The influence of surgery and radiation therapy on patients with brain metastases," *Int. J. Radiat. Oncol. Biol. Phys.*, 9(5):623-7, 1983.

Herrlinger U, Wiendl H, Renninger M, Forschler H, Dichgans J, Weller M., "Vascular endothelial growth factor (VEGF) in leptomeningeal metastasis: diagnostic and prognostic value," *Br. J. Cancer*, 91(2):219-24, 2004.

Hicks D G, Short S M, Prescott N L, Tarr S M, Coleman K A, Yoder B J, et al., "Breast cancers with brain metastases are more likely to be estrogen receptor negative, express the basal cytokeratin CK5/6, and overexpress HER2 or EGFR," *Am. J. Surg. Pathol.*, 30(9):1097-104, 2006.

Hwu, W. J. et al., Phase II study of temozolomide plus thalidomide for the treatment of metastatic melanoma. *J. Clin. Oncol.*, 21:3351-3356 (2003).

Hwu, W. J. et al., Temozolomide plus thalidomide in patients with brain metastases from melanoma: a phase II study. *Cancer*, 103:2590-2597 (2005).

Iorio, F. et al., Discovery of drug mode of action and drug repositioning from transcriptional responses. *Proc. Natl. Acad. Sci. USA*, 107:14621-14626 (2010).

Ishizawar, R. and Parsons, S. J. c-Src and cooperating partners in human cancer. *Cancer Cell*, 6:209-214 (2004).

Kan, Z. et al., Diverse somatic mutation patterns and pathway alterations in human cancers. *Nature*, 466:869-873 (2010).

Kang Y, Siegel P M, Shu W, Drobnjak M, Kakonen S M, Cordon-Cardo C, et al., "A multigenic program mediating breast cancer metastasis to bone," *Cancer Cell*, 3(6):537-49, 2003.

Kang, H., Watkins, G., Douglas-Jones, A., Mansel, R. E. and Jiang, W. G. The elevated level of CXCR4 is correlated with nodal metastasis of human breast cancer. *Breast* (Edinburgh, Scotland) 14:360-367 (2005).

Kaplan, R. N. et al., VEGFR1-positive haematopoietic bone marrow progenitors initiate the pre-metastatic niche. *Nature*, 438:820-827 (2005).

Keiser, M. J. et al., Predicting new molecular targets for known drugs. *Nature*, 462:175-181 (2009).

Kennecke, H. et al., Metastatic behavior of breast cancer subtypes. *J. Clin. Oncol.*, 28:3271-3277 (2010).

Kim L S, Huang S, Lu W, Lev D C, Price J E., "Vascular endothelial growth factor expression promotes the growth of breast cancer brain metastases in nude mice," *Clin. Exp. Metastasis*, 21(2):107-18, 2004.

Klein, A. et al., Identification of brain- and bone-specific breast cancer metastasis genes. *Cancer Lett.*, 276:212-220 (2009).

Klos K J, and O'Neill B P., "Brain metastases," *Neurologist*, 10(1):31-46, 2004.

Kondziolka D, Patel A, Lunsford L D, Kassam A, Flickinger J C., "Stereotactic radiosurgery plus whole brain radiotherapy versus radiotherapy alone for patients with multiple brain metastases," *Int. J. Radiat. Oncol. Biol. Phys.*, 45(2):427-34, 1999.

Koutras A K, Krikelis D, Alexandrou N, Starakis I, Kalofonos H P, "Brain metastasis in renal cell cancer responding to Sunitinib," *Anticancer Res.*, 27(6C):4255-7, 2007.

Kurebayashi, J. et al., Preferential antitumor effect of the Src inhibitor dasatinib associated with a decreased proportion of aldehyde dehydrogenase 1-positive cells in breast cancer cells of the basal B subtype. *BMC Cancer*, 10:568 (2010).

Lamb, J. et al., The Connectivity Map: using gene-expression signatures to connect small molecules, genes, and disease. *Science*, 313:1929-1935 (2006).

Lapidot, T. and Kollet, O. The essential roles of the chemokine SDF-1 and its receptor CXCR4 in human stem cell homing and repopulation of transplanted immune-deficient NOD/SCID and NOD/SCID/B2m(null) mice. *Leukemia*, 16:1992-2003 (2002).

Lassman A B, and DeAngelis L M., "Brain metastases," *Neurol. Clin.*, 21(1):1-23, vii., 2003.

Lee T H, Avraham H K, Jiang S, Avraham S., "Vascular endothelial growth factor modulates the transendothelial migration of MDA-MB-231 breast cancer cells through regulation of brain microvascular endothelial cell permeability," *J. Biol. Chem.*, 278(7):5277-84, 2003.

Li, L. and Neaves, W. B. Normal stem cells and cancer stem cells: the niche matters. *Cancer Res.*, 66:4553-4557 (2006).

Lin N U, Bellon J R, Winer E P., "CNS metastases in breast cancer," *J. Clin. Oncol.*, 22(17):3608-17, 2004.

Lin, N. U. et al., Sites of distant recurrence and clinical outcomes in patients with metastatic triple-negative breast cancer: high incidence of central nervous system metastases. *Cancer*, 113(100:2638-45 (2008).

Linderholm B, Grankvist K, Wilking N, Johansson M, Tavelin B, Henriksson R., "Correlation of vascular endothelial growth factor content with recurrences, survival, and first relapse site in primary node-positive breast carcinoma after adjuvant treatment," *J. Clin. Oncol.*, 18(7):1423-31, 2000.

Marotta, L. L. and Polyak, K. Cancer stem cells: a model in the making. *Curr. Opin. Genet. Develop.*, 19:44-50 (2009).

Martin, B. et al., Biological pathways contributing to organ-specific phenotype of brain metastatic cells. *J Proteome Res.*, 7:908-920 (2008).

Masood, R. et al., Vascular endothelial growth factor (VEGF) is an autocrine growth factor for VEGF receptor-positive human tumors. *Blood,* 98:1904-1913 (2001).

Medioni J, Cojocarasu O, Belcaceres J L, Halimi P, Oudard S., "Complete cerebral response with sunitinib for metastatic renal cell carcinoma," *Ann. Oncol.,* 18(7):1282-3, 2007.

Miller K D, Weathers T, Haney L G, Timmerman R, Dickler M, Shen J, et al., "Occult central nervous system involvement in patients with metastatic breast cancer: prevalence, predictive factors and impact on overall survival," *Ann. Oncol.,* 14(7):1072-7, 2003.

Miller, M. A. Chemical database techniques in drug discovery. *Nat. Rev. Drug Discov.,* 1:220-227 (2002).

Milo R, Shen-Orr S, Itzkovitz S, Kashtan N, Chklovskii D, Alon U. "Network motifs: simple building blocks of complex networks," *Science,* 298(5594):824-7. 2002.

Minn A J, Gupta G P, Siegel P M, Bos P D, Shu W, Giri D D, et al., "Genes that mediate breast cancer metastasis to lung." *Nature,* 436(7050):518-24, 2005.

Minn, A. J. et al., Distinct organ-specific metastatic potential of individual breast cancer cells and primary tumors. *J. Clin. Invest.,* 115:44-55 (2005). (2005).

Mintz A H, Kestle J, Rathbone M P, Gaspar L, Hugenholtz H, Fisher B, et al., "A randomized trial to assess the efficacy of surgery in addition to radiotherapy in patients with a single cerebral metastasis," *Cancer,* 78(7):1470-6, 1996.

Monsky W L, Mouta Carreira C, Tsuzuki Y, Gohongi T, Fukumura D, Jain R K., "Role of host microenvironment in angiogenesis and microvascular functions in human breast cancer xenografts: mammary fat pad versus cranial tumors," *Clin. Cancer Res.,* 8(4):1008-13, 2002.

Morandi, A., Plaza-Menacho, I. and Isacke, C. M. RET in breast cancer: functional and therapeutic implications. *Trends Molec. Med.,* 17:149-157 (2011).

Motzer R J, Michaelson M D, Redman B G, Hudes G R, Wilding G, Figlin R A, et al., "Activity of SU11248, a multitargeted inhibitor of vascular endothelial growth factor receptor and platelet-derived growth factor receptor, in patients with metastatic renal cell carcinoma," *J. Clin. Oncol.,* 24(1):16-24, 2006.

Motzer R J, Rini B I, Bukowski R M, Curti B D, George D J, Hudes G R, et al., "Sunitinib in patients with metastatic renal cell carcinoma," *J. Am. Med. Assoc.,* 295(21):2516-24, 2006.

Murray, L. J. et al., SU11248 inhibits tumor growth and CSF-1R-dependent osteolysis in an experimental breast cancer bone metastasis model. *Clin. Exper. Metastasis,* 20:757-766 (2003).

Narita Y and Shibui S, "Strategy of surgery and radiation therapy for brain metastases," *Int. J. Clin. Oncol.,* 14(4): 275-80, 2009.

Neman, J., Somlo, G. and Jandial, R. Classification of genomic changes in breast cancer brain metastasis. *Neurosurgery,* 67:N18-19 (2010).

Noordijk E M, Vecht C J, Haaxma-Reiche H, Padberg G W, Voormolen J H, Hoekstra F H, et al., "The choice of treatment of single brain metastasis should be based on extracranial tumor activity and age," *Int. J. Radiat. Oncol. Biol. Phys.,* 29(4):711-7, 1994.

Ono M, Ando M, Yunokawa M, Nakano E, Yonemori K, Matsumoto K, et al. "Brain metastases in patients who receive trastuzumab-containing chemotherapy for HER2-overexpressing metastatic breast cancer," *Int. J. Clin. Oncol.,* 14(1):48-52, 2009.

Pajouhesh, H. and Lenz, G. R. Medicinal chemical properties of successful central nervous system drugs. *NeuroRx,* 2:541-553 (2005).

Palmieri D, Bronder J L, Herring J M, Yoneda T, Weil R J, Stark A M, et al., "Her-2 overexpression increases the metastatic outgrowth of breast cancer cells in the brain," *Cancer Res.,* 67(9):4190-8. 2007.

Palmieri D, Smith Q R, Lockman P R, Bronder J, Gril B, Chambers A F, et al., "Brain metastases of breast cancer," *Breast Dis.,* 26:139-47, 2006.

Palmieri, D. et al., Vorinostat inhibits brain metastatic colonization in a model of triple-negative breast cancer and induces DNA double-strand breaks. *Clin. Cancer Res.,* 15:6148-6157 (2009).

Pestalozzi B C, Zahrieh D, Price K N, Holmberg S B, Lindtner J, Collins J, et al., "Identifying breast cancer patients at risk for Central Nervous System (CNS) metastases in trials of the International Breast Cancer Study Group (IBCSG)," *Ann. Oncol.,* 17(6):935-44, 2006.

Plaza-Menacho, I. et al., Targeting the receptor tyrosine kinase RET sensitizes breast cancer cells to tamoxifen treatment and reveals a role for RET in endocrine resistance. *Oncogene,* 29:4648-4657 (2010).

Porkka, K. et al., Dasatinib crosses the blood-brain barrier and is an efficient therapy for central nervous system Philadelphia chromosome-positive leukemia. *Blood,* 112: 1005-1012 (2008).

Portella, G et al., Development of mammary and cutaneous gland tumors in transgenic mice carrying the RET/PTC1 oncogene. *Oncogene,* 13:2021-2026 (1996).

Ramaswamy, S., Ross, K. N., Lander, E. S. and Golub, T. R. A molecular signature of metastasis in primary solid tumors. *Nature Genet.,* 33:49-54 (2003).

Rodriguez, A. A. et al., DNA repair signature is associated with anthracycline response in triple negative breast cancer patients. *Breast Cancer Res. Treat.,* 123:189-196 (2010).

Rosner D, Nemoto T, Lane W W., "Chemotherapy induces regression of brain metastases in breast carcinoma," *Cancer,* 58(4):832-9, 1986.

Ryberg M, Nielsen D, Osterlind K, Andersen P K, Skovsgaard T, Dombernowsky P., "Predictors of central nervous system metastasis in patients with metastatic breast cancer. A competing risk analysis of 579 patients treated with epirubicin-based chemotherapy," *Breast Cancer Res Treat* 91(3):217-25, 2005.

Ryden, L. et al., Tumor specific VEGF-A and VEGFR2/KDR protein are co-expressed in breast cancer. *Breast Cancer Res. Treat.,* 82:147-154 (2003).

Saito, Y. D., Jensen, A. R., Salgia, R. and Posadas, E. M. Fyn: a novel molecular target in cancer. *Cancer,* 116: 1629-1637 (2010).

Schaefer, C. F. et al., PID: the Pathway Interaction Database. *Nucl. Acids Res.,* 37:D674-679 (2009).

Shaffrey M E, Mut M, Asher A L, Burri S H, Chahlavi A, Chang S M, et al., "Brain metastases,"*Curr. Probl. Surg.,* 41(8):665-741, 2004.

Shapira, M., Kakiashvili, E., Rosenberg, T. and Hershko, D. D. The mTOR inhibitor rapamycin down-regulates the expression of the ubiquitin ligase subunit Skp2 in breast cancer cells. *Breast Cancer Res.,* 8:R46 (2006).

Shats, I. et al., Using a stem cell-based signature to guide therapeutic selection in cancer. *Cancer Res.,* 71:1772-1780 (2010).

Slimane K, Andre F, Delaloge S, Dunant A, Perez A, Grenier J, et al., "Risk factors for brain relapse in patients with metastatic breast cancer," *Ann. Oncol.*, 15(11):1640-4, 2004.

Smid, M. et al., Subtypes of breast cancer show preferential site of relapse. *Cancer Res.*, 68:3108-3114 (2008).

Sneed P K, Suh J H, Goetsch S J, Sanghavi S N, Chappell R, Buatti J M, et al., "A multi-institutional review of radiosurgery alone vs. radiosurgery with whole brain radiotherapy as the initial management of brain metastases," *Int. J. Radiat. Oncol. Biol. Phys.*, 53(3):519-26, 2002.

Souglakos J, Vamvakas L, Apostolaki S, Perraki M, Saridaki Z, Kazakou I, et al., "Central nervous system relapse in patients with breast cancer is associated with advanced stages, with the presence of circulating occult tumor cells and with the HER2/neu status," *Breast Cancer Res.*, 8(4):R36, 2006.

Tham Y L, Sexton K, Kramer R, Hilsenbeck S, Elledge R., "Primary breast cancer phenotypes associated with propensity for central nervous system metastases," *Cancer*, 107(4):696-704, 2006.

Unger, K. et al., Novel gene rearrangements in transformed breast cells identified by high-resolution breakpoint analysis of chromosomal aberrations. *Endocrine-Related Cancer*, 17:87-98 (2010).

Vandesompele, J. et al., Accurate normalization of real-time quantitative RT-PCR data by geometric averaging of multiple internal control genes. *Genome Biology*, 3:RESEARCH0034(2002).

Wadasadawala, T., Gupta, S., Bagul, V. and Patil, N. Brain metastases from breast cancer: management approach. *J. Cancer Res. Ther.*, 3:157-165 (2007).

Walbert, T. and Gilbert, M. R. The role of chemotherapy in the treatment of patients with brain metastases from solid tumors. *Int. J. Clin. Oncol. (Japan Soc. Clin. Oncol.)* 14:299-306 (2009).

Wang, Y. et al., Gene-expression profiles to predict distant metastasis of lymph-node-negative primary breast cancer. *Lancet*, 365:671-679 (2005).

Weigelt, B. et al., Gene expression profiles of primary breast tumors maintained in distant metastases. *Proc. Natl. Acad. Sci. USA*, 100:15901-15905 (2003).

Weil R J et al., "Breast cancer metastasis to the central nervous system," *Am. J. Pathol.*, 167(4):913-20, 2005.

Yadav, V. and Denning, M. F. Fyn is induced by Ras/PI3K/Akt signaling and is required for enhanced invasion/migration. *Molec. Carcinogenesis*, 50:346-352 (2011).

Yildirim, M. A., Goh, K. I., Cusick, M. E., Barabasi, A. L. and Vidal, M. Drug-target network. *Nat. Biotechnol.*, 25:1119-1126 (2007).

Yoneda, T., Williams, P. J., Hiraga, T., Niewolna, M. and Nishimura, R. A bone-seeking clone exhibits different biological properties from the MDA-MB-231 parental human breast cancer cells and a brain-seeking clone in vivo and in vitro. *J. Bone Miner. Res.*, 16:1486-1495 (2001).

Yoshiji, H., Gomez, D. E., Shibuya, M. and Thorgeirsson, U. P. Expression of vascular endothelial growth factor, its receptor, and other angiogenic factors in human breast cancer. *Cancer Res.*, 56:2013-2016 (1996).

Zhao, H. et al., The effect of mTOR inhibition alone or combined with MEK inhibitors on brain metastasis: an in vivo analysis in triple-negative breast cancer models. *Breast Cancer Res. Treat.*, in print (2011).

Zuercher, W. J., Turunen, B. J. and Lackey, K. E. Current review of small molecule Ret kinase inhibitors. *Mini Rev. Med. Chem.*, 10:138-146 (2010).

All of the compositions and methods disclosed and claimed herein can be made and executed without undue experimentation in light of the present disclosure. While the compositions and methods of this invention have been described in terms of exemplary embodiments, it will be apparent to those of ordinary skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those of ordinary skill in the art are deemed to be within the spirit, scope and concept of the invention as defined by the appended claims. Accordingly, the exclusive rights sought to be patented are as described in the claims below.

What is claimed is:

1. A method of treating brain metastasis of breast cancer in a human patient, the method comprising:

assaying the mRNA levels of seven biomarkers in a primary breast cancer sample obtained from a patient having brain metastasis of breast cancer, wherein the seven biomarkers are selected from the group consisting of ret proto-oncogene (RET), proto-oncogene tyrosine-protein kinase Fyn (FYN), kinase insert domain receptor (KDR), RAF proto-oncogene serine/threonine-protein kinase (RAF1), NF-kappa-B p105 subunit (NFKB1), histone deacetylase 1 (HDAC1), and histone deacetylase 2 (HDAC2);

determining that the mRNA level of RET, FYN, or KDR is higher than a corresponding control level in primary breast cancer samples obtained from control subjects without brain metastasis of breast cancer; and administering to the patient (i) Sunitinib when the mRNA level of RET or KDR is higher or, in the alternative, (ii) Dasatinib when the mRNA level of FYN is higher.

2. The method of claim 1, wherein the expression level of KDR is higher in the primary breast cancer sample and the drug administered is Sunitinib.

3. The method of claim 1, wherein the expression level of FYN is higher in the primary breast cancer sample and the drug administered is Dasatinib.

4. The method of claim 1, wherein the expression level of RET is higher in the primary breast cancer sample and the drug administered is Sunitinib.

5. The method of claim 1, wherein the assaying step is carried out with RT-PCR.

* * * * *